US008017132B2

(12) United States Patent
Sebo et al.

(10) Patent No.: US 8,017,132 B2
(45) Date of Patent: Sep. 13, 2011

(54) MUTANT CYAA POLYPEPTIDES AND POLYPEPTIDE DERIVATIVES SUITABLE FOR THE DELIVERY OF IMMUNOGENIC MOLECULES INTO A CELL

(75) Inventors: Peter Sebo, Prague (CZ); Claude Leclerc, Paris (FR); Adriana Osickova, Prague (CZ); Catherine Fayolle, Epinay sur Orge (FR); Jiri Masin, Uvaly (CZ); Jan Krusek, Prague (CZ); Radim Osicka, Prague (CZ); Marek Basler, Prague (CZ)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 12/409,324

(22) Filed: Mar. 23, 2009

(65) Prior Publication Data

US 2010/0239550 A1    Sep. 23, 2010

(51) Int. Cl.
*A61K 39/10* (2006.01)
(52) U.S. Cl. ............... 424/240.1; 424/185.1; 424/190.1; 424/196.11; 424/201.1
(58) Field of Classification Search ........................ None
See application file for complete search history.

(56) References Cited

FOREIGN PATENT DOCUMENTS
WO    WO 2005/035557 A2    4/2005

OTHER PUBLICATIONS

Greenspan et al (Nature Biotechnology 7: 936-937, 1999).*
Chothia et al (The EMBO Journal, 1986, 5/4:823-26).*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
European Search Report EP09155929 dated May 13, 2009.
Guermonprez, P., et al., "*Bordetella pertussis* Adenylate Cyclase Toxin: A Vehicle to Deliver CD8-Positive T-Cell Epitopes into Antigen-Presenting Cells," *Methods in Enzymology*, (2000), 326:527-542.
Masin, J., et al. "Acylation of Lysine 860 Allows Tight Binding and Cytotoxicity of *Bordetella* Adenylate Cyclase on CD11b-Expressing Cells," *Biochemistry*, (2005), 44, 12759-12766.
Radovan, F., et al., "Third Activity of Bordetella Adenylate Cyclase (AC) Toxin-Hemolysin," "Membrane Translocation of AC Domain Polypeptide Promotes Calcium Influx Into CD11b+Monocytes Independently of the Catalytic and Hemolytic Activities," *Journal of Biological Chemistry*, (2007), 282(5):2808-2820.
Basar, T., et al., The Conserved Lysine 860 in the Additional Fatty-acylation Site of *Bordetella pertussis* Adenylate Cyclase Is Crucial for Toxin Function Independently of Its Acylation Status, *The Journal of Biological Chemistry*, (1999), 274(16):10777-10783.
Basler, M., et al., "Pore-Forming and Enzymatic Activities of *Bordetella pertussis* Adenylate Cyclase Toxin Synergize in Promoting Lysis of Monocytes," *Infection and Immunity*, (2006), 74(4):2207-2214.
Basler, M., et al., "Segments Crucial for Membrane Translocation and Pore-forming Activity of *Bordetella* Adenylate Cyclase Toxin," *The Journal of Biological Chemistry*, (2007), 282(17):12419-12429.
Database EMBL XP-002525392, *Bifunctional Hemolysin-Adenylate Cyclase Precursor [Bordetella Parapertussis 12822]*, Jul. 21, 2008.
Database EMBL XP 002525393, "CyaA [Bordetella Pertussis]," Apr. 18, 2005.
Database EMBL XP-002525394, *Bifunctional Hemolysin-Adenylate Cyclase Precursor [Bordetella Bronchiseptica RB50]*, Jul. 29, 2008.
Database EMBL XP-002525395, *Adenylate Cyclase Toxin [Bordetella Hinzii]*, Nov. 4, 2005.
Betsou, F., et al., "Bordetella bronchiseptica adenylate cyclase-hemolysin (cya) gene, complete cds," GenBank Accession U22953, Mar. 23, 1995.
Betsou, F., et al., "Cloning and sequence of the Bordetella bronchiseptica adenylate cyclase-hemolysin-encoding gene: comparison with the Bordetella pertussis gene," Gene 162, 165-166 (1995).
Clustal 2.0.10 sequence alignment of SEQ ID No. 1 with NP_882677.1, performed Jul. 22, 2010.
Donato, G.M. et al., "Bordetella hinzii strain BC-306 adenylate cyclase toxin (cyaA) gene, complete cds," GenBank Accession DQ102773, Nov. 4, 2005.
Donato,G.M., et al., "Adenylate cyclase toxin (ACT) from Bordetella hinzii: characterization and differences from ACT of Bordetella pertussis." J. Bacteriol. 187 (22), 7579-7588 (2005).
Donato, G.M. et al., "Bordetella hinzii strain LMG 13501 adenylate cyclase toxin (cyaA) gene, complete cds," GenBank Accession DQ007078, Nov. 4, 2005.
NCBI Genome Project, "Bordetella parapertussis 12822, complete genome," GenBank Accession NC_002928, Aug. 12, 2003, pp. 1 and 85 of 1042.
Parkhill, J., et al., "Comparative analysis of the genome sequences of Bordetella pertussis, Bordetella parapertussis and Bordetella bronchiseptica," Nat. Genet. 35 (1), 32-40 (2003).

* cited by examiner

*Primary Examiner* — Jennifer Graser
(74) *Attorney, Agent, or Firm* — Finnegan, Henderson, Farabow, Garrett & Dunner, L.L.P.

(57) ABSTRACT

The invention relates to mutant CyaA/E570Q+K860 polypeptides suitable for use as proteinaceous vectors for delivering one or more molecules of interest into a cell, in particular into a cell expressing the CD11b receptor. The invention further relates to polypeptide derivatives suitable for eliciting an immune response in a host.
The invention is more particularly directed to polypeptides derived from an adenylate cyclase protein (CyaA) either under the form of a toxin or of a toxoid, which are mutant polypeptides. Said mutant polypeptides are capable of retaining the binding activity of native CyaA to a target cell and preferably of also retaining the translocating activity of native CyaA through its N-terminal domain into target cells and furthermore have a pore-forming activity which is reduced or suppressed as compared to that of the native CyaA toxin.

19 Claims, 17 Drawing Sheets

Figure 2:
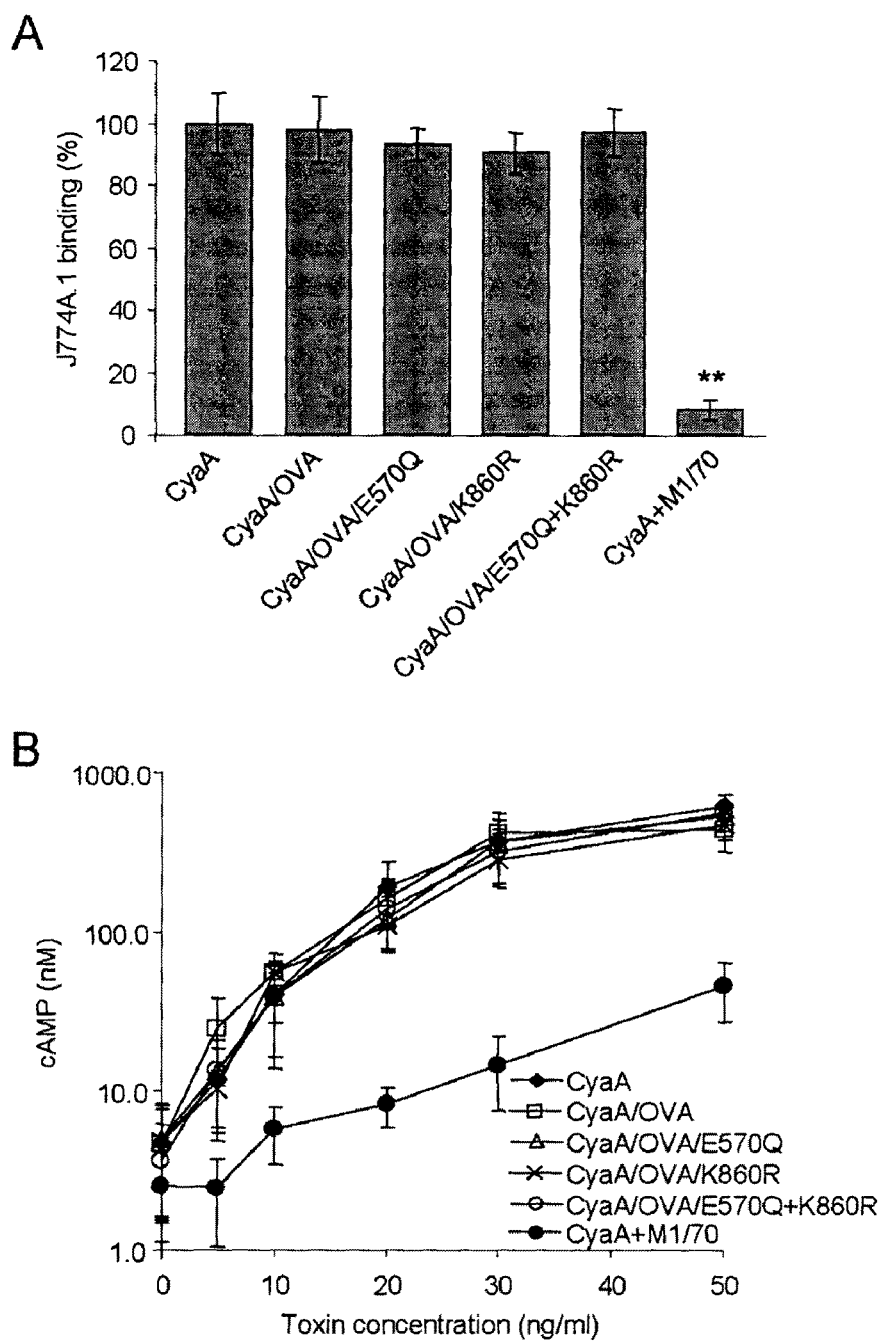

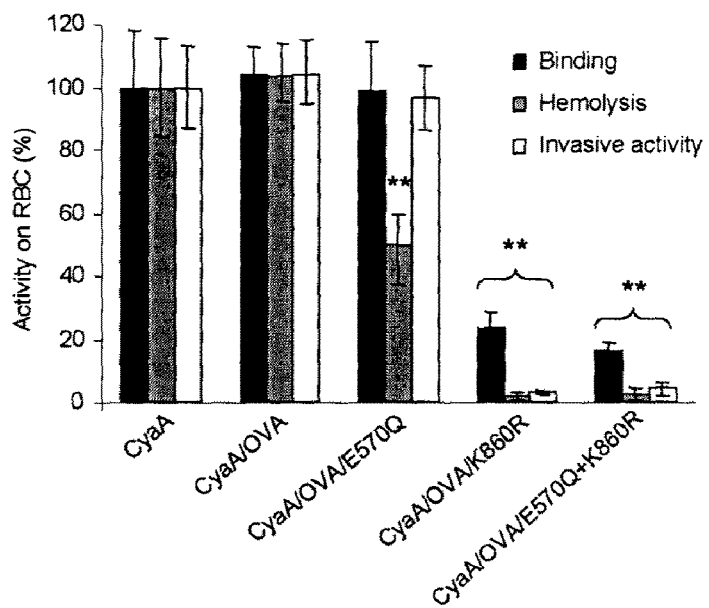
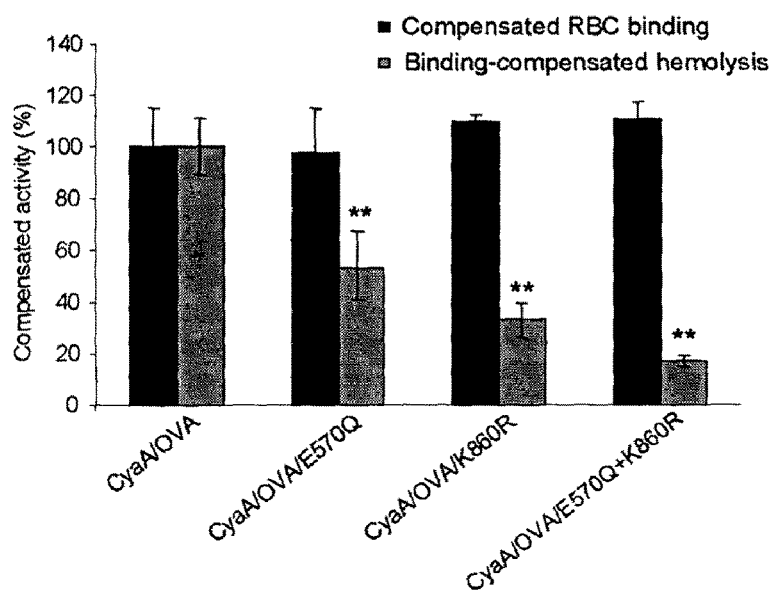
Figure 1

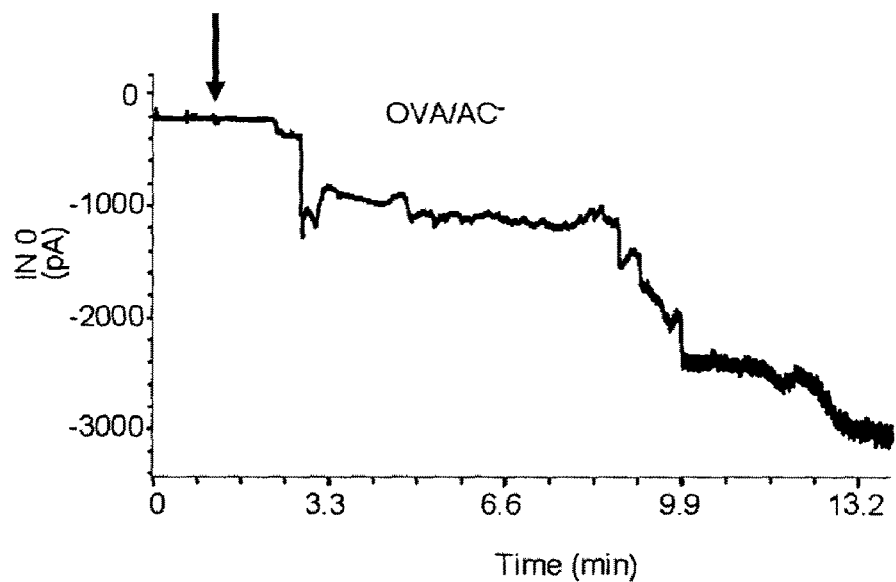
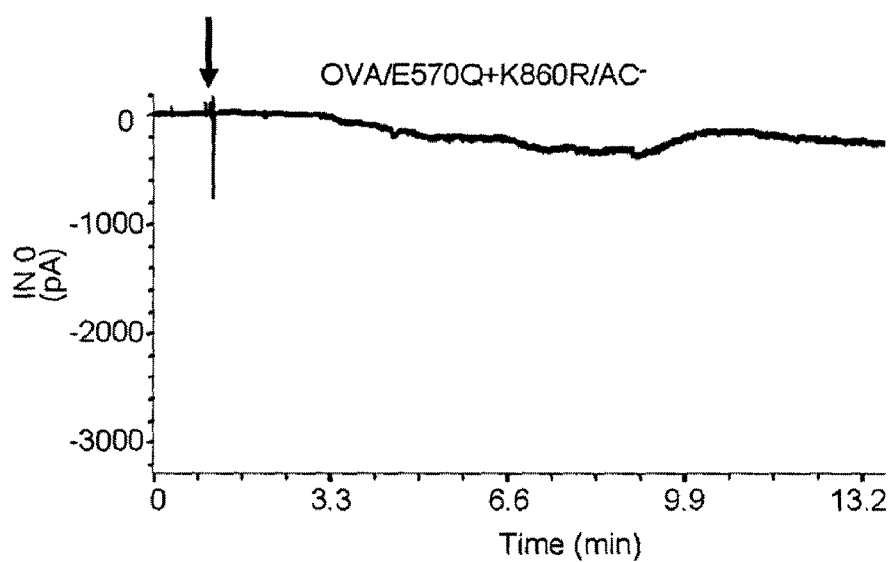
Figure 3

```
   1 MQQSHQAGYA NAADRESGIP AAVLDGIKAV AKEKNATLMF RLVNPHSTSL IAEGVATKGL
  61 GVHAKSSDWG LQAGYIPVNP NLSKLFGRAP EVIARADNDV NSSLAHGHTA VDLTLSKERL
 121 DYLRQAGLVT GMADGVVASN HAGYEQFEFR VKETSDGRYA VQYRRKGGDD FEAVKVIGNA
 181 AGIPLTADID MFAIMPHLSN FRDSARSSVT SGDSVTDYLA RTRRAASEAT GGLDRERIDL
 241 LWKIARAGAR SAVGTEARRQ FRYDGDMNIG VITDFELEVR NALNRRAHAV GAQDVVQHGT
 301 EQNNPFPEAD EKIFVVSATG ESQMLTRGQL KEYIGQQRGE GYVFYENRAY GVAGKSLFDD
 361 GLGAAPGVPS GRSKFSPDVL ETVPASPGLR RPSLGAVERQ DSGYDSLDGV GSRSFSLGEV
 421 SDMAAVEAAE LEMTRQVLHA GARQDDAEPG VSGASAHWGQ RALQGAQAVA AAQRLVHAIA
 481 LMTQFGRAGS TNTPQEAASL SAAVFGLGEA SSAVAETVSG FFRGSSRWAG GFGVAGGAMA
 541 LGGGIAAAVG AGMSLTDDAP AGQKAAAGAE IALQLTGGTV ELASSIALAL AAARGVTSGL
 601 QVAGASAGAA AGALAAALSP MEIYGLVQQS HYADQLDKLA QESSAYGYEG DALLAQLYRD
 661 KTAAEGAVAG VSAVLSTVGA AVSIAAAASV VGAPVAVVTS LLTGALNGIL RGVQQPIIEK
 721 LANDYARKID ELGGPQAYFE KNLQARHEQL ANSDGLRKML ADLQAGWNAS SVIGVQTTEI
 781 SKSALELAAI TGNADNLKSV DVFVDRFVQG ERVAGQPVVL DVAAGGIDIA SRKGERPALT
 841 FITPLAAPGE EQRRRTKTGK SEFTTFVEIV GKQDRWRIRD GAADTTIDLA KVVSQLVDAN
 901 GVLKHSIKLD VIGGDGDDVV LANASRIHYD GGAGTNTVSY AALGRQDSIT VSADGERFNV
 961 RKQLNNANVY REGVATQTTA YGKRTENVQY RHVELARVGQ VVEVDTLEHV QHIIGGAGND
1021 SITGNAHDNF LAGGSGDDRL DGGAGNDTLV GGEGQNTVIG GAGDDVFLQD LGVWSNQLDG
1081 GAGVDTVKYN VHQPSEERLE RMGDTGIHAD LQKGTVEKWP ALNLFSVDHV KNIENLHGSR
1141 LNDRIAGDDQ DNELWGHDGN DTIRGRGGDD ILRGGLGLDT LYGEDGNDIF LQDDETVSDD
1201 IDGGAGLDTV DYSAMIHPGR IVAPHEYGFG IEADLSREWV RKASALGVDY YDNVRNVENV
1261 IGTSMKDVLI GDAQANTLMG QGGDDTVRGG DGDDLLFGGD GNDMLYGDAG NDTLYGGLGD
1321 DTLEGGAGND WFGQTQAREH DVLRGGDGVD TVDYSQTGAH AGIAAGRIGL GILADLGAGR
1381 VDKLGEAGSS AYDTVSGIEN VVGTELADRI TGDAQANVLR GAGGADVLAG GEGDDVLLGG
1441 DGDDQLSGDA GRDRLYGEAG DDWFFQDAAN AGNLLDGGDG RDTVDFSGPG RGLDAGAKGV
1501 FLSLGKGFAS LMDEPETSNV LRNIENAVGS ARDDVLIGDA GANVLNGLAG NDVLSGGAGD
1561 DVLLGDEGSD LLSGDAGNDD LFGGQGDDTY LFGVGYHDT IYESGGGHDT IRINAGADQL
1621 WFARQGNDLE IRILGTDDAL TVHDWYRDAD HRVEIIHAAN QAVDQAGIEK LVEAMAQYPD
1681 PGAAAAAPPA ARVPDTLMQS LAVNWR
```

Figure 6

```
   1 MQQSHQAGYA NAADRESGIP AAVLDGIKAV AKEKNATLMF RLVNPHSTSL IAEGVATKGL
  61 GVHAKSSDWG LQAGYIPVNP NLSKLFGRAP EVIARADNDV NSSLAHGHTA VDLTLSKERL
 121 DYLRQAGLVT GMADGVVASN HAGYEQFEFR VKETSDGRYA VQYRRKGGDD FEAVKVIGNA
 181 AGIPLTADID MFAIMPHLSN FRDSARSSVT SGDSVTDYLA RTRRAASEAT GGLDRERIDL
 241 LWKIARAGAR SAVGTEARRQ FRYDGDMNIG VITDFELEVR NALNRRAHAV GAQDVVQHGT
 301 EQNNPFPEAD EKIFVVSATG ESQMLTRGQL KEYIGQQRGE GYVFYENRAY GVAGKSLFDD
 361 GLGAAPGVPS GRSKFSPDVL ETVPASPGLR RPSLGAVERQ DSGYDSLDGV GSRSFSLGEV
 421 SDMAAVEAAE LEMTRQVLHA GARQDDAEPG VSGASAHWGQ RALQGAQAVA AAQRLVHAIA
 481 LMTQFGRAGS TNTPQEAASL SAAVFGLGEA SSAVAETVSG FFRGSSRWAG GFGVAGGAMA
 541 LGGGIAAAVG AGMSLTDDAP AGQKAAAGAQ IALQLTGGTV ELASSIALAL AAARGVTSGL
 601 QVAGASAGAA AGALAAALSP MEIYGLVQQS HYADQLDKLA QESSAYGYEG DALLAQLYRD
 661 KTAAEGAVAG VSAVLSTVGA AVSIAAAASV VGAPVAVVTS LLTGALNGIL RGVQQPIIEK
 721 LANDYARKID ELGGPQAYFE KNLQARHEQL ANSDGLRKML ADLQAGWNAS SVIGVQTTEI
 781 SKSALELAAI TGNADNLKSV DVFVDRFVQG ERVAGQPVVL DVAAGGIDIA SRKGERPALT
 841 FITPLAAPGE EQRRRTKTGR SEFTTFVEIV GKQDRWRIRD GAADTTIDLA KVVSQLVDAN
 901 GVLKHSIKLD VIGGDGDDVV LANASRIHYD GGAGTNTVSY AALGRQDSIT VSADGERFNV
 961 RKQLNNANVY REGVATQTTA YGKRTENVQY RHVELARVGQ VVEVDTLEHV QHIIGGAGND
1021 SITGNAHDNF LAGGSGDDRL DGGAGNDTLV GGEGQNTVIG GAGDDVFLQD LGVWSNQLDG
1081 GAGVDTVKYN VHQPSEERLE RMGDTGIHAD LQKGTVEKWP ALNLFSVDHV KNIENLHGSR
1141 LNDRIAGDDQ DNELWGHDGN DTIRGRGGDD ILRGGLGLDT LYGEDGNDIF LQDDETVSDD
1201 IDGGAGLDTV DYSAMIHPGR IVAPHEYGFG IEADLSREWV RKASALGVDY YDNVRNVENV
1261 IGTSMKDVLI GDAQANTLMG QGGDDTVRGG DGDDLLFGGD GNDMLYGDAG NDTLYGGLGD
1321 DTLEGGAGND WFGQTQAREH DVLRGGDGVD TVDYSQTGAH AGIAAGRIGL GILADLGAGR
1381 VDKLGEAGSS AYDTVSGIEN VVGTELADRI TGDAQANVLR GAGGADVLAG GEGDDVLLGG
1441 DGDDQLSGDA GRDRLYGEAG DDWFFQDAAN AGNLLDGGDG RDTVDFSGPG RGLDAGAKGV
1501 FLSLGKGFAS LMDEPETSNV LRNIENAVGS ARDDVLIGDA GANVLNGLAG NDVLSGGAGD
1561 DVLLGDEGSD LLSGDAGNDD LFGGQGDDTY LFGVGYGHDT IYESGGGHDT IRINAGADQL
1621 WFARQGNDLE IRILGTDDAL TVHDWYRDAD HRVEIIHAAN QAVDQAGIEK LVEAMAQYPD
1681 PGAAAAAPPA ARVPDTLMQS LAVNWR
```

Figure 7

```
   1 MQQSHQAGYA NAADRESGIP AAVLDGIKAV AKEKNATLMF RLVNPHSTSL IAEGVATKGL
  61 GVHAKSSDWG LQAGYIPVNP NLSKLFGRAP EVIARADNDV NSSLAHGHTA VDLTLSKERL
 121 DYLRQAGLVT GMADGVVASN HAGYEQFEFR VKETSDGRYA VQYRRKGGDD FEAVKVIGNA
 181 AGIPLTADGS IDMFAIMPHL SNFRDSARSS VTSGDSVTDY LARTRRAASE ATGGLDRERI
 241 DLLWKIARAG ARSAVGTEAR RQFRYDGDMN IGVITDFELE VRNALNRRAH AVGAQDVVQH
 301 GTEQNNPFPE ADEKIFVVSA TGESQMLTRG QLKEYIGQQR GEGYVFYENR AYGVAGKSLF
 361 DDGLGAAPGV PSGRSKFSPD VLETVPASPG LRRPSLGAVE RQDSGYDSLD GVGSRSFSLG
 421 EVSDMAAVEA AELEMTRQVL HAGARQDDAE PGVSGASAHW GQRALQGAQA VAAAQRLVHA
 481 IALMTQFGRA GSTNTPQEAA SLSAAVFGLG EASSAVAETV SGFFRGSSRW AGGFGVAGGA
 541 MALGGGIAAA VGAGMSLTDD APAGQKAAAG AQIALQLTGG TVELASSIAL ALAAARGVTS
 601 GLQVAGASAG AAAGALAAAL SPMEIYGLVQ QSHYADQLDK LAQESSAYGY EGDALLAQLY
 661 RDKTAAEGAV AGVSAVLSTV GAAVSIAAAA SVVGAPVAVV TSLLTGALNG ILRGVQQPII
 721 EKLANDYARK IDELGGPQAY FEKNLQARHE QLANSDGLRK MLADLQAGWN ASSVIGVQTT
 781 EISKSALELA AITGNADNLK SVDVFVDRFV QGERVAGQPV VLDVAAGGID IASRKGERPA
 841 LTFITPLAAP GEEQRRRTKT GRSEFTTFVE IVGKQDRWRI RDGAADTTID LAKVVSQLVD
 901 ANGVLKHSIK LDVIGGDGDD VVLANASRIH YDGGAGTNTV SYAALGRQDS ITVSADGERF
 960 NVRKQLNNAN VYREGVATQT TAYGKRTENV QYRHVELARV GQVVEVDTLE HVQHIIGGAG
1021 NDSITGNAHD NFLAGGSGDD RLDGGAGNDT LVGGEGQNTV IGGAGDDVFL QDLGWSNQL
1081 DGGAGVDTVK YNVHQPSEER LERMGDTGIH ADLQKGTVEK WPALNLFSVD HVKNIENLHG
1141 SRLNDRIAGD DQDNELWGHD GNDTIRGRGG DDILRGGLGL DTLYGEDGND IFLQDDETVS
1201 DDIDGGAGLD TVDYSAMIHP GRIVAPHEYG FGIEADLSRE WVRKASALGV DYYDNVRNVE
1261 NVIGTSMKDV LIGDAQANTL MGQGGDDTVR GGDGDDLLFG GDGNDMLYGD AGNDTLYGGL
1321 GDDTLEGGAG NDWFGQTQAR EHDVLRGGDG VDTVDYSQTG AHAGIAAGRI GLGILADLGA
1381 GRVDKLGEAG SSAYDTVSGI ENVVGTELAD RITGDAQANV LRGAGGADVL AGGEGDDVLL
1441 GGDGDDQLSG DAGRDRLYGE AGDDWFFQDA ANAGNLLDGG DGRDTVDFSG PGRGLDAGAK
1501 GVFLSLGKGF ASLMDEPETS NVLRNIENAV GSARDDVLIG DAGANVLNGL AGNDVLSGGA
1561 GDDVLLGDEG SDLLSGDAGN DDLFGGQGDD TYLFGVGYGH DTIYESGGGH DTIRINAGAD
1621 QLWFARQGND LEIRILGTDD ALTVHDWYRD ADHRVEIIHA ANQAVDQAGI EKLVEAMAQY
1681 PDPGAAAAAP PAARVPDTLM QSLAVNWR
```

Figure 8

```
  1    MQQSHQAGYA NAADRESGIP AAVLDGIKAV AKEKNATLMF RLVNPHSTSL IAEGVATKGL
 61    GVHAKSSDWG LQAGYIPVNP NLSKLFGRAP EVIARADNDV NSSLAHGHTA VDLTLSKERL
121    DYLRQAGLVT GMADGVVASN HAGYEQFEFR VKETSDGRYA VQYRRKGGDD FEAVKVIGNA
181    AGIPLTADGS IDMFAIMPHL SNFRDSARSS VTSGDSVTDY LARTRRAASE ATGGVLSIIN
241    FEKLVHLDRE RIDLLWKIAR AGARSAVGTE ARRQFRYDGD MNIGVITDFE LEVRNALNRR
301    AHAVGAQDVV QHGTEQNNPF PEADEKIFVV SATGESQMLT RGQLKEYIGQ QRGEGYVFYE
361    NRAYGVAGKS LFDDGLGAAP GVPSGRSKFS PDVLETVPAS PGLRRPSLGA VERQDSGYDS
421    LDGVGSRSFS LGEVSDMAAV EAAELEMTRQ VLHAGARQDD AEPGVSGASA HWGQRALQGA
481    QAVAAAQRLV HAIALMTQFG RAGSTNTPQE AASLSAAVFG LGEASSAVAE TVSGFFRGSS
541    RWAGGFGVAG GAMALGGGIA AAVGAGMSLT DDAPAGQKAA AGAQIALQLT GGTVELASSI
601    ALALAAARGV TSGLQVAGAS AGAAAGALAA ALSPMEIYGL VQQSHYADQL DKLAQESSAY
661    GYEGDALLAQ LYRDKTAAEG AVAGVSAVLS TVGAAVSIAA AASVVGAPVA VVTSLLTGAL
721    NGILRGVQQP IIEKLANDYA RKIDELGGPQ AYFEKNLQAR HEQLANSDGL RKMLADLQAG
781    WNASSVIGVQ TTEISKSALE LAAITGNADN LKSVDVFVDR FVQGERVAGQ PVVLDVAAGG
841    IDIASRKGER PALTFITPLA APGEEQRRRT KTGRSEFTTF VEIVGKQDRW RIRDGAADTT
901    IDLAKVVSQL VDANGVLKHS IKLDVIGGDG DDVVLANASR IHYDGGAGTN TVSYAALGRQ
961    DSITVSADGE RFNVRKQLNN ANVYREGVAT QTTAYGKRTE NVQYRHVELA RVGQVVEVDT
1021   LEHVQHIIGG AGNDSITGNA HDNFLAGGSG DDRLDGGAGN DTLVGGEGQN TVIGGAGDDV
1081   FLQDLGVWSN QLDGGAGVDT VKYNVHQPSE ERLERMGDTG IHADLQKGTV EKWPALNLFS
1141   VDHVKNIENL HGSRLNDRIA GDDQDNELWG HDGNDTIRGR GGDDILRGGL GLDTLYGEDG
1201   NDIFLQDDET VSDDIDGGAG LDTVDYSAMI HPGRIVAPHE YGFGIEADLS REWVRKASAL
1261   GVDYYDNVRN VENVIGTSMK DVLIGDAQAN TLMGQGGDDT VRGGDGDDLL FGGDGNDMLY
1321   GDAGNDTLYG GLGDDTLEGG AGNDWFGQTQ AREHDVLRGG DGVDTVDYSQ TGAHAGIAAG
1381   RIGLGILADL GAGRVDKLGE AGSSAYDTVS GIENVVGTEL ADRITGDAQA NVLRGAGGAD
1441   VLAGGEGDDV LLGGDGDDQL SGDAGRDRLY GEAGDDWFFQ DAANAGNLLD GGDGRDTVDF
1501   SGPGRGLDAG AKGVFLSLGK GFASLMDEPE TSNVLRNIEN AVGSARDDVL IGDAGANVLN
1561   GLAGNDVLSG GAGDDVLLGD EGSDLLSGDA GNDDLFGGQG DDTYLFGVGY GHDTIYESGG
1621   GHDTIRINAG ADQLWFARQG NDLEIRILGT DDALTVHDWY RDADHRVEII HAANQAVDQA
1681   GIEKLVEAMA QYPDPGAAAA APPAARVPDT LMQSLAVNWR
```

Figure 9

```
CGGAAGAGCGCCCAATACGCAAACCGCCTCTCCCCGCGCGTTGGCCGATTCATTAATGCA
GCTGGCACGACAGGTTTCCCGACTGGAAAGCGGGCAGTGAGCGCAACGCAATTAATGTGA
GTTAGCTCACTCATTAGGCACCCCAGGCTTTACACTTTATGCTTCCGGCTCGTATGTTGT
GTGGAATTGTGAGCGGATAACAATTTCACACAGGAAACAGCTATGACCATGATTACGAAT
TTAATACGACTCACTATAGGGAAAGCTCTAGAAATAATTTTGTTTAACTTTAAGAAGGAG
ATATACATATGCTTCCGTCCGCCCAAGCGCCCTCCCTCCTCAATCCCACCGACGACTTCG
CGGCACTGGGCAATATTGCCTGGCTGTGGATGAACTCTCCCATGCACCGCGACTGGCCGG
TGCATCTGCTCGCACGCAACACGCTCGCGCCGATTCAACTGGGCCAATACATTCTGCTGC
GATGCAATGACGTGCCGGTTGCATACTGCAGCTGGGCCCTAATGGACGCCGACACCGAAC
TCTCCTATGTCATGGCGCCCTCGTCGCTGGGCGGGAATGCCTGGAACTGCGGCGACCGAC
TGTGGATCATCGACTGGATCGCGCCATTCTCGCGCGACGACAATCGTGCGCTGCGCCGCG
CGCTGGCCGAACGGCACCCCGACAGCGTGGGCCGTTCGCTGCGCGTTCGGCGCGGCGGCG
ACACCGCGCGCGTCAAGGAGTACCGAGGCCGCGCGCTGGACGCGGCCGCCACTCGCGCGC
AGCTGGACCGCTACCATGCCGAACTGATCGCAGGACTGCGCGCGAGCAACGGCGGATACG
CGCCGCGAGGCCGGGGCACCGCCTAAGGATCCTCTAGAGCTTGCATGCCCTGGCACGACA
GGTTTCCCGACTGGAAAGCGGGCAGTGAGCGCAACGCAATTAATGTGAGTTAGCTCACTC
ATTAGGCACCCCAGGCTTTACACTTTATGCTTCCGGCTCGTATGTTGTGTGGAATTGTGA
GCGGATAACAATTTCACACAGGAAACAGCTATGACCATGCAGCAATCGCATCAGGCTGGT
TACGCAAACGCCGCCGACCGGGAGTCTGGCATCCCCGCAGCCGTACTCGATGGCATCAAG
GCCGTGGCGAAGGAAAAAAACGCCACATTGATGTTCCGCCTGGTCAACCCCATTCCACC
AGCCTGATTGCCGAAGGGGTGGCCACCAAAGGATTGGGCGTGCACGCCAAGTCGTCCGAT
TGGGGGTTGCAGGCGGGCTACATTCCCGTCAACCCGAATCTTTCCAAACTGTTCGGCCGT
GCGCCCGAGGTGATCGCGCGGGCCGACAACGACGTCAACAGCAGCCTGGCGCATGGCCAT
ACCGCGGTCGACCTGACGCTGTCGAAAGAGCGGCTTGACTATCTGCGGCAAGCGGGCCTG
GTCACCGGCATGGCCGATGGCGTGGTCGCGAGCAACCACGCAGGCTACGAGCAGTTCGAG
TTTCGCGTGAAGGAAACCTCGGACGGGCGCTATGCCGTGCAGTATCGCCGCAAGGGCGGC
GACGATTTCGAGGCGGTCAAGGTGATCGGCAATGCCGCCGGTATTCCACTGACGGCGGAT
GGATCCATCGACATGTTCGCCATTATGCCGCATCTGTCCAACTTCCGCGACTCGGCGCGC
AGTTCGGTGACCAGCGGCGATTCGGTGACCGATTACCTGGCGCGCACGCGGCGGGCCGCC
AGCGAGGCCACGGGCGGTGTACACCTGGATCGCGAACGCATCGACTTGTTGTGGAAAATC
GCTCGCGCCGGCGCCCGTTCCGCAGTGGGCACCGAGGCGCGTCGCCAGTTCCGCTACGAC
GGCGACATGAATATCGGCGTGATCACCGATTTCGAGCTGGAAGTGCGCAATGCGCTGAAC
AGGCGGGCGCACGCCGTCGGCGCGCAGGACGTGGTCCAGCATGGCACTGAGCAGAACAAT
CCTTTCCCGGAGGCAGATGAGAAGATTTTCGTCGTATCGGCCACCGGTGAAAGCCAGATG
CTCACGCGCGGGCAACTGAAGGAATACATTGGCCAGCAGCGCGGCGAGGGCTATGTCTTC
TACGAGAACCGTGCATACGGCGTGGCGGGAAAAGCCTGTTCGACGATGGGCTGGGAGCC
GCGCCCGGCGTGCCGAGCGGACGTTCGAAGTTCTCGCCGGATGTACTGGAAACGGTGCCG
GCGTCACCCGGATTGCGGCGGCCGTCGCTGGGCGCAGTGGAACGCCAGGATTCCGGCTAT
GACAGCCTTGATGGGGTGGGATCGCGATCGTTCTCGTTGGGCGAGGTGTCCGACATGGCC
GCCGTGGAAGCGGCGGAACTGGAAATGACCCGGCAAGTCTTGCACGCCGGGGCGCGGCAG
GACGATGCCGAGCCGGGCGTGAGCGGTGCGTCGGCGCACTGGGGCAGCGGGCGCTGCAG
GGCGCCCAGGCGGTGGCGGCGGCGCAGCGGCTGGTTCATGCCATTGCCCTGATGACGCAA
TTCGGCCGGGCCGGTTCCACCAACACGCCGCAGGAAGCGGCCTCGTTGTCGGCGGCCGTG
TTCGGCTTGGGCGAGGCCAGCAGCGCCGTGGCCGAAACCGTGAGCGGTTTTTTCCGCGGG
TCTTCGCGCTGGGCCGGCGGTTTCGGCGTGGCTGGCGGCGCGATGGCGCTGGGAGGCGGC
ATCGCCGCGGCCGTTGGCGCCGGGATGTCGTTGACCGATGACGCGCCGGCCGGACAGAAG
GCCGCCGCCGGAGCTCCGATCGCGCTGCAGTTAACGGGTGGAACGGTCGAGCTGGCTTCT
TCCATCGCGTTGGCGCTGGCCGCGGCGCGCGGCGTGACCAGCGGCTTGCAGGTGGCCGGG
GCGTCGGCCGGGGCGGCTGCCGGCGCATTGGCCGCGGCGCTCAGTCCCATGGAGATCTAC
GGCCTGGTGCAGCAATCGCACTATGCGGATCAGCTGGACAAGCTGGCGCAGGAATCGAGC
GCATACGGTTACGAGGGCGACGCCTTGCTGGCCCAGCTGTATCGCGACAAGACGGCCGCC
GAGGGCGCCGTCGCCGGCGTCTCCGCCGTCCTGAGCACGGTGGGGGCGGCGGTGTCGATC
GCCGCGGCGGCCAGCGTGGTAGGGGCCCCGGTGGCGGTGGTCACTTCCTTGCTGACCGGG
```

Figure 11

```
GCTCTCAACGGCATCCTGCGCGGCGTGCAGCAGCCCATCATCGAAAAGCTGGCCAACGAT
TACGCTCGCAAGATCGACGAGCTGGGCGGGCCGCAAGCGTACTTCGAGAAAAACCTGCAG
GCGCGTCACGAACAACTGGCCAATTCGGACGGCCTACGGAAAATGCTGGCCGACCTGCAG
GCCGGTTGGAACGCCAGCAGCGTGATCGGGGTGCAGACGACAGAGATCTCCAAGTCGGCG
CTCGAACTGGCCGCCATTACCGGCAACGCGGACAACCTGAAATCCGTCGACGTGTTCGTG
GACCGCTTCGTCCAGGGCGAGCGGGTGGCCGGCCAGCCGGTGGTCCTCGACGTCGCCGCC
GGCGGCATCGATATCGCCAGCCGCAAGGGCGAGCGGCCGGCGCTGACGTTCATCACGCCG
CTGGCCGCGCCAGGAGAAGAGCAGCGCCGGCGCACGAAAACGGGCAGATCTGAATTCACC
ACATTCGTCGAGATCGTGGGCAAGCAGGACCGCTGGCGCATCCGGGACGGCGCGGCCGAC
ACCACCATCGATCTGGCCAAGGTGGTGTCGCAACTGGTCGACGCCAATGGCGTGCTCAAG
CACAGCATCAAACTGGATGTGATCGGCGGAGATGGCGATGACGTCGTGCTTGCCAATGCT
TCGCGCATCCATTATGACGGCGGCGCGGGCACCAACACGGTCAGCTATGCCGCCCTGGGT
CGACAGGATTCCATTACCGTGTCCGCCGACGGGGAACGTTTCAACGTGCGCAAGCAGTTG
AACAACGCCAACGTGTATCGCGAAGGCGTGGCTACCCAGACAACCGCCTACGGCAAGCGC
ACGGAGAATGTCCAATACCGCCATGTCGAGCTGGCCCGTGTCGGGCAAGTGGTGGAGGTC
GACACGCTCAGCATGTGCAGCACATCATCGGCGGGCCGGCAACGATTCGATCACCGGC
AATGCGCACGACAACTTCCTAGCCGGCGGGTCGGGCGACGACAGGCTGGATGGCGGCGCC
GGCAACGACACCCTGGTTGGCGGCGAGGGCCAAAACACGGTCATCGGCGGCGCCGGCGAC
GACGTATTCCTGCAGGACCTGGGGGTATGGAGCAACCAGCTCGATGGCGGCGCGGGCGTC
GATACCGTGAAGTACAACGTGCACCAGCCTTCCGAGGAGCGCCTCGAACGCATGGGCGAC
ACGGGCATCCATGCCGATCTTCAAAAGGGCACGGTCGAGAAGTGGCCGGCCCTGAACCTG
TTCAGCGTCGACCATGTCAAGAATATCGAGAATCTGCACGGCTCCCGCCTAAACGACCGC
ATCGCCGGCGACGACCAGGACAACGAGCTCTGGGCCACGATGGCAACGACACGATACGC
GGCCGGGGCGGCGACGACATCCTGCGCGGCGGCCTGGGCCTGGACACGCTGTATGGCGAG
GACGGCAACGACATCTTCCTGCAGGACGACGAGACCGTCAGCGATGACATCGACGGCGGC
GCGGGGCTGGACACCGTCGACTACTCCGCCATGATCCATCCAGGCAGGATCGTTGCGCCG
CATGAATACGGCTTCGGGATCGAGGCGGACCTGTCCAGGGAATGGGTGCGCAAGGCGTCC
GCGCTGGGCGTGGACTATTACGATAATGTCCGCAATGTCGAAAACGTCATCGGTACGAGC
ATGAAGGATGTGCTCATCGGCGACGCGCAAGCCAATACCCTGATGGGCCAGGGCGGCGAC
GATACCGTGCGCGGCGGCGACGGCGATGATCTGCTGTTCGGCGGCGACGGCAACGACATG
CTGTATGGCGACGCCGGCAACGACACCCTCTACGGGGGGCTGGGCGACGATACCCTTGAA
GGCGGCGCGGGCAACGATTGGTTCGGCCAGACGCAGGCGCGCGAGCATGACGTGCTGCGC
GGCGGAGATGGGGTGGATACCGTCGATTACAGCCAGACCGGCGCGCATGCCGGCATTGCC
GCGGGTCGCATCGGGCTGGGCATCCTGGCTGACCTGGGCGCCGGCCGCGTCGACAAGCTG
GGCGAGGCCGGCAGCAGCGCCTACGATACGGTTTCCGGTATCGAGAACGTGGTGGGCACG
GAACTGGCCGACCGCATCACGGGCGATGCGCAGGCCAACGTGCTGCGCGGCGCGGGTGGC
GCCGACGTGCTTGCGGGCGGCGAGGGCGACGATGTGCTGCTGGGCGGCGACGGCGACGAC
CAGCTGTCGGGCGACGCCGGACGCGATCGCTTGTACGGCGAAGCCGGTGACGACTGGTTC
TTCCAGGATGCCGCCAATGCCGGCAATCTGCTCGACGGCGGCGACGGCCGCGATACCGTG
GATTTCAGCGGCCCGGGCCGGGGCCTCGACGCCGGCGCAAAGGGCGTATTCCTGAGCTTG
GGCAAGGGGTTCGCCAGCCTGATGGACGAACCCGAAACCAGCAACGTGTTGCGCAATATC
GAGAACGCCGTGGGCAGCGCGCGTGATGACGTGCTGATCGGCGACGCAGGCGCCAACGTC
CTCAATGGCCTGGCGGGCAACGACGTGCTGTCCGGCGGCGCTGGCGACGATGTGCTGCTG
GGCGACGAGGGCTCGGACCTGCTCAGCGGCGATGCGGGCAACGACGATCTGTTCGGCGGG
CAGGGCGATGATACTTATCTGTTCGGGGTCGGGTACGGGCACGACACGATCTACGAATCG
GGCGGCGGCCATGACACCATCCGCATCAACGCGGGGCGGACCAGCTGTGGTTCGCGCGC
CAGGGCAACGACCTGGAGATCCGCATTCTCGGCACCGACGATGCACTTACCGTGCACGAC
TGGTATCGCGACGCCGATCACCGGGTGGAAATCATCCATGCCGCCAACCAGGCGGTAGAC
CAGGCAGGCATCGAAAAGCTGGTCGAGGCAATGGCGCAGTATCCGGACCCCGGCGCGGCG
GCGGCTGCCCCGCCGGCGGCGCGCGTGCCGGACACGCTGATGCAGTCCCTGGCTGTCAAC
TGGCGCTGAAGCGCCGTGAATCACGGCCCGCCTGCCTCGCGCGGCGGCGCCGTCTCTTTG
CGTTCTTCTCCGAGGTATTTCCCATCATGAATTCACTGGCCGTCGTTTTACAACGTCGTG
ACTGGGAAAACCCTGGCGTTACCCAACTTAATCGCCTTGCAGCACATCCCCCTTTCGCCA
```

Figure 11
(continued)

```
GCTGGCGTAATAGCGAAGAGGCCCGCACCGATCGCCCTTCCCAACAGTTGCGCAGCCTGA
ATGGCGAATGGGAAATTGTAAACGTTAATATTTTGTTAATATTTTGTTAAAATTCGCGTT
AAATTTTTGTTAAATCAGCTCATTTTTTAACCAATAGGCCGAAATCGGCAAAATCCCTTA
TAAATCAAAAGAATAGACCGAGATAGGGTTGAGTGTTGTTCCAGTTTGGAACAAGAGTCC
ACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACT
AAATCGGAACCCTAAAGGGATGCCCCGATTTAGAGCTTGACGGGGAAAGCCGGCGAACGT
GGCGAGAAAGGAAGGGAAGAAAGCGAAAGGAGCGGGCGCTAGGGCGCTGGCAAGTGTAGC
GGTCACGCTGCGCGTAACCACCACACCCGCCGCGCTTAATGCGCCGCTACAGGGCGCGTC
AGGTGGCACTTTTCGGGGAAATGTGCGCGGAACCCCTATTTGTTTATTTTTCTAAATACA
TTCAAATATGTATCCGCTCATGAGACAATAACCCTGATAAATGCTTCAATAATATTGAAA
AAGGAAGAGTATGAGTATTCAACATTTCCGTGTCGCCCTTATTCCCTTTTTTGCGGCATT
TTGCCTTCCTGTTTTTGCTCACCCAGAAACGCTGGTGAAAGTAAAAGATGCTGAAGATCA
GTTGGGTGCACGAGTGGGTTACATCGAACTGGATCTCAACAGCGGTAAGATCCTTGAGAG
TTTTCGCCCCGAAGAACGTTTTCCAATGATGAGCACTTTTAAAGTTCTGCTATGTGGCGC
GGTATTATCCCGTATTGACGCCGGGCAAGAGCAACTCGGTCGCCGCATACACTATTCTCA
GAATGACTTGGTTGAGTACTCACCAGTCACAGAAAAGCATCTTACGGATGGCATGACAGT
AAGAGAATTATGCAGTGCTGCCATAACCATGAGTGATAACACTGCGGCCAACTTACTTCT
GACAACGATCGGAGGACCGAAGGAGCTAACCGCTTTTTTGCACAACATGGGGGATCATGT
AACTCGCCTTGATCGTTGGGAACCGGAGCTGAATGAAGCCATACCAAACGACGAGCGTGA
CACCACGATGCCTGTAGCAATGGCAACAACGTTGCGCAAACTATTAACTGGCGAACTACT
TACTCTAGCTTCCCGGCAACAATTAATAGACTGGATGGAGGCGGATAAAGTTGCAGGACC
ACTTCTGCGCTCGGCCCTTCCGGCTGGCTGGTTTATTGCTGATAAATCTGGAGCCGGTGA
GCGTGGGTCTCGCGGTATCATTGCAGCACTGGGGCCAGATGGTAAGCCCTCCCGTATCGT
AGTTATCTACACGACGGGGAGTCAGGCAACTATGGATGAACGAAATAGACAGATCGCTGA
GATAGGTGCCTCACTGATTAAGCATTGGTAACTGTCAGACCAAGTTTACTCATATATACT
TTAGATTGATTTAAAACTTCATTTTTAATTTAAAAGGATCTAGGTGAAGATCCTTTTTGA
TAATCTCATGACCAAAATCCCTTAACGTGAGTTTTCGTTCCACTGAGCGTCAGACCCCGT
AGAAAAGATCAAAGGATCTTCTTGAGATCCTTTTTTTCTGCGCGTAATCTGCTGCTTGCA
ACAAAAAAACCACCGCTACCAGCGGTGGTTTGTTTGCCGGATCAAGAGCTACCAACTCT
TTTTCCGAAGGTAACTGGCTTCAGCAGAGCGCAGATACCAAATACTGTCCTTCTAGTGTA
GCCGTAGTTAGGCCACCACTTCAAGAACTCTGTAGCACCGCCTACATACCTCGCTCTGCT
AATCCTGTTACCAGTGGCTGCTGCCAGTGGCGATAAGTCGTGTCTTACCGGGTTGGACTC
AAGACGATAGTTACCGGATAAGGCGCAGCGGTCGGGCTGAACGGGGGGTTCGTGCACACA
GCCCAGCTTGGAGCGAACGACCTACACCGAACTGAGATACCTACAGCGTGAGCTATGAGA
AAGCGCCACGCTTCCCGAAGGGAGAAAGGCGGACAGGTATCCGGTAAGCGGCAGGGTCGG
AACAGGAGAGCGCACGAGGGAGCTTCCAGGGGAAACGCCTGGTATCTTTATAGTCCTGT
CGGGTTTCGCCACCTCTGACTTGAGCGTCGATTTTTGTGATGCTCGTCAGGGGGCGGAG
CCTATGGAAAAACGCCAGCAACGCGGCCTTTTTACGGTTCCTGGCCTTTTGCTGGCCTTT
TGCTCACATGTTCTTTCCTGCGTTATCCCTGATTCTGTGGATAACCGTATTACCGCCTT
TGAGTGAGCTGATACCGCTCGCCGCAGCCGAACGACCGAGCGCAGCGAGTCAGTGAGCGA
GGAAG
```

Figure 11
(continued)

```
CGGAAGAGCGCCCAATACGCAAACCGCCTCTCCCCGCGCGTTGGCCGATTCATTAATGCA
GCTGGCACGACAGGTTTCCCGACTGGAAAGCGGGCAGTGAGCGCAACGCAATTAATGTGA
GTTAGCTCACTCATTAGGCACCCCAGGCTTTACACTTTATGCTTCCGGCTCGTATGTTGT
GTGGAATTGTGAGCGGATAACAATTTCACACAGGAAACAGCTATGACCATGATTACGAAT
TAATACGACTCACTATAGGGAAAGCTCTAGAAATAATTTTGTTTAACTTTAAGAAGGAG
ATATACATATGCTTCCGTCCGCCCAAGCGCCCTCCCTCCTCAATCCCACCGACGACTTCG
CGGCACTGGGCAATATTGCCTGGCTGTGGATGAACTCTCCCATGCACCGCGACTGGCCGG
TGCATCTGCTCGCACGCAACACGCTCGCGCCGATTCAACTGGGCCAATACATTCTGCTGC
GATGCAATGACGTGCCGGTTGCATACTGCAGCTGGGCCCTAATGGACGCCGACACCGAAC
TCTCCTATGTCATGGCGCCCTCGTCGCTGGGCGGGAATGCCTGGAACTGCGGCGACCGAC
TGTGGATCATCGACTGGATCGCGCCATTCTCGCGCGACGACAATCGTGCGCTGCGCCGCG
CGCTGGCCGAACGGCACCCCGACAGCGTGGGCCGTTCGCTGCGCGTTCGGCGCGGCGGCG
ACACCGCGCGCGTCAAGGAGTACCGAGGCCGCGCGCTGGACGCGGCCGCCACTCGCGCGC
AGCTGGACCGCTACCATGCCGAACTGATCGCAGGACTGCGCGCGAGCAACGGCGGATACG
CGCCGCGAGGCCGGGGCACCGCCTAAGGATCCTCTAGAGCTTGCATGCCCTGGCACGACA
GGTTTCCCGACTGGAAAGCGGGCAGTGAGCGCAACGCAATTAATGTGAGTTAGCTCACTC
ATTAGGCACCCCAGGCTTTACACTTTATGCTTCCGGCTCGTATGTTGTGTGGAATTGTGA
GCGGATAACAATTTCACACAGGAAACAGCTATGACCATGCAGCAATCGCATCAGGCTGGT
TACGCAAACGCCGCCGACCGGGAGTCTGGCATCCCCGCAGCCGTACTCGATGGCATCAAG
GCCGTGGCGAAGGAAAAAAACGCCACATTGATGTTCCGCCTGGTCAACCCCCATTCCACC
AGCCTGATTGCCGAAGGGGTGGCCACCAAAGGATTGGGCGTGCACGCCAAGTCGTCCGAT
TGGGGGTTGCAGGCGGGCTACATTCCCGTCAACCCGAATCTTTCCAAACTGTTCGGCCGT
GCGCCCGAGGTGATCGCGCGGGCCGACAACGACGTCAACAGCAGCCTGGCGCATGGCCAT
ACCGCGGTCGACCTGACGCTGTCGAAAGAGCGGCTTGACTATCTGCGGCAAGCGGGCCTG
GTCACCGGCATGGCCGATGGCGTGGTCGCGAGCAACCACGCAGGCTACGAGCAGTTCGAG
TTTCGCGTGAAGGAAACCTCGGACGGGCGCTATGCCGTGCAGTATCGCCGCAAGGGCGGC
GACGATTTCGAGGCGGTCAAGGTGATCGGCAATGCCGCCGGTATTCCACTGACGGCGGAT
GGATCCATCGACATGTTCGCCATTATGCCGCATCTGTCCAACTTCCGCGACTCGGCGCGC
AGTTCGGTGACCAGCGGCGATTCGGTGACCGATTACCTGGCGCGCACGCGGCGGGCCGCC
AGCGAGGCCACGGGCGGTGTACTCTCAATAATTAATTTCGAAAAGCTTGTACACCTGGAT
CGCGAACGCATCGACTTGTTGTGGAAAATCGCTCGCGCCGGCGCCCGTTCCGCAGTGGGC
ACCGAGGCGCGTCGCCAGTTCCGCTACGACGGCGACATGAATATCGGCGTGATCACCGAT
TTCGAGCTGGAAGTGCGCAATGCGCTGAACAGGCGGGCGCACGCCGTCGGCGCGCAGGAC
GTGGTCCAGCATGGCACTGAGCAGAACAATCCTTTCCCGGAGGCAGATGAGAAGATTTTC
GTCGTATCGGCCACCGGTGAAAGCCAGATGCTCACGCGCGGGCAACTGAAGGAATACATT
GGCCAGCAGCGCGGCGAGGGCTATGTCTTCTACGAGAACCGTGCATACGGCGTGGCGGGG
AAAAGCCTGTTCGACGATGGGCTGGAGCCGCGCCCGGCGTGCCGAGCGGACGTTCGAAG
TTCTCGCCGGATGTACTGGAAACGGTGCCGGCGTCACCCGGATTGCGGCGGCCGTCGCTG
GGCGCAGTGGAACGCCAGGATTCCGGCTATGACAGCCTTGATGGGGTGGGATCGCGATCG
TTCTCGTTGGGCGAGGTGTCCGACATGGCCGCCGTGGAAGCGGCGGAACTGGAAATGACC
CGGCAAGTCTTGCACGCCGGGCGCGGCAGGACGATGCCGAGCCGGGCGTGAGCGGTGCG
TCGGCGCACTGGGGGCAGCGGGCGCTGCAGGGCGCCCAGGCGGTGGCGGCGGCGCAGCGG
CTGGTTCATGCCATTGCCCTGATGACGCAATTCGGCCGGGCCGGTTCCACCAACACGCCG
CAGGAAGCGGCCTCGTTGTCGGCGGCCGTGTTCGGCTTGGGCGAGGCCAGCAGCGCCGTG
GCCGAAACCGTGAGCGGTTTTTTCCGCGGGTCTTCGCGCTGGGCCGGCGGTTTCGGCGTG
GCTGGCGGCGCGATGGCGCTGGAGGCGGCATCGCCGCGGCCGTTGGCGCCGGGATGTCG
TTGACCGATGACGCGCCGGCCGGACAGAAGGCCGCCGCCGGAGCTCCGATCGCGCTGCAG
TTAACGGGTGGAACGGTCGAGCTGGCTTCTTCCATCGCGTTGGCGCTGGCCGCGGCGCGC
GGCGTGACCAGCGGCTTGCAGGTGGCCGGGGCGTCGGCCGGGGCGGCTGCCGGCGCATTG
GCCGCGGCGCTCAGTCCCATGGAGATCTACGGCCTGGTGCAGCAATCGCACTATGCGGAT
CAGCTGGACAAGCTGGCGCAGGAATCGAGCGCATACGGTTACGAGGGCGACGCCTTGCTG
GCCCAGCTGTATCGCGACAAGACGGCCGCCGAGGGCGCCGTCGCCGGCGTCTCCGCCGTC
```

Figure 13

```
CTGAGCACGGTGGGGCGGCGGTGTCGATCGCCGCGGCGGCCAGCGTGGTAGGGGCCCCG
GTGGCGGTGGTCACTTCCTTGCTGACCGGGGCTCTCAACGGCATCCTGCGCGGCGTGCAG
CAGCCCATCATCGAAAAGCTGGCCAACGATTACGCTCGCAAGATCGACGAGCTGGGCGGG
CCGCAAGCGTACTTCGAGAAAAACCTGCAGGCGCGTCACGAACAACTGGCCAATTCGGAC
GGCCTACGGAAAATGCTGGCCGACCTGCAGGCCGGTTGGAACGCCAGCAGCGTGATCGGG
GTGCAGACGACAGAGATCTCCAAGTCGGCGCTCGAACTGGCCGCCATTACCGGCAACGCG
GACAACCTGAAATCCGTCGACGTGTTCGTGGACCGCTTCGTCCAGGGCGAGCGGGTGGCC
GGCCAGCCGGTGGTCCTCGACGTCGCCGCCGGCGGCATCGATATCGCCAGCCGCAAGGGC
GAGCGGCCGGCGCTGACGTTCATCACGCCGCTGGCCGCGCCAGGAGAAGAGCAGCGCCGG
CGCACGAAAACGGGCAGATCTGAATTCACCACATTCGTCGAGATCGTGGGCAAGCAGGAC
CGCTGGCGCATCCGGGACGGCGCGGCCGACACCACCATCGATCTGGCCAAGGTGGTGTCG
CAACTGGTCGACGCCAATGGCGTGCTCAAGCACAGCATCAAACTGGATGTGATCGGCGGA
GATGGCGATGACGTCGTGCTTGCCAATGCTTCGCGCATCCATTATGACGGCGGCGCGGGC
ACCAACACGGTCAGCTATGCCGCCCTGGGTCGACAGGATTCCATTACCGTGTCCGCCGAC
GGGGAACGTTTCAACGTGCGCAAGCAGTTGAACAACGCCAACGTGTATCGCGAAGGCGTG
GCTACCCAGACAACCGCCTACGGCAAGCGCACGGAGAATGTCCAATACCGCCATGTCGAG
CTGGCCCGTGTCGGGCAAGTGGTGGAGGTCGACACGCTCGAGCATGTGCAGCACATCATC
GGCGGGGCCGGCAACGATTCGATCACCGGCAATGCGCACGACAACTTCCTAGCCGGCGGG
TCGGGCGACGACAGGCTGGATGGCGGCGCCGGCAACGACACCCTGGTTGGCGGCGAGGGC
CAAAACACGGTCATCGGCGGCGCCGGCGACGACGTATTCCTGCAGGACCTGGGGGTATGG
AGCAACCAGCTCGATGGCGGCGCGGGCGTCGATACCGTGAAGTACAACGTGCACCAGCCT
TCCGAGGAGCGCCTCGAACGCATGGGCGACACGGGCATCCATGCCGATCTTCAAAAGGGC
ACGGTCGAGAAGTGGCCGGCCCTGAACCTGTTCAGCGTCGACCATGTCAAGAATATCGAG
AATCTGCACGGCTCCCGCCTAAACGACCGCATCGCCGGCGACGACCAGGACAACGAGCTC
TGGGGCCACGATGGCAACGACACGATACGCGGCCGGGGCGGCGACGACATCCTGCGCGGC
GGCCTGGGCCTGGACACGCTGTATGGCGAGGACGGCAACGACATCTTCCTGCAGGACGAC
GAGACCGTCAGCGATGACATCGACGGCGGCGCGGGGCTGGACACCGTCGACTACTCCGCC
ATGATCCATCCAGGCAGGATCGTTGCGCCGCATGAATACGGCTTCGGGATCGAGGCGGAC
CTGTCCAGGGAATGGGTGCGCAAGGCGTCCGCGCTGGGCGTGGACTATTACGATAATGTC
CGCAATGTCGAAAACGTCATCGGTACGAGCATGAAGGATGTGCTCATCGGCGACGCGCAA
GCCAATACCCTGATGGGCCAGGGCGGCGACGATACCGTGCGCGGCGGCGACGGCGATGAT
CTGCTGTTCGGCGGCGACGGCAACGACATGCTGTATGGCGACGCCGGCAACGACACCCTC
TACGGGGGGCTGGGCGACGATACCCTTGAAGGCGGCGCGGGCAACGATTGGTTCGGCCAG
ACGCAGGCGCGCGAGCATGACGTGCTGCGCGGCGGAGATGGGGTGGATACCGTCGATTAC
AGCCAGACCGGCGCGCATGCCGGCATTGCCGCGGGTCGCATCGGGCTGGGCATCCTGGCT
GACCTGGGCGCCGGCCGCGTCGACAAGCTGGGCGAGGCCGGCAGCAGCGCCTACGATACG
GTTTCCGGTATCGAGAACGTGGTGGGCACGGAACTGGCCGACCGCATCACGGGCGATGCG
CAGGCCAACGTGCTGCGCGGCGCGGGTGGCGCCGACGTGCTTGCGGGCGGCGAGGGCGAC
GATGTGCTGCTGGGCGGCGACGGCGACGACCAGCTGTCGGGCGACGCCGGACGCGATCGC
TTGTACGGCGAAGCCGGTGACGACTGGTTCTTCCAGGATGCCGCCAATGCCGGCAATCTG
CTCGACGGCGGCGACGGCCGCGATACCGTGGATTTCAGCGGCCCGGGCCGGGGCCTCGAC
GCCGGCGCAAAGGGCGTATTCCTGAGCTTGGGCAAGGGGTTCGCCAGCCTGATGGACGAA
CCCGAAACCAGCAACGTGTTGCGCAATATCGAGAACGCCGTGGGCAGCGCGCGTGATGAC
GTGCTGATCGGCGACGCAGGCGCCAACGTCCTAATGGCCTGGCGGGCAACGACGTGCTG
TCCGGCGGCGCTGGCGACGATGTGCTGCTGGGCGACGAGGGCTCGGACCTGCTCAGCGGC
GATGCGGGCAACGACGATCTGTTCGGCGGGCAGGGCGATGATACTTATCTGTTCGGGGTC
GGGTACGGGCACGACACGATCTACGAATCGGGCGGCGGCCATGACACCATCCGCATCAAC
GCGGGGGCGGACCAGCTGTGGTTCGCGCGCCAGGGCAACGACCTGGAGATCCGCATTCTC
GGCACCGACGATGCACTTACCGTGCACGACTGGTATCGCGACGCCGATCACCGGGTGGAA
ATCATCCATGCCGCCAACCAGGCGGTAGACCAGGCAGGCATCGAAAAGCTGGTCGAGGCA
ATGGCGCAGTATCCGGACCCCGGCGCGGCGGCGGCTGCCCCGCCGGCGGCGCGCGTGCCG
GACACGCTGATGCAGTCCCTGGCTGTCAACTGGCGCTGAAGCGCCGTGAATCACGGCCCG
CCTGCCTCGCGCGGCGGCGCCGTCTCTTTGCGTTCTTCTCCGAGGTATTTCCCATCATGA
```

Figure 13
(continued)

```
ATTCACTGGCCGTCGTTTTACAACGTCGTGACTGGGAAAACCCTGGCGTTACCCAACTTA
ATCGCCTTGCAGCACATCCCCCTTTCGCCAGCTGGCGTAATAGCGAAGAGGCCCGCACCG
ATCGCCCTTCCCAACAGTTGCGCAGCCTGAATGGCGAATGGGAAATTGTAAACGTTAATA
TTTTGTTAATATTTTGTTAAAATTCGCGTTAAATTTTTGTTAAATCAGCTCATTTTTTAA
CCAATAGGCCGAAATCGGCAAAATCCCTTATAAATCAAAAGAATAGACCGAGATAGGGTT
GAGTGTTGTTCCAGTTTGGAACAAGAGTCCACTATTAAAGAACGTGGACTCCAACGTCAA
AGGGCGAAAAACCGTCTATCAGGGCGATGGCCCACTACGTGAACCATCACCCTAATCAAG
TTTTTTGGGGTCGAGGTGCCGTAAAGCACTAAATCGGAACCCTAAAGGGATGCCCCGATT
TAGAGCTTGACGGGGAAAGCCGGCGAACGTGGCGAGAAAGGAAGGGAAGAAAGCGAAAGG
AGCGGGCGCTAGGGCGCTGGCAAGTGTAGCGGTCACGCTGCGCGTAACCACCACACCCGC
CGCGCTTAATGCGCCGCTACAGGGCGCGTCAGGTGGCACTTTTCGGGGAAATGTGCGCGG
AACCCCTATTTGTTTATTTTTCTAAATACATTCAAATATGTATCCGCTCATGAGACAATA
ACCCTGATAAATGCTTCAATAATATTGAAAAAGGAAGAGTATGAGTATTCAACATTTCCG
TGTCGCCCTTATTCCCTTTTTTGCGGCATTTTGCCTTCCTGTTTTTGCTCACCCAGAAAC
GCTGGTGAAAGTAAAAGATGCTGAAGATCAGTTGGGTGCACGAGTGGGTTACATCGAACT
GGATCTCAACAGCGGTAAGATCCTTGAGAGTTTTCGCCCCGAAGAACGTTTTCCAATGAT
GAGCACTTTTAAAGTTCTGCTATGTGGCGCGGTATTATCCCGTATTGACGCCGGGCAAGA
GCAACTCGGTCGCCGCATACACTATTCTCAGAATGACTTGGTTGAGTACTCACCAGTCAC
AGAAAAGCATCTTACGGATGGCATGACAGTAAGAGAATTATGCAGTGCTGCCATAACCAT
GAGTGATAACACTGCGGCCAACTTACTTCTGACAACGATCGGAGGACCGAAGGAGCTAAC
CGCTTTTTTGCACAACATGGGGGATCATGTAACTCGCCTTGATCGTTGGGAACCGGAGCT
GAATGAAGCCATACCAAACGACGAGCGTGACACCACGATGCCTGTAGCAATGGCAACAAC
GTTGCGCAAACTATTAACTGGCGAACTACTTACTCTAGCTTCCCGGCAACAATTAATAGA
CTGGATGGAGGCGGATAAAGTTGCAGGACCACTTCTGCGCTCGGCCCTTCCGGCTGGCTG
GTTTATTGCTGATAAATCTGGAGCCGGTGAGCGTGGGTCTCGCGGTATCATTGCAGCACT
GGGGCCAGATGGTAAGCCCTCCCGTATCGTAGTTATCTACACGACGGGGAGTCAGGCAAC
TATGGATGAACGAAATAGACAGATCGCTGAGATAGGTGCCTCACTGATTAAGCATTGGTA
ACTGTCAGACCAAGTTTACTCATATATACTTTAGATTGATTTAAAACTTCATTTTTAATT
TAAAAGGATCTAGGTGAAGATCCTTTTTGATAATCTCATGACCAAAATCCCTTAACGTGA
GTTTTCGTTCCACTGAGCGTCAGACCCCGTAGAAAAGATCAAAGGATCTTCTTGAGATCC
TTTTTTTCTGCGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCTTCAGCAGAGC
GCAGATACCAAATACTGTCCTTCTAGTGTAGCCGTAGTTAGGCCACCACTTCAAGAACTC
TGTAGCACCGCCTACATACCTCGCTCTGCTAATCCTGTTACCAGTGGCTGCTGCCAGTGG
CGATAAGTCGTGTCTTACCGGGTTGGACTCAAGACGATAGTTACCGGATAAGGCGCAGCG
GTCGGGCTGAACGGGGGGTTCGTGCACACAGCCCAGCTTGGAGCGAACGACCTACACCGA
ACTGAGATACCTACAGCGTGAGCTATGAGAAAGCGCCACGCTTCCCGAAGGGAGAAAGGC
GGACAGGTATCCGGTAAGCGGCAGGGTCGGAACAGGAGAGCGCACGAGGGAGCTTCCAGG
GGGAAACGCCTGGTATCTTTATAGTCCTGTCGGGTTTCGCCACCTCTGACTTGAGCGTCG
ATTTTTGTGATGCTCGTCAGGGGGCGGAGCCTATGGAAAAACGCCAGCAACGCGGCCTT
TTTACGGTTCCTGGCCTTTTGCTGGCCTTTTGCTCACATGTTCTTTCCTGCGTTATCCCC
TGATTCTGTGGATAACCGTATTACCGCCTTTGAGTGAGCTGATACCGCTCGCCGCAGCCG
AACGACCGAGCGCAGCGAGTCAGTGAGCGAGGAAG
```

Figure 13
(continued)

SEQUENCE LISTING

<160> NUMBER OF SEQ ID NOS: 12

<210> SEQ ID NO 1
<211> LENGTH: 1706
<212> TYPE: PRT
<213> ORGANISM: Bordetella pertussis

<400> SEQUENCE: 1

```
Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
```

```
              130                 135                 140
Glu Gln Phe Glu Phe Arg Val Lys Glu Thr Ser Asp Gly Arg Tyr Ala
145                 150                 155                 160

Val Gln Tyr Arg Arg Lys Gly Gly Asp Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
                260                 265                 270

Thr Asp Phe Glu Leu Glu Val Arg Asn Ala Leu Asn Arg Arg Ala His
            275                 280                 285

Ala Val Gly Ala Gln Asp Val Val Gln His Gly Thr Glu Gln Asn Asn
        290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
                340                 345                 350

Ala Gly Lys Ser Leu Phe Asp Asp Gly Leu Gly Ala Ala Pro Gly Val
            355                 360                 365

Pro Ser Gly Arg Ser Lys Phe Ser Pro Asp Val Leu Glu Thr Val Pro
        370                 375                 380

Ala Ser Pro Gly Leu Arg Arg Pro Ser Leu Gly Ala Val Glu Arg Gln
385                 390                 395                 400

Asp Ser Gly Tyr Asp Ser Leu Asp Gly Val Gly Ser Arg Ser Phe Ser
                405                 410                 415

Leu Gly Glu Val Ser Asp Met Ala Ala Val Glu Ala Ala Glu Leu Glu
                420                 425                 430

Met Thr Arg Gln Val Leu His Ala Gly Ala Arg Gln Asp Asp Ala Glu
            435                 440                 445

Pro Gly Val Ser Gly Ala Ser Ala His Trp Gly Gln Arg Ala Leu Gln
        450                 455                 460

Gly Ala Gln Ala Val Ala Ala Gln Arg Leu Val His Ala Ile Ala
465                 470                 475                 480

Leu Met Thr Gln Phe Gly Arg Ala Gly Ser Thr Asn Thr Pro Gln Glu
                485                 490                 495

Ala Ala Ser Leu Ser Ala Ala Val Phe Gly Leu Gly Glu Ala Ser Ser
            500                 505                 510

Ala Val Ala Glu Thr Val Ser Gly Phe Phe Arg Gly Ser Ser Arg Trp
        515                 520                 525

Ala Gly Gly Phe Gly Val Ala Gly Gly Ala Met Ala Leu Gly Gly Gly
    530                 535                 540

Ile Ala Ala Ala Val Gly Ala Gly Met Ser Leu Thr Asp Asp Ala Pro
545                 550                 555                 560
```

```
Ala Gly Gln Lys Ala Ala Gly Ala Glu Ile Ala Leu Gln Leu Thr
            565                 570                 575
Gly Gly Thr Val Glu Leu Ala Ser Ser Ile Ala Leu Ala Leu Ala Ala
        580                 585                 590
Ala Arg Gly Val Thr Ser Gly Leu Gln Val Ala Gly Ala Ser Ala Gly
        595                 600                 605
Ala Ala Ala Gly Ala Leu Ala Ala Leu Ser Pro Met Glu Ile Tyr
        610                 615                 620
Gly Leu Val Gln Gln Ser His Tyr Ala Asp Gln Leu Asp Lys Leu Ala
625                 630                 635                 640
Gln Glu Ser Ser Ala Tyr Gly Tyr Glu Gly Asp Ala Leu Leu Ala Gln
            645                 650                 655
Leu Tyr Arg Asp Lys Thr Ala Ala Glu Gly Ala Val Ala Gly Val Ser
            660                 665                 670
Ala Val Leu Ser Thr Val Gly Ala Ala Val Ser Ile Ala Ala Ala Ala
            675                 680                 685
Ser Val Val Gly Ala Pro Val Ala Val Thr Ser Leu Leu Thr Gly
            690                 695                 700
Ala Leu Asn Gly Ile Leu Arg Gly Val Gln Gln Pro Ile Ile Glu Lys
705                 710                 715                 720
Leu Ala Asn Asp Tyr Ala Arg Lys Ile Asp Glu Leu Gly Gly Pro Gln
                725                 730                 735
Ala Tyr Phe Glu Lys Asn Leu Gln Ala Arg His Glu Gln Leu Ala Asn
                740                 745                 750
Ser Asp Gly Leu Arg Lys Met Leu Ala Asp Leu Gln Ala Gly Trp Asn
            755                 760                 765
Ala Ser Ser Val Ile Gly Val Gln Thr Thr Glu Ile Ser Lys Ser Ala
            770                 775                 780
Leu Glu Leu Ala Ala Ile Thr Gly Asn Ala Asp Asn Leu Lys Ser Val
785                 790                 795                 800
Asp Val Phe Val Asp Arg Phe Val Gln Gly Glu Arg Val Ala Gly Gln
                805                 810                 815
Pro Val Val Leu Asp Val Ala Gly Gly Ile Asp Ile Ala Ser Arg
            820                 825                 830
Lys Gly Glu Arg Pro Ala Leu Thr Phe Ile Thr Pro Leu Ala Ala Pro
            835                 840                 845
Gly Glu Glu Gln Arg Arg Thr Lys Thr Gly Lys Ser Glu Phe Thr
        850                 855                 860
Thr Phe Val Glu Ile Val Gly Lys Gln Asp Arg Trp Arg Ile Arg Asp
865                 870                 875                 880
Gly Ala Ala Asp Thr Thr Ile Asp Leu Ala Lys Val Val Ser Gln Leu
                885                 890                 895
Val Asp Ala Asn Gly Val Leu Lys His Ser Ile Lys Leu Asp Val Ile
                900                 905                 910
Gly Gly Asp Gly Asp Val Val Leu Ala Asn Ala Ser Arg Ile His
        915                 920                 925
Tyr Asp Gly Gly Ala Gly Thr Asn Thr Val Ser Tyr Ala Ala Leu Gly
        930                 935                 940
Arg Gln Asp Ser Ile Thr Val Ser Ala Asp Gly Glu Arg Phe Asn Val
945                 950                 955                 960
Arg Lys Gln Leu Asn Asn Ala Asn Val Tyr Arg Glu Gly Val Ala Thr
                965                 970                 975
Gln Thr Thr Ala Tyr Gly Lys Arg Thr Glu Asn Val Gln Tyr Arg His
            980                 985                 990
```

-continued

Val Glu Leu Ala Arg Val Gly Gln Val Val Glu Val Asp Thr Leu Glu
         995                1000                1005

His Val Gln His Ile Ile Gly Gly Ala Gly Asn Asp Ser Ile Thr
    1010             1015                1020

Gly Asn Ala His Asp Asn Phe Leu Ala Gly Ser Gly Asp Asp
    1025             1030                1035

Arg Leu Asp Gly Gly Ala Gly Asn Asp Thr Leu Val Gly Gly Glu
    1040             1045                1050

Gly Gln Asn Thr Val Ile Gly Gly Ala Gly Asp Asp Val Phe Leu
    1055             1060                1065

Gln Asp Leu Gly Val Trp Ser Asn Gln Leu Asp Gly Gly Ala Gly
    1070             1075                1080

Val Asp Thr Val Lys Tyr Asn Val His Gln Pro Ser Glu Glu Arg
    1085             1090                1095

Leu Glu Arg Met Gly Asp Thr Gly Ile His Ala Asp Leu Gln Lys
    1100             1105                1110

Gly Thr Val Glu Lys Trp Pro Ala Leu Asn Leu Phe Ser Val Asp
    1115             1120                1125

His Val Lys Asn Ile Glu Asn Leu His Gly Ser Arg Leu Asn Asp
    1130             1135                1140

Arg Ile Ala Gly Asp Asp Gln Asp Asn Glu Leu Trp Gly His Asp
    1145             1150                1155

Gly Asn Asp Thr Ile Arg Gly Arg Gly Gly Asp Asp Ile Leu Arg
    1160             1165                1170

Gly Gly Leu Gly Leu Asp Thr Leu Tyr Gly Glu Asp Gly Asn Asp
    1175             1180                1185

Ile Phe Leu Gln Asp Asp Glu Thr Val Ser Asp Asp Ile Asp Gly
    1190             1195                1200

Gly Ala Gly Leu Asp Thr Val Asp Tyr Ser Ala Met Ile His Pro
    1205             1210                1215

Gly Arg Ile Val Ala Pro His Glu Tyr Gly Phe Gly Ile Glu Ala
    1220             1225                1230

Asp Leu Ser Arg Glu Trp Val Arg Lys Ala Ser Ala Leu Gly Val
    1235             1240                1245

Asp Tyr Tyr Asp Asn Val Arg Asn Val Glu Asn Val Ile Gly Thr
    1250             1255                1260

Ser Met Lys Asp Val Leu Ile Gly Asp Ala Gln Ala Asn Thr Leu
    1265             1270                1275

Met Gly Gln Gly Gly Asp Asp Thr Val Arg Gly Gly Asp Gly Asp
    1280             1285                1290

Asp Leu Leu Phe Gly Gly Asp Gly Asn Asp Met Leu Tyr Gly Asp
    1295             1300                1305

Ala Gly Asn Asp Thr Leu Tyr Gly Gly Leu Gly Asp Asp Thr Leu
    1310             1315                1320

Glu Gly Gly Ala Gly Asn Asp Trp Phe Gly Gln Thr Gln Ala Arg
    1325             1330                1335

Glu His Asp Val Leu Arg Gly Gly Asp Gly Val Asp Thr Val Asp
    1340             1345                1350

Tyr Ser Gln Thr Gly Ala His Ala Gly Ile Ala Ala Gly Arg Ile
    1355             1360                1365

Gly Leu Gly Ile Leu Ala Asp Leu Gly Ala Gly Arg Val Asp Lys
    1370             1375                1380

Leu Gly Glu Ala Gly Ser Ser Ala Tyr Asp Thr Val Ser Gly Ile

```
            1385                1390                1395

Glu Asn Val Val Gly Thr Glu Leu Ala Asp Arg Ile Thr Gly Asp
    1400                1405                1410

Ala Gln Ala Asn Val Leu Arg Gly Ala Gly Ala Asp Val Leu
    1415                1420                1425

Ala Gly Gly Glu Gly Asp Val Leu Leu Gly Asp Gly Asp
    1430                1435                1440

Asp Gln Leu Ser Gly Asp Ala Gly Arg Asp Arg Leu Tyr Gly Glu
    1445                1450                1455

Ala Gly Asp Asp Trp Phe Phe Gln Asp Ala Ala Asn Ala Gly Asn
    1460                1465                1470

Leu Leu Asp Gly Gly Asp Gly Arg Asp Thr Val Asp Phe Ser Gly
    1475                1480                1485

Pro Gly Arg Gly Leu Asp Ala Gly Ala Lys Gly Val Phe Leu Ser
    1490                1495                1500

Leu Gly Lys Gly Phe Ala Ser Leu Met Asp Glu Pro Glu Thr Ser
    1505                1510                1515

Asn Val Leu Arg Asn Ile Glu Asn Ala Val Gly Ser Ala Arg Asp
    1520                1525                1530

Asp Val Leu Ile Gly Asp Ala Gly Ala Asn Val Leu Asn Gly Leu
    1535                1540                1545

Ala Gly Asn Asp Val Leu Ser Gly Gly Ala Gly Asp Asp Val Leu
    1550                1555                1560

Leu Gly Asp Glu Gly Ser Asp Leu Leu Ser Gly Asp Ala Gly Asn
    1565                1570                1575

Asp Asp Leu Phe Gly Gly Gln Gly Asp Asp Thr Tyr Leu Phe Gly
    1580                1585                1590

Val Gly Tyr Gly His Asp Thr Ile Tyr Glu Ser Gly Gly Gly His
    1595                1600                1605

Asp Thr Ile Arg Ile Asn Ala Gly Ala Asp Gln Leu Trp Phe Ala
    1610                1615                1620

Arg Gln Gly Asn Asp Leu Glu Ile Arg Ile Leu Gly Thr Asp Asp
    1625                1630                1635

Ala Leu Thr Val His Asp Trp Tyr Arg Asp Ala Asp His Arg Val
    1640                1645                1650

Glu Ile Ile His Ala Ala Asn Gln Ala Val Asp Gln Ala Gly Ile
    1655                1660                1665

Glu Lys Leu Val Glu Ala Met Ala Gln Tyr Pro Asp Pro Gly Ala
    1670                1675                1680

Ala Ala Ala Ala Pro Pro Ala Ala Arg Val Pro Asp Thr Leu Met
    1685                1690                1695

Gln Ser Leu Ala Val Asn Trp Arg
    1700                1705

<210> SEQ ID NO 2
<211> LENGTH: 1706
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
```

```
                  20                  25                  30
Glu Lys Asn Ala Thr Leu Met Phe Arg Leu Val Asn Pro His Ser Thr
             35                  40                  45
Ser Leu Ile Ala Glu Gly Val Ala Thr Lys Gly Leu Gly Val His Ala
 50                  55                  60
Lys Ser Ser Asp Trp Gly Leu Gln Ala Gly Tyr Ile Pro Val Asn Pro
 65                  70                  75                  80
Asn Leu Ser Lys Leu Phe Gly Arg Ala Pro Glu Val Ile Ala Arg Ala
                 85                  90                  95
Asp Asn Asp Val Asn Ser Ser Leu Ala His Gly His Thr Ala Val Asp
            100                 105                 110
Leu Thr Leu Ser Lys Glu Arg Leu Asp Tyr Leu Arg Gln Ala Gly Leu
            115                 120                 125
Val Thr Gly Met Ala Asp Gly Val Val Ala Ser Asn His Ala Gly Tyr
            130                 135                 140
Glu Gln Phe Glu Phe Arg Val Lys Glu Thr Ser Asp Gly Arg Tyr Ala
145                 150                 155                 160
Val Gln Tyr Arg Arg Lys Gly Asp Asp Phe Glu Ala Val Lys Val
            165                 170                 175
Ile Gly Asn Ala Ala Gly Ile Pro Leu Thr Ala Asp Ile Asp Met Phe
            180                 185                 190
Ala Ile Met Pro His Leu Ser Asn Phe Arg Asp Ser Ala Arg Ser Ser
            195                 200                 205
Val Thr Ser Gly Asp Ser Val Thr Asp Tyr Leu Ala Arg Thr Arg Arg
            210                 215                 220
Ala Ala Ser Glu Ala Thr Gly Gly Leu Asp Arg Glu Arg Ile Asp Leu
225                 230                 235                 240
Leu Trp Lys Ile Ala Arg Ala Gly Ala Arg Ser Ala Val Gly Thr Glu
            245                 250                 255
Ala Arg Arg Gln Phe Arg Tyr Asp Gly Asp Met Asn Ile Gly Val Ile
            260                 265                 270
Thr Asp Phe Glu Leu Glu Val Arg Asn Ala Leu Asn Arg Arg Ala His
            275                 280                 285
Ala Val Gly Ala Gln Asp Val Val Gln His Gly Thr Glu Gln Asn Asn
            290                 295                 300
Pro Phe Pro Glu Ala Asp Glu Lys Ile Phe Val Ser Ala Thr Gly
305                 310                 315                 320
Glu Ser Gln Met Leu Thr Arg Gly Gln Leu Lys Glu Tyr Ile Gly Gln
            325                 330                 335
Gln Arg Gly Glu Gly Tyr Val Phe Tyr Glu Asn Arg Ala Tyr Gly Val
            340                 345                 350
Ala Gly Lys Ser Leu Phe Asp Asp Gly Leu Gly Ala Ala Pro Gly Val
            355                 360                 365
Pro Ser Gly Arg Ser Lys Phe Ser Pro Asp Val Leu Glu Thr Val Pro
            370                 375                 380
Ala Ser Pro Gly Leu Arg Arg Pro Ser Leu Gly Ala Val Glu Arg Gln
385                 390                 395                 400
Asp Ser Gly Tyr Asp Ser Leu Asp Gly Val Gly Ser Arg Ser Phe Ser
            405                 410                 415
Leu Gly Glu Val Ser Asp Met Ala Ala Val Glu Ala Ala Glu Leu Glu
            420                 425                 430
Met Thr Arg Gln Val Leu His Ala Gly Ala Arg Gln Asp Asp Ala Glu
            435                 440                 445
```

-continued

```
Pro Gly Val Ser Gly Ala Ser Ala His Trp Gly Gln Arg Ala Leu Gln
    450                 455                 460
Gly Ala Gln Ala Val Ala Ala Gln Arg Leu Val His Ala Ile Ala
465                 470                 475                 480
Leu Met Thr Gln Phe Gly Arg Ala Gly Ser Thr Asn Thr Pro Gln Glu
                    485                 490                 495
Ala Ala Ser Leu Ser Ala Ala Val Phe Gly Leu Gly Glu Ala Ser Ser
                500                 505                 510
Ala Val Ala Glu Thr Val Ser Gly Phe Phe Arg Gly Ser Ser Arg Trp
            515                 520                 525
Ala Gly Gly Phe Gly Val Ala Gly Ala Met Ala Leu Gly Gly Gly
    530                 535                 540
Ile Ala Ala Ala Val Gly Ala Gly Met Ser Leu Thr Asp Asp Ala Pro
545                 550                 555                 560
Ala Gly Gln Lys Ala Ala Gly Ala Gln Ile Ala Leu Gln Leu Thr
                565                 570                 575
Gly Gly Thr Val Glu Leu Ala Ser Ser Ile Ala Leu Ala Leu Ala Ala
                580                 585                 590
Ala Arg Gly Val Thr Ser Gly Leu Gln Val Ala Gly Ala Ser Ala Gly
        595                 600                 605
Ala Ala Ala Gly Ala Leu Ala Ala Ala Leu Ser Pro Met Glu Ile Tyr
    610                 615                 620
Gly Leu Val Gln Gln Ser His Tyr Ala Asp Gln Leu Asp Lys Leu Ala
625                 630                 635                 640
Gln Glu Ser Ser Ala Tyr Gly Tyr Glu Gly Asp Ala Leu Leu Ala Gln
                645                 650                 655
Leu Tyr Arg Asp Lys Thr Ala Ala Glu Gly Ala Val Ala Gly Val Ser
            660                 665                 670
Ala Val Leu Ser Thr Val Gly Ala Ala Val Ser Ile Ala Ala Ala Ala
        675                 680                 685
Ser Val Val Gly Ala Pro Val Ala Val Thr Ser Leu Leu Thr Gly
    690                 695                 700
Ala Leu Asn Gly Ile Leu Arg Gly Val Gln Gln Pro Ile Ile Glu Lys
705                 710                 715                 720
Leu Ala Asn Asp Tyr Ala Arg Lys Ile Asp Glu Leu Gly Gly Pro Gln
                725                 730                 735
Ala Tyr Phe Glu Lys Asn Leu Gln Ala Arg His Glu Gln Leu Ala Asn
            740                 745                 750
Ser Asp Gly Leu Arg Lys Met Leu Ala Asp Leu Gln Ala Gly Trp Asn
        755                 760                 765
Ala Ser Ser Val Ile Gly Val Gln Thr Thr Glu Ile Ser Lys Ser Ala
    770                 775                 780
Leu Glu Leu Ala Ala Ile Thr Gly Asn Ala Asp Asn Leu Lys Ser Val
785                 790                 795                 800
Asp Val Phe Val Asp Arg Phe Val Gln Gly Glu Arg Val Ala Gly Gln
                805                 810                 815
Pro Val Val Leu Asp Val Ala Ala Gly Ile Asp Ile Ala Ser Arg
            820                 825                 830
Lys Gly Glu Arg Pro Ala Leu Thr Phe Ile Thr Pro Leu Ala Ala Pro
        835                 840                 845
Gly Glu Glu Gln Arg Arg Thr Lys Thr Gly Arg Ser Glu Phe Thr
    850                 855                 860
Thr Phe Val Glu Ile Val Gly Lys Gln Asp Arg Trp Arg Ile Arg Asp
865                 870                 875                 880
```

Gly Ala Ala Asp Thr Thr Ile Asp Leu Ala Lys Val Val Ser Gln Leu
                885                 890                 895

Val Asp Ala Asn Gly Val Leu Lys His Ser Ile Lys Leu Asp Val Ile
                900                 905                 910

Gly Gly Asp Gly Asp Val Leu Ala Asn Ala Ser Arg Ile His
                915                 920                 925

Tyr Asp Gly Gly Ala Gly Thr Asn Thr Val Ser Tyr Ala Ala Leu Gly
        930                 935                 940

Arg Gln Asp Ser Ile Thr Val Ser Ala Asp Gly Glu Arg Phe Asn Val
945                 950                 955                 960

Arg Lys Gln Leu Asn Asn Ala Asn Val Tyr Arg Glu Gly Val Ala Thr
                965                 970                 975

Gln Thr Thr Ala Tyr Gly Lys Arg Thr Glu Asn Val Gln Tyr Arg His
                980                 985                 990

Val Glu Leu Ala Arg Val Gly Gln Val Val Glu Val Asp Thr Leu Glu
                995                 1000                1005

His Val Gln His Ile Ile Gly Gly Ala Gly Asn Asp Ser Ile Thr
            1010                1015                1020

Gly Asn Ala His Asp Asn Phe Leu Ala Gly Gly Ser Gly Asp Asp
            1025                1030                1035

Arg Leu Asp Gly Gly Ala Gly Asn Asp Thr Leu Val Gly Gly Glu
            1040                1045                1050

Gly Gln Asn Thr Val Ile Gly Gly Ala Gly Asp Asp Val Phe Leu
            1055                1060                1065

Gln Asp Leu Gly Val Trp Ser Asn Gln Leu Asp Gly Gly Ala Gly
            1070                1075                1080

Val Asp Thr Val Lys Tyr Asn Val His Gln Pro Ser Glu Glu Arg
            1085                1090                1095

Leu Glu Arg Met Gly Asp Thr Gly Ile His Ala Asp Leu Gln Lys
            1100                1105                1110

Gly Thr Val Glu Lys Trp Pro Ala Leu Asn Leu Phe Ser Val Asp
            1115                1120                1125

His Val Lys Asn Ile Glu Asn Leu His Gly Ser Arg Leu Asn Asp
            1130                1135                1140

Arg Ile Ala Gly Asp Asp Gln Asp Asn Glu Leu Trp Gly His Asp
            1145                1150                1155

Gly Asn Asp Thr Ile Arg Gly Arg Gly Gly Asp Ile Leu Arg
            1160                1165                1170

Gly Gly Leu Gly Leu Asp Thr Leu Tyr Gly Glu Asp Gly Asn Asp
            1175                1180                1185

Ile Phe Leu Gln Asp Asp Glu Thr Val Ser Asp Asp Ile Asp Gly
            1190                1195                1200

Gly Ala Gly Leu Asp Thr Val Asp Tyr Ser Ala Met Ile His Pro
            1205                1210                1215

Gly Arg Ile Val Ala Pro His Glu Tyr Gly Phe Gly Ile Glu Ala
            1220                1225                1230

Asp Leu Ser Arg Glu Trp Val Arg Lys Ala Ser Ala Leu Gly Val
            1235                1240                1245

Asp Tyr Tyr Asp Asn Val Arg Asn Val Glu Asn Val Ile Gly Thr
            1250                1255                1260

Ser Met Lys Asp Val Leu Ile Gly Asp Ala Gln Ala Asn Thr Leu
            1265                1270                1275

Met Gly Gln Gly Gly Asp Asp Thr Val Arg Gly Gly Asp Gly Asp

```
                1280                1285                1290

Asp Leu Leu Phe Gly Gly Asp Gly Asn Asp Met Leu Tyr Gly Asp
    1295                1300                1305

Ala Gly Asn Asp Thr Leu Tyr Gly Gly Leu Gly Asp Asp Thr Leu
    1310                1315                1320

Glu Gly Gly Ala Gly Asn Asp Trp Phe Gly Gln Thr Gln Ala Arg
    1325                1330                1335

Glu His Asp Val Leu Arg Gly Gly Asp Gly Val Asp Thr Val Asp
    1340                1345                1350

Tyr Ser Gln Thr Gly Ala His Ala Gly Ile Ala Ala Gly Arg Ile
    1355                1360                1365

Gly Leu Gly Ile Leu Ala Asp Leu Gly Ala Gly Arg Val Asp Lys
    1370                1375                1380

Leu Gly Glu Ala Gly Ser Ser Ala Tyr Asp Thr Val Ser Gly Ile
    1385                1390                1395

Glu Asn Val Val Gly Thr Glu Leu Ala Asp Arg Ile Thr Gly Asp
    1400                1405                1410

Ala Gln Ala Asn Val Leu Arg Gly Ala Gly Gly Ala Asp Val Leu
    1415                1420                1425

Ala Gly Gly Glu Gly Asp Asp Val Leu Leu Gly Gly Asp Gly Asp
    1430                1435                1440

Asp Gln Leu Ser Gly Asp Ala Gly Arg Asp Arg Leu Tyr Gly Glu
    1445                1450                1455

Ala Gly Asp Asp Trp Phe Phe Gln Asp Ala Ala Asn Ala Gly Asn
    1460                1465                1470

Leu Leu Asp Gly Gly Asp Gly Arg Asp Thr Val Asp Phe Ser Gly
    1475                1480                1485

Pro Gly Arg Gly Leu Asp Ala Gly Ala Lys Gly Val Phe Leu Ser
    1490                1495                1500

Leu Gly Lys Gly Phe Ala Ser Leu Met Asp Glu Pro Glu Thr Ser
    1505                1510                1515

Asn Val Leu Arg Asn Ile Glu Asn Ala Val Gly Ser Ala Arg Asp
    1520                1525                1530

Asp Val Leu Ile Gly Asp Ala Gly Ala Asn Val Leu Asn Gly Leu
    1535                1540                1545

Ala Gly Asn Asp Val Leu Ser Gly Gly Ala Gly Asp Asp Val Leu
    1550                1555                1560

Leu Gly Asp Glu Gly Ser Asp Leu Leu Ser Gly Asp Ala Gly Asn
    1565                1570                1575

Asp Asp Leu Phe Gly Gly Gln Gly Asp Asp Thr Tyr Leu Phe Gly
    1580                1585                1590

Val Gly Tyr Gly His Asp Thr Ile Tyr Glu Ser Gly Gly Gly His
    1595                1600                1605

Asp Thr Ile Arg Ile Asn Ala Gly Ala Asp Gln Leu Trp Phe Ala
    1610                1615                1620

Arg Gln Gly Asn Asp Leu Glu Ile Arg Ile Leu Gly Thr Asp Asp
    1625                1630                1635

Ala Leu Thr Val His Asp Trp Tyr Arg Asp Ala Asp His Arg Val
    1640                1645                1650

Glu Ile Ile His Ala Ala Asn Gln Ala Val Asp Gln Ala Gly Ile
    1655                1660                1665

Glu Lys Leu Val Glu Ala Met Ala Gln Tyr Pro Asp Pro Gly Ala
    1670                1675                1680
```

-continued

```
Ala Ala Ala Ala Pro Pro Ala Ala Arg Val Pro Asp Thr Leu Met
    1685            1690            1695

Gln Ser Leu Ala Val Asn Trp Arg
    1700            1705

<210> SEQ ID NO 3
<211> LENGTH: 1708
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65              70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145             150                 155                 160

Val Gln Tyr Arg Arg Lys Gly Gly Asp Phe Glu Ala Val Lys Val
                165                 170                 175

Ile Gly Asn Ala Ala Gly Ile Pro Leu Thr Ala Asp Gly Ser Ile Asp
            180                 185                 190

Met Phe Ala Ile Met Pro His Leu Ser Asn Phe Arg Asp Ser Ala Arg
        195                 200                 205

Ser Ser Val Thr Ser Gly Asp Ser Val Thr Asp Tyr Leu Ala Arg Thr
    210                 215                 220

Arg Arg Ala Ala Ser Glu Ala Thr Gly Gly Leu Asp Arg Glu Arg Ile
225             230                 235                 240

Asp Leu Leu Trp Lys Ile Ala Arg Ala Gly Ala Arg Ser Ala Val Gly
                245                 250                 255

Thr Glu Ala Arg Arg Gln Phe Arg Tyr Asp Gly Asp Met Asn Ile Gly
            260                 265                 270

Val Ile Thr Asp Phe Glu Leu Glu Val Arg Asn Ala Leu Asn Arg Arg
        275                 280                 285

Ala His Ala Val Gly Ala Gln Asp Val Val Gln His Gly Thr Glu Gln
    290                 295                 300

Asn Asn Pro Phe Pro Glu Ala Asp Glu Lys Ile Phe Val Val Ser Ala
305             310                 315                 320

Thr Gly Glu Ser Gln Met Leu Thr Arg Gly Gln Leu Lys Glu Tyr Ile
                325                 330                 335
```

Gly Gln Gln Arg Gly Glu Gly Tyr Val Phe Tyr Glu Asn Arg Ala Tyr
            340                 345                 350

Gly Val Ala Gly Lys Ser Leu Phe Asp Asp Gly Leu Gly Ala Ala Pro
            355                 360                 365

Gly Val Pro Ser Gly Arg Ser Lys Phe Ser Pro Asp Val Leu Glu Thr
            370                 375                 380

Val Pro Ala Ser Pro Gly Leu Arg Arg Pro Ser Leu Gly Ala Val Glu
385                 390                 395                 400

Arg Gln Asp Ser Gly Tyr Asp Ser Leu Asp Gly Val Gly Ser Arg Ser
                405                 410                 415

Phe Ser Leu Gly Glu Val Ser Asp Met Ala Ala Val Glu Ala Ala Glu
            420                 425                 430

Leu Glu Met Thr Arg Gln Val Leu His Ala Gly Ala Arg Gln Asp Asp
            435                 440                 445

Ala Glu Pro Gly Val Ser Gly Ala Ser Ala His Trp Gly Gln Arg Ala
            450                 455                 460

Leu Gln Gly Ala Gln Ala Val Ala Ala Ala Gln Arg Leu Val His Ala
465                 470                 475                 480

Ile Ala Leu Met Thr Gln Phe Gly Arg Ala Gly Ser Thr Asn Thr Pro
                485                 490                 495

Gln Glu Ala Ala Ser Leu Ser Ala Ala Val Phe Gly Leu Gly Glu Ala
            500                 505                 510

Ser Ser Ala Val Ala Glu Thr Val Ser Gly Phe Phe Arg Gly Ser Ser
            515                 520                 525

Arg Trp Ala Gly Gly Phe Gly Val Ala Gly Gly Ala Met Ala Leu Gly
            530                 535                 540

Gly Gly Ile Ala Ala Val Gly Ala Gly Met Ser Leu Thr Asp Asp
545                 550                 555                 560

Ala Pro Ala Gly Gln Lys Ala Ala Gly Ala Gln Ile Ala Leu Gln
                565                 570                 575

Leu Thr Gly Gly Thr Val Glu Leu Ala Ser Ser Ile Ala Leu Ala Leu
            580                 585                 590

Ala Ala Ala Arg Gly Val Thr Ser Gly Leu Gln Val Ala Gly Ala Ser
            595                 600                 605

Ala Gly Ala Ala Gly Ala Leu Ala Ala Leu Ser Pro Met Glu
            610                 615                 620

Ile Tyr Gly Leu Val Gln Gln Ser His Tyr Ala Asp Gln Leu Asp Lys
625                 630                 635                 640

Leu Ala Gln Glu Ser Ser Ala Tyr Gly Tyr Glu Gly Asp Ala Leu Leu
                645                 650                 655

Ala Gln Leu Tyr Arg Asp Lys Thr Ala Ala Glu Gly Ala Val Ala Gly
                660                 665                 670

Val Ser Ala Val Leu Ser Thr Val Gly Ala Ala Val Ser Ile Ala Ala
            675                 680                 685

Ala Ala Ser Val Val Gly Ala Pro Val Ala Val Thr Ser Leu Leu
            690                 695                 700

Thr Gly Ala Leu Asn Gly Ile Leu Arg Gly Val Gln Gln Pro Ile Ile
705                 710                 715                 720

Glu Lys Leu Ala Asn Asp Tyr Ala Arg Lys Ile Asp Glu Leu Gly Gly
                725                 730                 735

Pro Gln Ala Tyr Phe Glu Lys Asn Leu Gln Ala Arg His Glu Gln Leu
                740                 745                 750

Ala Asn Ser Asp Gly Leu Arg Lys Met Leu Ala Asp Leu Gln Ala Gly
            755                 760                 765

```
Trp Asn Ala Ser Ser Val Ile Gly Val Gln Thr Thr Glu Ile Ser Lys
    770                 775                 780

Ser Ala Leu Glu Leu Ala Ala Ile Thr Gly Asn Ala Asp Asn Leu Lys
785                 790                 795                 800

Ser Val Asp Val Phe Val Asp Arg Phe Val Gln Gly Glu Arg Val Ala
                805                 810                 815

Gly Gln Pro Val Val Leu Asp Val Ala Ala Gly Gly Ile Asp Ile Ala
            820                 825                 830

Ser Arg Lys Gly Glu Arg Pro Ala Leu Thr Phe Ile Thr Pro Leu Ala
            835                 840                 845

Ala Pro Gly Glu Glu Gln Arg Arg Thr Lys Thr Gly Arg Ser Glu
    850                 855                 860

Phe Thr Thr Phe Val Glu Ile Val Gly Lys Gln Asp Arg Trp Arg Ile
865                 870                 875                 880

Arg Asp Gly Ala Ala Asp Thr Thr Ile Asp Leu Ala Lys Val Val Ser
                885                 890                 895

Gln Leu Val Asp Ala Asn Gly Val Leu Lys His Ser Ile Lys Leu Asp
            900                 905                 910

Val Ile Gly Gly Asp Gly Asp Val Val Leu Ala Asn Ala Ser Arg
    915                 920                 925

Ile His Tyr Asp Gly Gly Ala Gly Thr Asn Thr Val Ser Tyr Ala Ala
    930                 935                 940

Leu Gly Arg Gln Asp Ser Ile Thr Val Ser Ala Asp Gly Glu Arg Phe
945                 950                 955                 960

Asn Val Arg Lys Gln Leu Asn Asn Ala Asn Val Tyr Arg Glu Gly Val
                965                 970                 975

Ala Thr Gln Thr Thr Ala Tyr Gly Lys Arg Thr Glu Asn Val Gln Tyr
            980                 985                 990

Arg His Val Glu Leu Ala Arg Val Gly Gln Val Val Glu Val Asp Thr
    995                 1000                1005

Leu Glu His Val Gln His Ile Ile Gly Gly Ala Gly Asn Asp Ser
    1010                1015                1020

Ile Thr Gly Asn Ala His Asp Asn Phe Leu Ala Gly Gly Ser Gly
    1025                1030                1035

Asp Asp Arg Leu Asp Gly Gly Ala Gly Asn Asp Thr Leu Val Gly
    1040                1045                1050

Gly Glu Gly Gln Asn Thr Val Ile Gly Gly Ala Gly Asp Asp Val
    1055                1060                1065

Phe Leu Gln Asp Leu Gly Val Trp Ser Asn Gln Leu Asp Gly Gly
    1070                1075                1080

Ala Gly Val Asp Thr Val Lys Tyr Asn Val His Gln Pro Ser Glu
    1085                1090                1095

Glu Arg Leu Glu Arg Met Gly Asp Thr Gly Ile His Ala Asp Leu
    1100                1105                1110

Gln Lys Gly Thr Val Glu Lys Trp Pro Ala Leu Asn Leu Phe Ser
    1115                1120                1125

Val Asp His Val Lys Asn Ile Glu Asn Leu His Gly Ser Arg Leu
    1130                1135                1140

Asn Asp Arg Ile Ala Gly Asp Asp Gln Asp Asn Glu Leu Trp Gly
    1145                1150                1155

His Asp Gly Asn Asp Thr Ile Arg Gly Arg Gly Gly Asp Asp Ile
    1160                1165                1170

Leu Arg Gly Gly Leu Gly Leu Asp Thr Leu Tyr Gly Glu Asp Gly
```

```
                1175                1180                1185

Asn Asp Ile Phe Leu Gln Asp Asp Glu Thr Val Ser Asp Asp Ile
    1190                1195                1200

Asp Gly Gly Ala Gly Leu Asp Thr Val Asp Tyr Ser Ala Met Ile
    1205                1210                1215

His Pro Gly Arg Ile Val Ala Pro His Glu Tyr Gly Phe Gly Ile
    1220                1225                1230

Glu Ala Asp Leu Ser Arg Glu Trp Val Arg Lys Ala Ser Ala Leu
    1235                1240                1245

Gly Val Asp Tyr Tyr Asp Asn Val Arg Asn Val Glu Asn Val Ile
    1250                1255                1260

Gly Thr Ser Met Lys Asp Val Leu Ile Gly Asp Ala Gln Ala Asn
    1265                1270                1275

Thr Leu Met Gly Gln Gly Gly Asp Asp Thr Val Arg Gly Gly Asp
    1280                1285                1290

Gly Asp Asp Leu Leu Phe Gly Gly Asp Gly Asn Asp Met Leu Tyr
    1295                1300                1305

Gly Asp Ala Gly Asn Asp Thr Leu Tyr Gly Gly Leu Gly Asp Asp
    1310                1315                1320

Thr Leu Glu Gly Gly Ala Gly Asn Asp Trp Phe Gly Gln Thr Gln
    1325                1330                1335

Ala Arg Glu His Asp Val Leu Arg Gly Gly Asp Gly Val Asp Thr
    1340                1345                1350

Val Asp Tyr Ser Gln Thr Gly Ala His Ala Gly Ile Ala Ala Gly
    1355                1360                1365

Arg Ile Gly Leu Gly Ile Leu Ala Asp Leu Gly Ala Gly Arg Val
    1370                1375                1380

Asp Lys Leu Gly Glu Ala Gly Ser Ser Ala Tyr Asp Thr Val Ser
    1385                1390                1395

Gly Ile Glu Asn Val Val Gly Thr Glu Leu Ala Asp Arg Ile Thr
    1400                1405                1410

Gly Asp Ala Gln Ala Asn Val Leu Arg Gly Ala Gly Gly Ala Asp
    1415                1420                1425

Val Leu Ala Gly Gly Glu Gly Asp Asp Val Leu Leu Gly Gly Asp
    1430                1435                1440

Gly Asp Asp Gln Leu Ser Gly Asp Ala Gly Arg Asp Arg Leu Tyr
    1445                1450                1455

Gly Glu Ala Gly Asp Asp Trp Phe Phe Gln Asp Ala Ala Asn Ala
    1460                1465                1470

Gly Asn Leu Leu Asp Gly Gly Asp Gly Arg Asp Thr Val Asp Phe
    1475                1480                1485

Ser Gly Pro Gly Arg Gly Leu Asp Ala Gly Ala Lys Gly Val Phe
    1490                1495                1500

Leu Ser Leu Gly Lys Gly Phe Ala Ser Leu Met Asp Glu Pro Glu
    1505                1510                1515

Thr Ser Asn Val Leu Arg Asn Ile Glu Asn Ala Val Gly Ser Ala
    1520                1525                1530

Arg Asp Asp Val Leu Ile Gly Asp Ala Gly Ala Asn Val Leu Asn
    1535                1540                1545

Gly Leu Ala Gly Asn Asp Val Leu Ser Gly Gly Ala Gly Asp Asp
    1550                1555                1560

Val Leu Leu Gly Asp Glu Gly Ser Asp Leu Leu Ser Gly Asp Ala
    1565                1570                1575
```

```
Gly Asn Asp Asp Leu Phe Gly Gln Gly Asp Thr Tyr Leu
    1580                1585            1590

Phe Gly Val Gly Tyr Gly His Asp Thr Ile Tyr Glu Ser Gly Gly
    1595                1600            1605

Gly His Asp Thr Ile Arg Ile Asn Ala Gly Ala Asp Gln Leu Trp
    1610                1615            1620

Phe Ala Arg Gln Gly Asn Asp Leu Glu Ile Arg Ile Leu Gly Thr
    1625                1630            1635

Asp Asp Ala Leu Thr Val His Asp Trp Tyr Arg Asp Ala Asp His
    1640                1645            1650

Arg Val Glu Ile Ile His Ala Ala Asn Gln Ala Val Asp Gln Ala
    1655                1660            1665

Gly Ile Glu Lys Leu Val Glu Ala Met Ala Gln Tyr Pro Asp Pro
    1670                1675            1680

Gly Ala Ala Ala Ala Ala Pro Pro Ala Ala Arg Val Pro Asp Thr
    1685                1690            1695

Leu Met Gln Ser Leu Ala Val Asn Trp Arg
    1700                1705
```

```
<210> SEQ ID NO 4
<211> LENGTH: 1720
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Phe Glu Ala Val Lys Val
                165                 170                 175

Ile Gly Asn Ala Ala Gly Ile Pro Leu Thr Ala Asp Gly Ser Ile Asp
            180                 185                 190

Met Phe Ala Ile Met Pro His Leu Ser Asn Phe Arg Asp Ser Ala Arg
        195                 200                 205

Ser Ser Val Thr Ser Gly Asp Ser Val Thr Asp Tyr Leu Ala Arg Thr
    210                 215                 220
```

```
Arg Arg Ala Ala Ser Glu Ala Thr Gly Gly Val Leu Ser Ile Ile Asn
225                 230                 235                 240

Phe Glu Lys Leu Val His Leu Asp Arg Glu Arg Ile Asp Leu Leu Trp
            245                 250                 255

Lys Ile Ala Arg Ala Gly Ala Arg Ser Ala Val Gly Thr Glu Ala Arg
        260                 265                 270

Arg Gln Phe Arg Tyr Asp Gly Asp Met Asn Ile Gly Val Ile Thr Asp
    275                 280                 285

Phe Glu Leu Glu Val Arg Asn Ala Leu Asn Arg Arg Ala His Ala Val
290                 295                 300

Gly Ala Gln Asp Val Val Gln His Gly Thr Glu Gln Asn Asn Pro Phe
305                 310                 315                 320

Pro Glu Ala Asp Glu Lys Ile Phe Val Val Ser Ala Thr Gly Glu Ser
            325                 330                 335

Gln Met Leu Thr Arg Gly Gln Leu Lys Glu Tyr Ile Gly Gln Gln Arg
        340                 345                 350

Gly Glu Gly Tyr Val Phe Tyr Glu Asn Arg Ala Tyr Gly Val Ala Gly
    355                 360                 365

Lys Ser Leu Phe Asp Asp Gly Leu Gly Ala Ala Pro Gly Val Pro Ser
370                 375                 380

Gly Arg Ser Lys Phe Ser Pro Asp Val Leu Glu Thr Val Pro Ala Ser
385                 390                 395                 400

Pro Gly Leu Arg Arg Pro Ser Leu Gly Ala Val Glu Arg Gln Asp Ser
            405                 410                 415

Gly Tyr Asp Ser Leu Asp Gly Val Gly Ser Arg Ser Phe Ser Leu Gly
        420                 425                 430

Glu Val Ser Asp Met Ala Ala Val Glu Ala Ala Glu Leu Glu Met Thr
    435                 440                 445

Arg Gln Val Leu His Ala Gly Arg Gln Asp Asp Ala Glu Pro Gly
450                 455                 460

Val Ser Gly Ala Ser Ala His Trp Gly Gln Arg Ala Leu Gln Gly Ala
465                 470                 475                 480

Gln Ala Val Ala Ala Ala Gln Arg Leu Val His Ala Ile Ala Leu Met
            485                 490                 495

Thr Gln Phe Gly Arg Ala Gly Ser Thr Asn Thr Pro Gln Glu Ala Ala
        500                 505                 510

Ser Leu Ser Ala Ala Val Phe Gly Leu Gly Glu Ala Ser Ser Ala Val
    515                 520                 525

Ala Glu Thr Val Ser Gly Phe Phe Arg Gly Ser Ser Arg Trp Ala Gly
530                 535                 540

Gly Phe Gly Val Ala Gly Gly Ala Met Ala Leu Gly Gly Gly Ile Ala
545                 550                 555                 560

Ala Ala Val Gly Ala Gly Met Ser Leu Thr Asp Asp Ala Pro Ala Gly
            565                 570                 575

Gln Lys Ala Ala Ala Gly Ala Gln Ile Ala Leu Gln Leu Thr Gly Gly
        580                 585                 590

Thr Val Glu Leu Ala Ser Ser Ile Ala Leu Ala Leu Ala Ala Ala Arg
    595                 600                 605

Gly Val Thr Ser Gly Leu Gln Val Ala Gly Ala Ser Ala Gly Ala Ala
610                 615                 620

Ala Gly Ala Leu Ala Ala Ala Leu Ser Pro Met Glu Ile Tyr Gly Leu
625                 630                 635                 640

Val Gln Gln Ser His Tyr Ala Asp Gln Leu Asp Lys Leu Ala Gln Glu
            645                 650                 655
```

```
Ser Ser Ala Tyr Gly Tyr Glu Gly Asp Ala Leu Leu Ala Gln Leu Tyr
            660                 665                 670

Arg Asp Lys Thr Ala Ala Glu Gly Ala Val Ala Gly Val Ser Ala Val
            675                 680                 685

Leu Ser Thr Val Gly Ala Ala Val Ser Ile Ala Ala Ala Ala Ser Val
            690                 695                 700

Val Gly Ala Pro Val Ala Val Val Thr Ser Leu Leu Thr Gly Ala Leu
705                 710                 715                 720

Asn Gly Ile Leu Arg Gly Val Gln Gln Pro Ile Ile Glu Lys Leu Ala
                725                 730                 735

Asn Asp Tyr Ala Arg Lys Ile Asp Glu Leu Gly Gly Pro Gln Ala Tyr
                740                 745                 750

Phe Glu Lys Asn Leu Gln Ala Arg His Glu Gln Leu Ala Asn Ser Asp
            755                 760                 765

Gly Leu Arg Lys Met Leu Ala Asp Leu Gln Ala Gly Trp Asn Ala Ser
770                 775                 780

Ser Val Ile Gly Val Gln Thr Thr Glu Ile Ser Lys Ser Ala Leu Glu
785                 790                 795                 800

Leu Ala Ala Ile Thr Gly Asn Ala Asp Asn Leu Lys Ser Val Asp Val
                805                 810                 815

Phe Val Asp Arg Phe Val Gln Gly Glu Arg Val Ala Gly Gln Pro Val
            820                 825                 830

Val Leu Asp Val Ala Ala Gly Gly Ile Asp Ile Ala Ser Arg Lys Gly
835                 840                 845

Glu Arg Pro Ala Leu Thr Phe Ile Thr Pro Leu Ala Ala Pro Gly Glu
850                 855                 860

Glu Gln Arg Arg Arg Thr Lys Thr Gly Arg Ser Glu Phe Thr Thr Phe
865                 870                 875                 880

Val Glu Ile Val Gly Lys Gln Asp Arg Trp Arg Ile Arg Asp Gly Ala
            885                 890                 895

Ala Asp Thr Thr Ile Asp Leu Ala Lys Val Val Ser Gln Leu Val Asp
            900                 905                 910

Ala Asn Gly Val Leu Lys His Ser Ile Lys Leu Asp Val Ile Gly Gly
            915                 920                 925

Asp Gly Asp Asp Val Val Leu Ala Asn Ala Ser Arg Ile His Tyr Asp
930                 935                 940

Gly Gly Ala Gly Thr Asn Thr Val Ser Tyr Ala Ala Leu Gly Arg Gln
945                 950                 955                 960

Asp Ser Ile Thr Val Ser Ala Asp Gly Glu Arg Phe Asn Val Arg Lys
            965                 970                 975

Gln Leu Asn Asn Ala Asn Val Tyr Arg Glu Gly Val Ala Thr Gln Thr
            980                 985                 990

Thr Ala Tyr Gly Lys Arg Thr Glu  Asn Val Gln Tyr Arg  His Val Glu
            995                 1000                 1005

Leu Ala  Arg Val Gly Gln Val  Val Glu Val Asp Thr  Leu Glu His
            1010                 1015                 1020

Val Gln  His Ile Ile Gly Gly  Ala Gly Asn Asp Ser  Ile Thr Gly
            1025                 1030                 1035

Asn Ala  His Asp Asn Phe Leu  Ala Gly Gly Ser Gly  Asp Asp Arg
            1040                 1045                 1050

Leu Asp  Gly Gly Ala Gly Asn  Asp Thr Leu Val Gly  Gly Glu Gly
            1055                 1060                 1065

Gln Asn  Thr Val Ile Gly Gly  Ala Gly Asp Asp Val  Phe Leu Gln
```

```
                1070                1075                1080
Asp Leu Gly Val Trp Ser Asn Gln Leu Asp Gly Gly Ala Gly Val
    1085                1090                1095

Asp Thr Val Lys Tyr Asn Val His Gln Pro Ser Glu Glu Arg Leu
    1100                1105                1110

Glu Arg Met Gly Asp Thr Gly Ile His Ala Asp Leu Gln Lys Gly
    1115                1120                1125

Thr Val Glu Lys Trp Pro Ala Leu Asn Leu Phe Ser Val Asp His
    1130                1135                1140

Val Lys Asn Ile Glu Asn Leu His Gly Ser Arg Leu Asn Asp Arg
    1145                1150                1155

Ile Ala Gly Asp Asp Gln Asp Asn Glu Leu Trp Gly His Asp Gly
    1160                1165                1170

Asn Asp Thr Ile Arg Gly Arg Gly Gly Asp Ile Leu Arg Gly
    1175                1180                1185

Gly Leu Gly Leu Asp Thr Leu Tyr Gly Glu Asp Gly Asn Asp Ile
    1190                1195                1200

Phe Leu Gln Asp Asp Glu Thr Val Ser Asp Ile Asp Gly Gly
    1205                1210                1215

Ala Gly Leu Asp Thr Val Asp Tyr Ser Ala Met Ile His Pro Gly
    1220                1225                1230

Arg Ile Val Ala Pro His Glu Tyr Gly Phe Gly Ile Glu Ala Asp
    1235                1240                1245

Leu Ser Arg Glu Trp Val Arg Lys Ala Ser Ala Leu Gly Val Asp
    1250                1255                1260

Tyr Tyr Asp Asn Val Arg Asn Val Glu Asn Val Ile Gly Thr Ser
    1265                1270                1275

Met Lys Asp Val Leu Ile Gly Asp Ala Gln Ala Asn Thr Leu Met
    1280                1285                1290

Gly Gln Gly Gly Asp Asp Thr Val Arg Gly Gly Asp Gly Asp Asp
    1295                1300                1305

Leu Leu Phe Gly Gly Asp Gly Asn Asp Met Leu Tyr Gly Asp Ala
    1310                1315                1320

Gly Asn Asp Thr Leu Tyr Gly Gly Leu Gly Asp Thr Leu Glu
    1325                1330                1335

Gly Gly Ala Gly Asn Asp Trp Phe Gly Gln Thr Gln Ala Arg Glu
    1340                1345                1350

His Asp Val Leu Arg Gly Gly Asp Gly Val Asp Thr Val Asp Tyr
    1355                1360                1365

Ser Gln Thr Gly Ala His Ala Gly Ile Ala Ala Gly Arg Ile Gly
    1370                1375                1380

Leu Gly Ile Leu Ala Asp Leu Gly Ala Gly Arg Val Asp Lys Leu
    1385                1390                1395

Gly Glu Ala Gly Ser Ser Ala Tyr Asp Thr Val Ser Gly Ile Glu
    1400                1405                1410

Asn Val Val Gly Thr Glu Leu Ala Asp Arg Ile Thr Gly Asp Ala
    1415                1420                1425

Gln Ala Asn Val Leu Arg Gly Ala Gly Gly Ala Asp Val Leu Ala
    1430                1435                1440

Gly Gly Glu Gly Asp Asp Val Leu Leu Gly Gly Asp Gly Asp Asp
    1445                1450                1455

Gln Leu Ser Gly Asp Ala Gly Arg Asp Arg Leu Tyr Gly Glu Ala
    1460                1465                1470
```

| | | | | | | | | | | |
|---|---|---|---|---|---|---|---|---|---|---|
| Gly | Asp | Asp | Trp | Phe | Phe | Gln | Asp | Ala | Ala | Asn | Ala | Gly | Asn | Leu |
| | 1475 | | | | 1480 | | | | 1485 | |

| Leu | Asp | Gly | Gly | Asp | Gly | Arg | Asp | Thr | Val | Asp | Phe | Ser | Gly | Pro |
|---|---|---|---|---|---|---|---|---|---|---|---|---|---|---|
| | 1490 | | | | 1495 | | | | 1500 | |

| Gly | Arg | Gly | Leu | Asp | Ala | Gly | Ala | Lys | Gly | Val | Phe | Leu | Ser | Leu |
|---|---|---|---|---|---|---|---|---|---|---|---|---|---|---|
| | 1505 | | | | 1510 | | | | 1515 | |

| Gly | Lys | Gly | Phe | Ala | Ser | Leu | Met | Asp | Glu | Pro | Glu | Thr | Ser | Asn |
|---|---|---|---|---|---|---|---|---|---|---|---|---|---|---|
| | 1520 | | | | 1525 | | | | 1530 | |

| Val | Leu | Arg | Asn | Ile | Glu | Asn | Ala | Val | Gly | Ser | Ala | Arg | Asp | Asp |
|---|---|---|---|---|---|---|---|---|---|---|---|---|---|---|
| | 1535 | | | | 1540 | | | | 1545 | |

| Val | Leu | Ile | Gly | Asp | Ala | Gly | Ala | Asn | Val | Leu | Asn | Gly | Leu | Ala |
|---|---|---|---|---|---|---|---|---|---|---|---|---|---|---|
| | 1550 | | | | 1555 | | | | 1560 | |

| Gly | Asn | Asp | Val | Leu | Ser | Gly | Gly | Ala | Gly | Asp | Val | Leu | Leu |
|---|---|---|---|---|---|---|---|---|---|---|---|---|---|
| | 1565 | | | | 1570 | | | | 1575 | |

| Gly | Asp | Glu | Gly | Ser | Asp | Leu | Leu | Ser | Gly | Asp | Ala | Gly | Asn | Asp |
|---|---|---|---|---|---|---|---|---|---|---|---|---|---|---|
| | 1580 | | | | 1585 | | | | 1590 | |

| Asp | Leu | Phe | Gly | Gly | Gln | Gly | Asp | Asp | Thr | Tyr | Leu | Phe | Gly | Val |
|---|---|---|---|---|---|---|---|---|---|---|---|---|---|---|
| | 1595 | | | | 1600 | | | | 1605 | |

| Gly | Tyr | Gly | His | Asp | Thr | Ile | Tyr | Glu | Ser | Gly | Gly | His | Asp |
|---|---|---|---|---|---|---|---|---|---|---|---|---|---|
| | 1610 | | | | 1615 | | | | 1620 | |

| Thr | Ile | Arg | Ile | Asn | Ala | Gly | Ala | Asp | Gln | Leu | Trp | Phe | Ala | Arg |
|---|---|---|---|---|---|---|---|---|---|---|---|---|---|---|
| | 1625 | | | | 1630 | | | | 1635 | |

| Gln | Gly | Asn | Asp | Leu | Glu | Ile | Arg | Ile | Leu | Gly | Thr | Asp | Asp | Ala |
|---|---|---|---|---|---|---|---|---|---|---|---|---|---|---|
| | 1640 | | | | 1645 | | | | 1650 | |

| Leu | Thr | Val | His | Asp | Trp | Tyr | Arg | Asp | Ala | Asp | His | Arg | Val | Glu |
|---|---|---|---|---|---|---|---|---|---|---|---|---|---|---|
| | 1655 | | | | 1660 | | | | 1665 | |

| Ile | Ile | His | Ala | Ala | Asn | Gln | Ala | Val | Asp | Gln | Ala | Gly | Ile | Glu |
|---|---|---|---|---|---|---|---|---|---|---|---|---|---|---|
| | 1670 | | | | 1675 | | | | 1680 | |

| Lys | Leu | Val | Glu | Ala | Met | Ala | Gln | Tyr | Pro | Asp | Pro | Gly | Ala | Ala |
|---|---|---|---|---|---|---|---|---|---|---|---|---|---|---|
| | 1685 | | | | 1690 | | | | 1695 | |

| Ala | Ala | Ala | Pro | Pro | Ala | Ala | Arg | Val | Pro | Asp | Thr | Leu | Met | Gln |
|---|---|---|---|---|---|---|---|---|---|---|---|---|---|---|
| | 1700 | | | | 1705 | | | | 1710 | |

| Ser | Leu | Ala | Val | Asn | Trp | Arg |
|---|---|---|---|---|---|---|
| | 1715 | | | | 1720 | |

```
<210> SEQ ID NO 5
<211> LENGTH: 8825
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
cggaagagcg cccaatacgc aaaccgcctc tccccgcgcg ttggccgatt cattaatgca      60
gctggcacga caggtttccc gactggaaag cgggcagtga gcgcaacgca attaatgtga     120
gttagctcac tcattaggca ccccaggctt tacactttat gcttccggct cgtatgttgt     180
gtggaattgt gagcggataa caatttcaca caggaaacag ctatgaccat gattacgaat     240
ttaatacgac tcactatagg gaaagctcta gaaataattt tgtttaactt taagaaggag     300
atatacatat gcttccgtcc gcccaagcgc cctccctcct caatcccacc gacgacttcg     360
cggcactggg caatattgcc tggctgtgga tgaactctcc catgcaccgc gactggccgg     420
tgcatctgct cgcacgcaac acgctcgcgc gattcaact gggccaatac attctgctgc     480
gatgcaatga cgtgccggtt gcatactgca gctgggccct aatggacgcc gacaccgaac     540
```

```
tctcctatgt catggcgccc tcgtcgctgg gcgggaatgc ctggaactgc ggcgaccgac    600
tgtggatcat cgactggatc gcgccattct cgcgcgacga caatcgtgcg ctgcgccgcg    660
cgctggccga acggcacccc gacagcgtgg gccgttcgct gcgcgttcgg cgcggcggcg    720
acaccgcgcg cgtcaaggag taccgaggcc gcgcgctgga cgcggccgcc actcgcgcgc    780
agctggaccg ctaccatgcc gaactgatcg caggactgcg cgcgagcaac ggcggatacg    840
cgccgcgagg ccggggcacc gcctaaggat cctctagagc ttgcatgccc tggcacgaca    900
ggtttcccga ctggaaagcg ggcagtgagc gcaacgcaat taatgtgagt tagctcactc    960
attaggcacc ccaggcttta cactttatgc ttccggctcg tatgttgtgt ggaattgtga   1020
gcggataaca atttcacaca ggaaacagct atgaccatgc agcaatcgca tcaggctggt   1080
tacgcaaacg ccgccgaccg ggagtctggc atccccgcag ccgtactcga tggcatcaag   1140
gccgtggcga aggaaaaaaa cgccacattg atgttccgcc tggtcaaccc ccattccacc   1200
agcctgattg ccgaaggggt ggccaccaaa ggattgggcg tgcacgccaa gtcgtccgat   1260
tgggggttgc aggcgggcta cattcccgtc aacccgaatc tttccaaact gttcggccgt   1320
gcgcccgagg tgatcgcgcg gccgacaac gacgtcaaca gcagcctggc gcatggccat   1380
accgcggtcg acctgacgct gtcgaaagag cggcttgact atctgcggca agcgggcctg   1440
gtcaccggca tggccgatgg cgtggtcgcg agcaaccacg caggctacga gcagttcgag   1500
tttcgcgtga aggaaacctc ggacgggcgc tatgccgtgc agtatcgccg caagggcggc   1560
gacgatttcg aggcggtcaa ggtgatcggc aatgccgccg gtattccact gacggcggat   1620
ggatccatcg acatgttcgc cattatgccg catctgtcca acttccgcga ctcggcgcgc   1680
agttcggtga ccagcggcga ttcggtgacc gattacctgg cgcgcacgcg gcgggccgcc   1740
agcgaggcca cgggcggtgt acacctggat cgcgaacgca tcgacttgtt gtggaaaatc   1800
gctcgcgccg cgcgccgttc cgcagtgggc accgaggcgc gtcgccagtt ccgctacgac   1860
ggcgacatga atatcggcgt gatcaccgat ttcgagctgg aagtgcgcaa tgcgctgaac   1920
aggcgggcgc acgccgtcgg cgcgcaggac gtggtccagc atggcactga gcagaacaat   1980
cctttccggg aggcagatga aagatttttc gtcgtatcgg ccaccggtga agccagatg    2040
ctcacgcgcg ggcaactgaa ggaatacatt ggccagcagc gcggcgaggg ctatgtcttc   2100
tacgagaacc gtgcatacgg cgtggcgggg aaaagcctgt cgacgatgg gctgggagcc    2160
gcgcccggcg tgccgagcgg acgttcgaag ttctcgccgg atgtactgga aacggtgccg   2220
gcgtcacccg gattgcggcg gccgtcgctg ggcgcagtgg aacgccagga ttccggctat   2280
gacagccttg atggggtggg atcgcgatcg ttctcgttgg gcgaggtgtc cgacatggcc   2340
gccgtggaag cggcggaact ggaaatgacc cggcaagtct gcacgccgg ggcgcggcag    2400
gacgatgccg agccgggcgt gagcggtgcg tcggcgcact gggggcagcg ggcgctgcag   2460
ggcgccagg cggtggcggc ggcgcagcgg ctggttcatg ccattgccct gatgacgcaa    2520
ttcggccggg ccggttccac caacacgccg caggaagcgg cctcgttgtc ggcggccgtg   2580
ttcggcttgg gcgaggccag cagcgccgtg gccgaaaccg tgagcggttt tttccgcggg   2640
tcttcgcgct gggccggcgg tttcggcgtg gctggcggcg cgatggcgct gggaggcggc   2700
atcgccgcgg ccgttggcgc cgggatgtcg ttgaccgatg acgcgccggc cggacagaag   2760
gccgccgccg gagctccgat cgcgctgcag ttaacgggtg gaacggtcga gctggcttct   2820
tccatccgcg tggcgctggc cgcggcgcgc ggcgtgacca gcggcttgca ggtgccgggg   2880
gcgtcggccg gggcggctgc cggcgcattg gccgcggcgc tcagtcccat ggagatctac   2940
```

```
ggcctggtgc agcaatcgca ctatgcggat cagctggaca agctggcgca ggaatcgagc      3000
gcatacggtt acgagggcga cgccttgctg gcccagctgt atcgcgacaa gacggccgcc      3060
gagggcgccg tcgccggcgt ctccgccgtc ctgagcacgg tgggggcggc ggtgtcgatc      3120
gccgcggcgg ccagcgtggt aggggccccg gtggcggtgg tcacttcctt gctgaccggg      3180
gctctcaacg gcatcctgcg cggcgtgcag cagcccatca tcgaaaagct ggccaacgat      3240
tacgctcgca agatcgacga gctgggcggg ccgcaagcgt acttcgagaa aaacctgcag      3300
gcgcgtcacg aacaactggc caattcggac ggcctacgga aaatgctggc cgacctgcag      3360
gccggttgga acgccagcag cgtgatcggg gtgcagacga cagagatctc caagtcgggcg     3420 ctcgaactgg ccgccattac cggcaacgcg acaacctga atccgtcga cgtgttcgtg       3480 gaccgcttcg tccagggcga gcgggtgccc ggccagccgg tggtcctcga cgtcgccgcc      3540
ggcggcatcg atatcgccag ccgcaagggc gagcggccgg cgctgacgtt catcacgccg      3600
ctggccgcgc caggagaaga gcagcgccgg cgcacgaaaa cgggcagatc tgaattcacc      3660
acattcgtcg agatcgtggg caagcaggac cgctggcgca tccgggacgg cgcggccgac      3720
accaccatcg atctggccaa ggtggtgtcg caactggtcg acgccaatgg cgtgctcaag      3780
cacagcatca aactggatgt gatcggcgga gatggcgatg acgtcgtgct tgccaatgct      3840
tcgcgcatcc attatgacgg cggcgcgggc accaacacgg tcagctatgc cgccctgggt      3900
cgacaggatt ccattaccgt gtccgccgac ggggaacgtt tcaacgtgcg caagcagttg      3960
aacaacgcca acgtgtatcg cgaaggcgtg gctacccaga caaccgccta cggcaagcgc      4020
acggagaatg tccaataccg ccatgtcgag ctggcccgtg tcgggcaagt ggtggaggtc      4080
gacacgctcg agcatgtgca gcacatcatc ggcggggccg gcaacgattc gatcaccggc      4140
aatgcgcacg acaacttcct agccggcggg tcggcgacg acaggctgga tggcggcgcc      4200
ggcaacgaca ccctggttgg cggcgagggc caaaacacgg tcatcggcgg cgccggcgac      4260
gacgtattcc tgcaggacct gggggtatgg agcaaccagc tcgatggcgg cgcgggcgtc      4320
gataccgtga agtacaacgt gcaccagcct tccgaggagc gcctcgaacg catgggcgac      4380
acgggcatcc atgccgatct tcaaaagggc acggtcgaga agtggccggc cctgaacctg      4440
ttcagcgtcg accatgtcaa gaatatcgag atctgcacg gctcccgcct aaacgaccgc      4500
atcgccggcg acgaccagga caacgagctc tggggccacg atggcaacga cacgatacgc      4560
ggccggggcg gcgacgacat cctgcgcggc ggcctgggcc tggacacgct gtatggcgag      4620
gacggcaacg acatcttcct gcaggacgac gagaccgtca gcgatgacat cgacggcggc      4680
gcggggctgg acaccgtcga ctactccgcc atgatccatc caggcaggat cgttgcgccg      4740
catgaatacg gcttcgggat cgaggcggac ctgtccaggg aatgggtgcg caaggcgtcc      4800
gcgctgggcg tggactatta cgataatgtc cgcaatgtcg aaaacgtcat cggtacgagc      4860
atgaaggatg tgctcatcgg cgacgcgcaa gccaataccc tgatgggcca gggcggcgac      4920
gataccgtgc gcgcggcga cggcgatgat ctgctgttcg gcggcgacgg caacgacatg      4980
ctgtatggcg acgccggcaa cgacaccctc tacgggggc tgggcgacga tacccttgaa      5040
ggcggcgcgg gcaacgattg gttcggccag acgcaggcgc gcgagcatga cgtgctgcgc      5100
ggcggagatg ggtggatac cgtcgattac agccagaccg cgcgcatgc cggcattgcc      5160 gcgggtcgca tcgggctggg catcctggct gacctgggcg ccggccgcgt cgacaagctg      5220
ggcgaggccg gcagcagcgc ctacgatacg gtttccggta tcgagaacgt ggtgggcacg      5280
gaactggccg accgcatcac gggcgatgcg caggccaacg tgctgcgcgg cgcgggtggc      5340
```

-continued

```
gccgacgtgc ttgcgggcgg cgagggcgac gatgtgctgc tgggcggcga cggcgacgac    5400
cagctgtcgg gcgacgccgg acgcgatcgc ttgtacggcg aagccggtga cgactggttc    5460
ttccaggatg ccgccaatgc cggcaatctg ctcgacggcg cgacggccg cgataccgtg     5520 gatttcagcg gcccgggccg gggcctcgac gccggcgcaa agggcgtatt cctgagcttg    5580
ggcaaggggt tcgccagcct gatggacgaa cccgaaacca gcaacgtgtt gcgcaatatc    5640
gagaacgccg tgggcagcgc gcgtgatgac gtgctgatcg gcgacgcagg cgccaacgtc    5700
ctcaatggcc tggcgggcaa cgacgtgctg tccggcggcg ctggcgacga tgtgctgctg    5760
ggcgacgagg gctcggacct gctcagcggc gatgcgggca acgacgatct gttcggcggg    5820
cagggcgatg atacttatct gttcggggtc gggtacgggc acgacacgat ctacgaatcg    5880
ggcggcggcc atgacaccat ccgcatcaac gcggggcgg accagctgtg gttcgcgcgc     5940
cagggcaacg acctggagat ccgcattctc ggcaccgacg atgcacttac cgtgcacgac    6000
tggtatcgcg acgccgatca ccgggtggaa atcatccatg ccgccaacca ggcggtagac    6060
caggcaggca tcgaaaagct ggtcgaggca atggcgcagt atccggaccc cggcgcggcg    6120
gcggctgccc cgccggcggc gcgcgtgccg gacacgctga tgcagtccct ggctgtcaac    6180
tggcgctgaa gcgccgtgaa tcacggcccg cctgcctcgc gcggcggcgc cgtctctttg    6240
cgttcttctc cgaggtattt cccatcatga attcactggc cgtcgtttta caacgtcgtg    6300
actgggaaaa ccctggcgtt acccaactta atcgccttgc agcacatccc cctttcgcca    6360
gctggcgtaa tagcgaagag gcccgcaccg atcgcccttc ccaacagttg cgcagcctga    6420
atggcgaatg ggaaattgta aacgttaata ttttgttaat attttgttaa aattcgcgtt    6480
aaatttttgt taaatcagct cattttttaa ccaataggcc gaaatcggca aaatccctta    6540
taaatcaaaa gaatagaccg agatagggtt gagtgttgtt ccagtttgga acaagagtcc    6600
actattaaag aacgtggact ccaacgtcaa agggcgaaaa accgtctatc agggcgatgg    6660
cccactacgt gaaccatcac cctaatcaag ttttttgggg tcgaggtgcc gtaaagcact    6720
aaatcggaac cctaaaggga tgccccgatt tagagcttga cggggaaagc cggcgaacgt    6780
ggcgagaaag gaagggaaga aagcgaaagg agcgggcgct agggcgctgg caagtgtagc    6840
ggtcacgctg cgcgtaacca ccacacccgc cgcgcttaat gcgccgctac agggcgcgtc    6900
aggtggcact tttcggggaa atgtgcgcgg aaccccctatt tgtttatttt tctaaataca    6960
ttcaaatatg tatccgctca tgagacaata accctgataa atgcttcaat aatattgaaa    7020
aaggaagagt atgagtattc aacatttccg tgtcgccctt attccctttt ttgcggcatt    7080
ttgccttcct gttttgctc acccagaaac gctggtgaaa gtaaaagatg ctgaagatca     7140
gttgggtgca cgagtgggtt acatcgaact ggatctcaac agcggtaaga tccttgagag    7200
ttttcgcccc gaagaacgtt ttccaatgat gagcactttt aaagttctgc tatgtggcgc    7260
ggtattatcc cgtattgacg ccgggcaaga gcaactcggt cgccgcatac actattctca    7320
gaatgacttg gttgagtact caccagtcac agaaaagcat cttacggatg gcatgacagt    7380
aagagaatta tgcagtgctg ccataaccat gagtgataac actgcggcca acttacttct    7440
gacaacgatc ggaggaccga aggagctaac cgcttttttg cacaacatgg ggatcatgt     7500 aactcgcctt gatcgttggg aaccggagct gaatgaagcc ataccaaacg acgagcgtga    7560
caccacgatg cctgtagcaa tggcaacaac gttgcgcaaa ctattaactg gcgaactact    7620
tactctagct tcccggcaac aattaataga ctggatggag gcggataaag ttgcaggacc    7680
acttctgcgc tcggcccttc cggctggctg gtttattgct gataaatctg gagccggtga    7740
```

```
gcgtgggtct cgcggtatca ttgcagcact ggggccagat ggtaagccct cccgtatcgt    7800
agttatctac acgacgggga gtcaggcaac tatggatgaa cgaaatagac agatcgctga    7860
gataggtgcc tcactgatta agcattggta actgtcagac caagtttact catatatact    7920
ttagattgat ttaaaacttc attttaatt taaaaggatc taggtgaaga tcctttttga     7980
taatctcatg accaaaatcc cttaacgtga gttttcgttc cactgagcgt cagacccgt     8040 agaaaagatc aaaggatctt cttgagatcc ttttttctg cgcgtaatct gctgcttgca     8100
aacaaaaaaa ccaccgctac cagcggtggt ttgtttgccg gatcaagagc taccaactct    8160
ttttccgaag gtaactggct tcagcagagc gcagatacca aatactgtcc ttctagtgta    8220
gccgtagtta ggccaccact tcaagaactc tgtagcaccg cctacatacc tcgctctgct    8280
aatcctgtta ccagtggctg ctgccagtgg cgataagtcg tgtcttaccg ggttggactc    8340
aagacgatag ttaccggata aggcgcagcg gtcgggctga acggggggtt cgtgcacaca    8400
gcccagcttg gagcgaacga cctacaccga actgagatac ctacagcgtg agctatgaga    8460
aagcgccacg cttcccgaag ggagaaaggc ggacaggtat ccggtaagcg gcagggtcgg    8520
aacaggagag cgcacgaggg agcttccagg gggaaacgcc tggtatcttt atagtcctgt    8580
cgggtttcgc cacctctgac ttgagcgtcg attttgtga tgctcgtcag ggggggggag      8640
cctatggaaa aacgccagca acgcggcctt tttacggttc ctggccttt gctgcctt       8700 tgctcacatg ttctttcctg cgttatcccc tgattctgtg ataaccgta ttaccgcctt      8760 tgagtgagct gataccgctc gccgcagccg aacgaccgag cgcagcgagt cagtgagcga    8820
ggaag                                                                 8825

<210> SEQ ID NO 6
<211> LENGTH: 8855
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
cggaagagcg cccaatacgc aaaccgcctc tccccgcgcg ttggccgatt cattaatgca      60
gctggcacga caggttttcc cgactggaaag cgggcagtga gcgcaacgca attaatgtga    120
gttagctcac tcattaggca ccccaggctt tacactttat gcttccggct cgtatgttgt     180
gtggaattgt gagcggataa caatttcaca caggaaacag ctatgaccat gattacgaat     240
ttaatacgac tcactatagg gaaagctcta gaaataattt tgtttaactt taagaaggag    300
atatacatat gcttccgtcc gcccaagcgc cctccctcct caatcccacc gacgacttcg     360
cggcactggg caatattgcc tggctgtgga tgaactctcc catgcaccgc gactggccgg    420
tgcatctgct cgcacgcaac acgctcgcgc gattcaact gggccaatac attctgctgc     480
gatgcaatga cgtgccggtt gcatactgca gctgggccct aatggacgcc gacaccgaac    540
tctcctatgt catggcgccc tcgtcgctgg gcgggaatgc ctggaactgc ggcgaccgac    600
tgtggatcat cgactggatc gcgccattct cgcgcgacga caatcgtgcg ctgcgccgcg    660
cgctggccga acggcacccc gacagcgtgg ccgttcgct gcgcgttcgg cgcggcggcg     720
acaccgcgcg cgtcaaggag taccgaggcc gcgcgctgga cgcggccgcc actcgcgcgc    780
agctggaccg ctaccatgcc gaactgatcg caggactgcg cgcgagcaac ggcggatacg     840
cgccgcgagg ccggggcacc gcctaaggat cctctagagc ttgcatgccc tggcacgaca    900
ggtttcccga ctggaaagcg gcagtgagc gcaacgcaat taatgtgagt tagctcactc    960
```

```
attaggcacc ccaggcttta cactttatgc ttccggctcg tatgttgtgt ggaattgtga      1020
gcggataaca atttcacaca ggaaacagct atgaccatgc agcaatcgca tcaggctggt      1080
tacgcaaacg ccgccgaccg ggagtctggc atccccgcag ccgtactcga tggcatcaag      1140
gccgtggcga aggaaaaaaa cgccacattg atgttccgcc tggtcaaccc ccattccacc      1200
agcctgattg ccgaagggt ggccaccaaa ggattgggcg tgcacgccaa gtcgtccgat       1260
tgggggttgc aggcgggcta cattcccgtc aacccgaatc ttccaaaact gttcggccgt      1320
gcgcccgagg tgatcgcgcg ggccgacaac gacgtcaaca gcagcctggc gcatggccat      1380
accgcggtcg acctgacgct gtcgaaagag cggcttgact atctgcggca agcgggcctg      1440
gtcaccggca tggccgatgg cgtggtcgcg agcaaccacg caggctacga gcagttcgag      1500
tttcgcgtga aggaaacctc ggacgggcgc tatgccgtgc agtatcgccg caagggcggc      1560
gacgatttcg aggcggtcaa ggtgatcggc aatgccgccg gtattccact gacggcggat      1620
ggatccatcg acatgttcgc cattatgccg catctgtcca acttccgcga ctcggcgcgc      1680
agttcggtga ccagcggcga ttcggtgacc gattacctgg cgcgcacgcg gcgggccgcc      1740
agcgaggcca cgggcggtgt actctcaata attaatttcg aaaagcttgt acacctggat      1800
cgcgaacgca tcgacttgtt gtggaaaatc gctcgcgccg gcgcccgttc cgcagtgggc      1860
accgaggcgc gtcgccagtt ccgctacgac ggcgacatga atatcggcgt gatcaccgat      1920
ttcgagctgg aagtgcgcaa tgcgctgaac aggcgggcgc acgccgtcgg cgcgcaggac      1980
gtggtccagc atggcactga gcagaacaat ccttttcccgg aggcagatga gaagattttc     2040
gtcgtatcgg ccaccggtga aagccagatg ctcacgcgcg gcaactgaa ggaatacatt       2100 ggccagcagc gcggcgaggg ctatgtcttc tacgagaacc gtgcatacgg cgtggcgggg      2160
aaaagcctgt tcgacgatgg gctgggagcc gcgcccggcg tgccgagcgg acgttcgaag      2220
ttctcgccgg atgtactgga aacggtgccg gcgtcacccg gattgcggcg gccgtcgctg      2280
ggcgcagtgg aacgccagga ttccggctat gacagccttg atggggtggg atcgcgatcg      2340
ttctcgttgg gcgaggtgtc cgacatggcc gccgtggaag cggcggaact ggaaatgacc      2400
cggcaagtct tgcacgccgg ggcgcggcag gacgatgccg agccgggcgt gagcggtgcg      2460
tcggcgcact ggggggcagcg ggcgctgcag ggcgcccagg cggtggcggc ggcgcagcgg      2520
ctggttcatg ccattgccct gatgacgcaa ttcggccggg ccggttccac caacacgccg      2580
caggaagcgg cctcgttgtc ggcggccgtg ttcggcttgg gcgaggccag cagcgccgtg      2640
gccgaaaccg tgagcggttt ttttccgcggg tcttcgcgct gggccggcgg tttcggcgtg      2700
gctggcggcg cgatgcgct gggaggcggc atcgccgcgg ccgttggcgc cgggatgtcg       2760
ttgaccgatg acgcgccggc cggacagaag gccgccgccg gagctccgat cgcgctgcag      2820
ttaacgggtg gaacggtcga gctggcttct tccatcgcgt tggcgctggc cgcggcgcgc      2880
ggcgtgacca gcggcttgca ggtggccggg gcgtcggccg gggcggctgc cggcgcattg      2940
gccgcggcgc tcagtcccat ggagatctac ggcctggtgc agcaatcgca ctatgcggat      3000
cagctggaca agctggcgca ggaatcgagc gcatacggtt acgagggcga cgccttgctg      3060
gcccagctgt atcgcgacaa gacggccgcc gagggcgccg tcgccggcgt ctccgccgtc      3120
ctgagcacgg tggggcggc ggtgtcgatc ccgcggcggg ccagcgtggt aggggccccg       3180
gtggcggtgg tcacttcctt gctgaccggg gctctcaacg gcatcctgcg cggcgtgcag      3240
cagcccatca tcgaaaagct ggccaacgat tacgctcgca agatcgacga gctgggcggg      3300
ccgcaagcgt acttcgagaa aaacctgcag gcgcgtcacg aacaactggc caattcggac      3360
```

```
ggcctacgga aaatgctggc cgacctgcag gccggttgga acgccagcag cgtgatcggg    3420
gtgcagacga cagagatctc caagtcggcg ctcgaactgg ccgccattac cggcaacgcg    3480
gacaacctga aatccgtcga cgtgttcgtg gaccgcttcg tccagggcga gcgggtggcc    3540
ggccagccgg tggtcctcga cgtcgccgcc ggcggcatcg atatcgccag ccgcaagggc    3600
gagcggccgg cgctgacgtt catcacgccg ctggccgcgc caggagaaga gcagcgccgg    3660
cgcacgaaaa cgggcagatc tgaattcacc acattcgtcg agatcgtggg caagcaggac    3720
cgctggcgca tccgggacgg cgcggccgac accaccatcg atctggccaa ggtggtgtcg    3780
caactggtcg acgccaatgg cgtgctcaag cacagcatca aactggatgt gatcggcgga    3840
gatggcgatg acgtcgtgct tgccaatgct tcgcgcatcc attatgacgg cggcgcgggc    3900
accaacacgg tcagctatgc cgccctgggt cgacaggatt ccattaccgt gtccgccgac    3960
ggggaacgtt tcaacgtgcg caagcagttg aacaacgcca acgtgtatcg cgaaggcgtg    4020
gctacccaga caaccgccta cggcaagcgc acggagaatg tccaataccg ccatgtcgag    4080
ctggcccgtg tcgggcaagt ggtggaggtc gacacgctcg agcatgtgca gcacatcatc    4140 ggcgggccg gcaacgattc gatcaccggc aatgcgcacg acaacttcct agccggcggg    4200
tcgggcgacg acaggctgga tggcggcgcc ggcaacgaca ccctggttgg cggcgagggc    4260
caaaacacgg tcatcggcgg cgccggcgac gacgtattcc tgcaggacct gggggtatgg    4320
agcaaccagc tcgatggcgg cgcgggcgtc gataccgtga agtacaacgt gcaccagcct    4380
tccgaggagc gcctcgaacg catgggcgac acgggcatcc atgccgatct tcaaaagggc    4440
acggtcgaga agtggccggc cctgaacctg ttcagcgtcg accatgtcaa gaatatcgag    4500
aatctgcacg gctcccgcct aaacgaccgc atcgccggcg acgaccagga caacgagctc    4560
tggggccacg atggcaacga cacgatacgc ggccggggcg gcgacgacat cctgcgcggc    4620
ggcctgggcg tggacacgct gtatggcgag acggcaacg acatcttcct gcaggacgac    4680
gagaccgtca gcgatgacat cgacggcggc gcggggctgg acaccgtcga ctactccgcc    4740
atgatccatc caggcaggat cgttgcgccg catgaatacg gcttcgggat cgaggcggac    4800
ctgtccaggg aatgggtgcg caaggcgtcc gcgctgggcg tggactatta cgataatgtc    4860
cgcaatgtcg aaaacgtcat cggtacgagc atgaaggatg tgctcatcgg cgacgcgcaa    4920
gccaataccc tgatgggcca gggcggcgac gataccgtgc gcggcggcga cggcgatgat    4980
ctgctgttcg gcggcgacgg caacgacatg ctgtatggcg acgccggcaa cgacaccctc    5040
tacggggggc tgggcgacga tacccttgaa ggcggcgcgg gcaacgattg gttcggccag    5100
acgcaggcgc gcgagcatga cgtgctgcgc ggcggagatg gggtggatac cgtcgattac    5160
agccagaccg gcgcgcatgc cggcattgcc gcgggtcgca tcgggctggg catcctggct    5220
gacctgggcg ccggccgcgt cgacaagctg ggcgaggccg gcagcagcgc ctacgatacg    5280
gtttccggta tcgagaacgt ggtgggcacg gaactggccg accgcatcac gggcgatgcg    5340
caggccaacg tgctgcgcgg cgcgggtggc gccgacgtgc ttgcgggcgg cgagggcgac    5400
gatgtgctgc tgggcggcga cggcgacgac cagctgtcgg gcgacgccgg acgcgatcgc    5460
ttgtacggcg aagccggtga cgactggttc ttccaggatg ccgccaatgc cggcaatctg    5520
ctcgacggcg gcgacggccg cgataccgtg gatttcagcg gcccgggccg gggcctcgac    5580
gccggcgcaa agggcgtatt cctgagcttg gcaagggggt tcgccagcct gatggacgaa    5640
cccgaaacca gcaacgtgtt gcgcaatatc gagaacgccg tgggcagcgc gcgtgatgac    5700
gtgctgatcg gcgacgcagg cgccaacgtc tcaatggcc tggcgggcaa cgacgtgctg    5760
```

```
tccggcggcg ctggcgacga tgtgctgctg ggcgacgagg gctcggacct gctcagcggc   5820
gatgcgggca acgacgatct gttcggcggg cagggcgatg atacttatct gttcggggtc   5880
gggtacgggc acgacacgat ctacgaatcg ggcggcggcc atgacaccat ccgcatcaac   5940 gcggggggcgg accagctgtg gttcgcgcgc cagggcaacg acctggagat ccgcattctc   6000
ggcaccgacg atgcacttac cgtgcacgac tggtatcgcg acgccgatca ccgggtggaa   6060
atcatccatg ccgccaacca ggcggtagac caggcaggca tcgaaaagct ggtcgaggca   6120
atggcgcagt atccggaccc cggcgcgcg cggctgccc cgccggcggc gcgcgtgccg      6180
gacacgctga tgcagtccct ggctgtcaac tggcgctgaa gcgccgtgaa tcacggcccg   6240
cctgcctcgc gcggcggcgc cgtctctttg cgttcttctc cgaggtattt cccatcatga   6300
attcactggc cgtcgtttta caacgtcgtg actgggaaaa ccctggcgtt acccaactta   6360
atcgccttgc agcacatccc cctttcgcca gctggcgtaa tagcgaagag gcccgcaccg   6420
atcgcccttc ccaacagttg cgcagcctga atggcgaatg gaaattgta aacgttaata   6480 ttttgttaat attttgttaa aattcgcgtt aaattttgt taaatcagct catttttaa    6540 ccaataggcc gaaatcggca aaatccctta taaatcaaaa gaatagaccg agataggtt    6600 gagtgttgtt ccagtttgga acaagagtcc actattaaag aacgtggact ccaacgtcaa   6660
agggcgaaaa accgtctatc agggcgatgg cccactacgt gaaccatcac cctaatcaag   6720
ttttttgggg tcgaggtgcc gtaaagcact aaatcggaac cctaaaggga tgccccgatt   6780
tagagcttga cggggaaagc cggcgaacgt ggcgagaaag gaagggaaga agcgaaagg    6840 agcgggcgct agggcgctgg caagtgtagc ggtcacgctg cgcgtaacca ccacacccgc   6900
cgcgcttaat gcgccgctac agggcgcgtc aggtggcact tttcggggaa atgtgcgcgg   6960
aacccctatt tgtttatttt tctaaataca ttcaaatatg tatccgctca tgagacaata   7020
accctgataa atgcttcaat aatattgaaa aaggaagagt atgagtattc aacatttccg   7080
tgtcgccctt attccctttt ttgcggcatt ttgccttcct gttttgctc acccagaaac    7140 gctggtgaaa gtaaaagatg ctgaagatca gttgggtgca cgagtgggtt acatcgaact   7200
ggatctcaac agcggtaaga tccttgagag ttttcgcccc gaagaacgtt ttccaatgat   7260
gagcactttt aaagttctgc tatgtggcgc ggtattatcc cgtattgacg ccgggcaaga   7320
gcaactcggt cgccgcatac actattctca gaatgacttg gttgagtact caccagtcac   7380
agaaaagcat cttacggatg gcatgacagt aagagaatta tgcagtgctg ccataaccat   7440
gagtgataac actgcggcca acttacttct gacaacgatc ggaggaccga aggagctaac   7500
cgcttttttg cacaacatgg gggatcatgt aactcgcctt gatcgttggg aaccggagct   7560
gaatgaagcc ataccaaacg acgagcgtga caccacgatg cctgtagcaa tggcaacaac   7620
gttgcgcaaa ctattaactg gcgaactact tactctagct tcccggcaac aattaataga   7680
ctggatggag gcggataaag ttgcaggacc acttctgcgc tcggcccttc cggctggctg   7740
gtttattgct gataaatctg gagccggtga gcgtgggtct cgcggtatca ttgcagcact   7800
ggggccagat ggtaagccct cccgtatcgt agttatctac acgacgggga gtcaggcaac   7860
tatggatgaa cgaaatagac agatcgctga gataggtgcc tcactgatta agcattggta   7920
actgtcagac caagtttact catatatact ttagattgat ttaaaacttc attttttaatt  7980 taaaaggatc taggtgaaga tcctttttga atctcatg accaaaatcc cttaacgtga    8040
gttttcgttc cactgagcgt cagacccgt agaaaagatc aaaggatctt cttgagatcc    8100
tttttttctg cgcgtaatct gctgcttgca acaaaaaaa ccaccgctac cagcggtggt   8160
```

```
ttgtttgccg gatcaagagc taccaactct ttttccgaag gtaactggct tcagcagagc    8220
gcagatacca aatactgtcc ttctagtgta gccgtagtta ggccaccact tcaagaactc    8280
tgtagcaccg cctacatacc tcgctctgct aatcctgtta ccagtggctg ctgccagtgg    8340
cgataagtcg tgtcttaccg ggttggactc aagacgatag ttaccggata aggcgcagcg    8400
gtcgggctga acgggggtt cgtgcacaca gcccagcttg gagcgaacga cctacaccga    8460
actgagatac ctacagcgtg agctatgaga aagcgccacg cttcccgaag ggagaaaggc    8520
ggacaggtat ccggtaagcg cagggtcgg aacaggagag cgcacgaggg agcttccagg    8580
gggaaacgcc tggtatcttt atagtcctgt cgggtttcgc cacctctgac ttgagcgtcg    8640
atttttgtga tgctcgtcag gggggcggag cctatggaaa aacgccagca acgcggcctt    8700
tttacggttc ctggcctttt gctggccttt tgctcacatg ttctttcctg cgttatcccc    8760
tgattctgtg gataaccgta ttaccgcctt tgagtgagct gataccgctc gccgcagccg    8820
aacgaccgag cgcagcgagt cagtgagcga ggaag                              8855
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gggggacgat cgtcgggggg                                                20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tccatgacgt tcctgacgtt                                                20

<210> SEQ ID NO 9
<211> LENGTH: 8
<212> TYPE: PRT
<213> ORGANISM: Unknown
<220> FEATURE:
<223> OTHER INFORMATION: Description of Unknown: Ova peptide

<400> SEQUENCE: 9

Ser Ile Ile Asn Phe Glu Lys Leu
1               5

<210> SEQ ID NO 10
<211> LENGTH: 1740
<212> TYPE: PRT
<213> ORGANISM: Bordetella parapertussis

<400> SEQUENCE: 10

Met Leu Asp Val Trp Phe Leu Gln Lys Asp Glu Val Leu Ser Ala Thr
1               5                   10                  15

His Arg Leu Arg Arg Cys Glu Ser Val Gln Ser Thr Thr Tyr Arg Gln
                20                  25                  30

Ile His Met Gln Gln Ser His Gln Ala Gly Tyr Ala Asn Ala Ala Asp
            35                  40                  45

-continued

Arg Glu Ser Gly Ile Pro Ala Ala Val Leu Asp Gly Ile Lys Ala Val
    50                  55                  60

Ala Lys Glu Lys Asn Ala Thr Leu Met Phe Arg Leu Val Asn Pro His
65                  70                  75                  80

Ser Thr Ser Leu Ile Ala Glu Gly Val Ala Thr Lys Gly Leu Gly Val
                85                  90                  95

His Ala Lys Ser Ser Asp Trp Gly Leu Gln Ala Gly Tyr Ile Pro Val
                100                 105                 110

Asn Pro Asn Leu Ser Lys Leu Phe Gly Arg Ala Pro Glu Val Ile Ala
                115                 120                 125

Arg Ala Asp Asn Asp Val Asn Ser Ser Leu Ala His Gly His Thr Ala
    130                 135                 140

Val Asp Leu Thr Leu Ser Lys Glu Arg Leu Asp Tyr Leu Arg Gln Ala
145                 150                 155                 160

Gly Leu Val Thr Gly Met Ala Asp Gly Val Val Ala Ser Asn His Ala
                    165                 170                 175

Gly Tyr Glu Gln Phe Glu Phe Arg Val Lys Glu Thr Ser Asp Gly Arg
                180                 185                 190

Tyr Ala Val Gln Tyr Arg Arg Lys Gly Gly Asp Phe Glu Ala Val
                195                 200                 205

Lys Val Ile Gly Asn Ala Ala Gly Ile Pro Leu Thr Ala Asp Ile Asp
    210                 215                 220

Met Phe Ala Ile Met Pro His Leu Ser Asn Phe Arg Asp Ser Ala Arg
225                 230                 235                 240

Ser Ser Val Thr Ser Gly Asp Ser Val Thr Asp Tyr Leu Ala Arg Thr
                    245                 250                 255

Arg Arg Ala Ala Ser Glu Ala Thr Gly Gly Leu Asp Arg Glu Arg Ile
                260                 265                 270

Asp Leu Leu Trp Lys Ile Ala Arg Ala Gly Ala Arg Ser Ala Val Gly
                275                 280                 285

Thr Glu Ala Arg Arg Gln Phe Arg Tyr Asp Gly Asp Met Asn Ile Gly
    290                 295                 300

Val Ile Thr Asp Phe Glu Leu Glu Val Arg Asn Ala Leu Asn Arg Arg
305                 310                 315                 320

Ala His Ala Val Gly Ala Gln Asp Val Val Gln His Gly Thr Glu Gln
                    325                 330                 335

Asn Asn Pro Phe Pro Glu Ala Asp Glu Lys Ile Phe Val Val Ser Ala
                340                 345                 350

Thr Gly Glu Ser Gln Met Leu Thr Arg Gly Gln Leu Lys Glu Tyr Ile
                355                 360                 365

Gly Gln Gln Arg Gly Glu Gly Tyr Val Phe Tyr Glu Asn Arg Ala Tyr
    370                 375                 380

Gly Val Ala Gly Lys Ser Leu Phe Asp Asp Gly Leu Gly Ala Ala Pro
385                 390                 395                 400

Gly Val Pro Gly Gly Arg Ser Lys Ser Ser Pro Asp Val Leu Glu Thr
                    405                 410                 415

Val Pro Ala Ser Pro Gly Leu Arg Arg Pro Ser Leu Gly Ala Val Glu
                420                 425                 430

Arg Gln Asp Ser Gly Tyr Asp Ser Leu Asp Gly Val Gly Ser Arg Ser
                435                 440                 445

Phe Ser Leu Gly Glu Val Ser Asp Met Ala Ala Val Glu Ala Ala Glu
    450                 455                 460

Leu Glu Met Thr Arg Gln Val Leu His Ala Gly Ala Arg Gln Asp Asp

```
                465                 470                 475                 480
        Ala Glu Pro Gly Val Ser Gly Ala Ser Ala His Trp Gly Gln Arg Ala
                            485                 490                 495
        Leu Gln Gly Ala Gln Ala Val Ala Ala Ala Gln Arg Leu Val His Ala
                            500                 505                 510
        Ile Ala Leu Met Thr Gln Phe Gly Arg Ala Gly Ser Thr Asn Thr Pro
                            515                 520                 525
        Gln Glu Ala Ala Ser Leu Ser Ala Val Phe Gly Leu Gly Glu Ala
            530                 535                 540
        Ser Ser Ala Val Ala Glu Thr Val Ser Gly Phe Phe Arg Gly Ser Ser
        545                 550                 555                 560
        Arg Trp Ala Gly Gly Phe Gly Val Ala Gly Ala Met Ala Leu Gly
                            565                 570                 575
        Gly Gly Ile Ala Ala Ala Val Gly Ala Gly Met Ser Leu Thr Asp Asp
                            580                 585                 590
        Ala Pro Ala Gly Gln Lys Ala Ala Val Gly Ala Glu Ile Ala Leu Gln
                            595                 600                 605
        Leu Thr Gly Gly Thr Val Glu Leu Ala Ser Ser Ile Ala Leu Ala Leu
                            610                 615                 620
        Ala Ala Ala Arg Gly Val Thr Ser Gly Leu Gln Val Ala Gly Ala Ser
        625                 630                 635                 640
        Ala Gly Ala Ala Ala Gly Ala Leu Ala Ala Leu Ser Pro Met Glu
                            645                 650                 655
        Ile Tyr Gly Leu Val Gln Gln Ser His Tyr Ala Asp Gln Leu Asp Lys
                            660                 665                 670
        Leu Ala Gln Glu Ser Ser Ala Tyr Gly Tyr Glu Gly Asp Ala Leu Leu
                            675                 680                 685
        Ala Gln Leu Tyr Arg Asp Lys Thr Ala Ala Glu Gly Ala Val Ala Gly
                            690                 695                 700
        Val Ser Ala Val Leu Ser Thr Val Gly Ala Ala Val Ser Ile Ala Ala
        705                 710                 715                 720
        Ala Ala Ser Val Val Gly Ala Pro Val Ala Val Val Thr Ser Leu Leu
                            725                 730                 735
        Thr Gly Ala Leu Asn Gly Ile Leu Arg Gly Val Gln Gln Pro Ile Ile
                            740                 745                 750
        Glu Lys Leu Ala Asn Asp Tyr Ala Arg Lys Ile Asp Glu Leu Gly Gly
                            755                 760                 765
        Pro Gln Ala Tyr Phe Glu Lys Asn Leu Gln Ala Arg His Glu Gln Leu
                            770                 775                 780
        Ala Asn Ser Asp Gly Leu Arg Lys Met Leu Ala Asp Leu Gln Ala Gly
        785                 790                 795                 800
        Trp Asn Ala Ser Ser Val Ile Gly Val Gln Thr Thr Glu Ile Ser Lys
                            805                 810                 815
        Ser Ala Leu Glu Leu Ala Ala Ile Thr Gly Asn Ala Asp Asn Leu Lys
                            820                 825                 830
        Ser Ala Asp Val Phe Val Asp Arg Phe Ile Gln Gly Glu Arg Val Ala
                            835                 840                 845
        Gly Gln Pro Val Val Leu Asp Val Ala Gly Gly Ile Asp Ile Ala
            850                 855                 860
        Ser Arg Lys Gly Glu Arg Pro Ala Leu Thr Phe Ile Thr Pro Leu Ala
        865                 870                 875                 880
        Ala Pro Gly Glu Glu Gln Arg Arg Arg Thr Lys Thr Gly Lys Ser Glu
                            885                 890                 895
```

-continued

```
Phe Thr Thr Phe Val Glu Ile Val Gly Lys Gln Asp Arg Trp Arg Ile
            900                 905                 910

Arg Asp Gly Ala Ala Asp Thr Thr Ile Asp Leu Ala Lys Val Val Ser
        915                 920                 925

Gln Leu Val Asp Ala Asn Gly Val Leu Lys His Ser Ile Lys Leu Glu
    930                 935                 940

Val Ile Gly Gly Asp Gly Asp Val Val Leu Ala Asn Ala Ser Arg
945                 950                 955                 960

Ile His Tyr Asp Gly Gly Ala Gly Thr Asn Thr Val Ser Tyr Ala Ala
                965                 970                 975

Leu Gly Arg Gln Asp Ser Ile Thr Val Ser Ala Asp Gly Glu Arg Phe
            980                 985                 990

Asn Val Arg Lys Gln Leu Asn Asn Ala Asn Val Tyr Arg Glu Gly Val
        995                 1000                1005

Ala Thr Gln Lys Thr Ala Tyr Gly Lys Arg Thr Glu Asn Val Gln
    1010                1015                1020

Tyr Arg His Val Glu Leu Ala Arg Val Gly Gln Leu Val Glu Val
    1025                1030                1035

Asp Thr Leu Glu His Val Gln His Ile Ile Gly Gly Ala Gly Asn
    1040                1045                1050

Asp Ser Ile Thr Gly Asn Ala His Asp Asn Phe Leu Ala Gly Gly
    1055                1060                1065

Ala Gly Asp Asp Arg Leu Asp Gly Gly Ala Gly Asn Asp Thr Leu
    1070                1075                1080

Val Gly Gly Glu Gly His Asn Thr Val Val Gly Gly Ala Gly Asp
    1085                1090                1095

Asp Val Phe Leu Gln Asp Leu Gly Val Trp Ser Asn Gln Leu Asp
    1100                1105                1110

Gly Gly Ala Gly Val Asp Thr Val Lys Tyr Asn Val His Gln Pro
    1115                1120                1125

Ser Glu Glu Arg Leu Glu Arg Met Gly Asp Thr Gly Ile His Ala
    1130                1135                1140

Asp Leu Gln Lys Gly Thr Val Glu Lys Trp Pro Ala Leu Asn Leu
    1145                1150                1155

Phe Ser Val Asp His Val Lys Asn Ile Glu Asn Leu His Gly Ser
    1160                1165                1170

Ser Leu Asn Asp Ser Ile Ala Gly Asp Arg Asp Asn Glu Leu
    1175                1180                1185

Trp Gly Asp Asp Gly Asn Asp Thr Ile His Gly Arg Gly Gly Asp
    1190                1195                1200

Asp Ile Leu Arg Gly Gly Leu Gly Leu Asp Thr Leu Tyr Gly Glu
    1205                1210                1215

Asp Gly Asn Asp Ile Phe Leu Gln Asp Asp Glu Thr Val Ser Asp
    1220                1225                1230

Asp Ile Asp Gly Gly Ala Gly Leu Asp Thr Val Asp Tyr Ser Ala
    1235                1240                1245

Met Ile His Ala Gly Lys Ile Val Ala Pro His Glu Tyr Gly Phe
    1250                1255                1260

Gly Ile Glu Ala Asp Leu Ser Glu Gly Trp Val Arg Lys Ala Ala
    1265                1270                1275

Arg Arg Gly Met Gly Tyr Tyr Asp Ser Val Arg Ser Val Glu Asn
    1280                1285                1290

Val Ile Gly Thr Ser Met Lys Asp Val Leu Ile Gly Asp Ala Gln
    1295                1300                1305
```

```
Ala Asn Thr Leu Met Gly Gln Gly Gly Asp Asp Thr Val Arg Gly
    1310            1315            1320

Gly Asp Gly Asp Asp Leu Leu Phe Gly Gly Asp Gly Asn Asp Met
    1325            1330            1335

Leu Tyr Gly Asp Ala Gly Asn Asp Thr Leu Tyr Gly Gly Leu Gly
    1340            1345            1350

Asp Asp Thr Leu Glu Gly Gly Ala Gly Asn Asp Trp Phe Gly Gln
    1355            1360            1365

Thr Pro Ala Arg Glu His Asp Val Leu Arg Gly Gly Ala Gly Val
    1370            1375            1380

Asp Thr Val Asp Tyr Ser Gln Ala Gly Ala His Ala Gly Val Ala
    1385            1390            1395

Thr Gly Arg Ile Gly Leu Gly Ile Leu Ala Asp Leu Gly Ala Gly
    1400            1405            1410

Arg Val Asp Lys Leu Gly Glu Ala Gly Ser Ser Ala Tyr Asp Thr
    1415            1420            1425

Val Ser Gly Ile Glu Asn Val Val Gly Thr Glu Leu Ala Asp Arg
    1430            1435            1440

Ile Thr Gly Asp Ala Gln Ala Asn Val Leu Arg Gly Ala Gly Gly
    1445            1450            1455

Ala Asp Val Leu Ala Gly Gly Glu Gly Asp Asp Val Leu Leu Gly
    1460            1465            1470

Gly Glu Gly Asp Asp Gln Leu Ser Gly Asp Ala Gly Arg Asp Arg
    1475            1480            1485

Leu Tyr Gly Glu Ala Gly Asp Asp Trp Phe Phe Gln Asp Ala Ala
    1490            1495            1500

Asn Ala Gly Asn Leu Leu Asp Gly Gly Asp Gly Asn Asp Thr Val
    1505            1510            1515

Asp Phe Ser Gly Pro Gly Arg Gly Leu Asp Ala Gly Ala Lys Gly
    1520            1525            1530

Val Phe Leu Ser Leu Gly Lys Gly Phe Ala Ser Leu Met Asp Glu
    1535            1540            1545

Pro Glu Thr Ser Asn Val Leu Arg His Ile Glu Asn Ala Val Gly
    1550            1555            1560

Ser Val Arg Asp Asp Val Leu Ile Gly Asp Ala Gly Ala Asn Val
    1565            1570            1575

Leu Asn Gly Leu Ala Gly Asn Asp Val Leu Ser Gly Gly Ala Gly
    1580            1585            1590

Asp Asp Val Leu Leu Gly Asp Glu Gly Ser Asp Leu Leu Ser Gly
    1595            1600            1605

Asp Ala Gly Asn Asp Asp Leu Phe Gly Gly Gln Gly Asp Asp Thr
    1610            1615            1620

Tyr Leu Phe Gly Ala Gly Tyr Gly His Asp Thr Ile Tyr Glu Ser
    1625            1630            1635

Gly Gly Gly His Asp Thr Ile Arg Ile Asn Ala Gly Ala Asp Gln
    1640            1645            1650

Leu Trp Phe Ala Arg Gln Gly Asn Asp Leu Glu Ile Arg Ile Leu
    1655            1660            1665

Gly Thr Asp Asp Ala Leu Thr Val His Asp Trp Tyr Arg Asp Ala
    1670            1675            1680

Asp His Arg Val Glu Ala Ile His Ala Ala Asn Gln Ala Ile Asp
    1685            1690            1695

Pro Ala Gly Ile Glu Lys Leu Val Glu Ala Met Ala Gln Tyr Pro
```

```
            1700                1705               1710
Asp Pro  Gly Ala Ala Ala   Ala Pro Pro Ala Ala  Arg Val Pro
         1715              1720              1725

Asp Thr  Leu Met Gln Ser  Leu Ala Val Asn Trp  Arg
         1730             1735              1740

<210> SEQ ID NO 11
<211> LENGTH: 1706
<212> TYPE: PRT
<213> ORGANISM: Bordetella hinzii

<400> SEQUENCE: 11

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Val Gln His Gly Thr Glu Gln Asn Asn
    290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
```

```
                        340                 345                 350
Ala Gly Lys Ser Leu Phe Asp Asp Gly Leu Gly Ala Ala Pro Gly Val
                355                 360                 365

Pro Ser Gly Arg Ser Lys Phe Ser Pro Asp Val Leu Glu Thr Val Pro
            370                 375                 380

Ala Ser Pro Gly Leu Arg Arg Pro Ser Leu Gly Ala Val Glu Arg Gln
385                 390                 395                 400

Asp Ser Gly Tyr Asp Ser Leu Asp Gly Val Gly Ser Arg Ser Phe Ser
                405                 410                 415

Leu Gly Glu Val Ser Asp Met Ala Ala Val Glu Ala Ala Glu Leu Glu
            420                 425                 430

Met Thr Arg Gln Val Leu His Ala Gly Ala Arg Gln Asp Asp Ala Glu
                435                 440                 445

Pro Gly Val Ser Gly Ala Ser Ala His Trp Gly Gln Arg Ala Leu Gln
            450                 455                 460

Gly Ala Gln Ala Val Ala Ala Ala Gln Arg Leu Val His Ala Ile Ala
465                 470                 475                 480

Leu Met Thr Gln Phe Gly Arg Ala Gly Ser Thr Asn Thr Pro Gln Glu
                485                 490                 495

Ala Ala Ser Leu Ser Ala Ala Val Phe Gly Leu Gly Glu Ala Ser Ser
            500                 505                 510

Ala Val Ala Glu Thr Val Ser Gly Phe Arg Gly Ser Ser Arg Trp
            515                 520                 525

Ala Gly Gly Phe Gly Val Ala Gly Gly Ala Met Ala Leu Gly Gly Gly
            530                 535                 540

Ile Ala Ala Ala Val Gly Ala Gly Met Ser Leu Thr Asp Asp Ala Pro
545                 550                 555                 560

Ala Gly Gln Lys Ala Ala Gly Ala Glu Ile Ala Leu Gln Leu Thr
                565                 570                 575

Gly Gly Thr Val Glu Leu Ala Ser Ser Ile Ala Leu Ala Leu Ala Ala
            580                 585                 590

Ala Arg Gly Val Thr Ser Gly Leu Gln Val Ala Gly Ala Ser Ala Gly
                595                 600                 605

Ala Ala Ala Gly Ala Leu Ala Ala Leu Ser Pro Met Glu Ile Tyr
            610                 615                 620

Gly Leu Val Gln Gln Ser His Tyr Ala Asp Gln Leu Asp Lys Leu Ala
625                 630                 635                 640

Gln Glu Ser Ser Ala Tyr Gly Tyr Glu Gly Asp Ala Leu Leu Ala Gln
                645                 650                 655

Leu Tyr Arg Asp Lys Thr Ala Ala Glu Gly Ala Val Ala Gly Val Ser
            660                 665                 670

Ala Val Leu Ser Thr Val Gly Ala Ala Val Ser Ile Ala Ala Ala Ala
            675                 680                 685

Ser Val Val Gly Ala Pro Val Ala Val Val Thr Ser Leu Leu Thr Gly
            690                 695                 700

Ala Leu Asn Gly Ile Leu Arg Gly Val Gln Gln Pro Ile Ile Glu Lys
705                 710                 715                 720

Leu Ala Asn Asp Tyr Ala Arg Lys Ile Asp Glu Leu Gly Gly Pro Gln
                725                 730                 735

Ala Tyr Phe Glu Lys Asn Leu Gln Ala Arg His Glu Gln Leu Ala Asn
            740                 745                 750

Ser Asp Gly Leu Arg Lys Met Leu Ala Asp Leu Gln Ala Gly Trp Asn
            755                 760                 765
```

-continued

```
Ala Ser Ser Val Ile Gly Val Gln Thr Thr Glu Ile Ser Lys Ser Ala
770                 775                 780
Leu Glu Leu Ala Ala Ile Thr Gly Asn Ala Asp Asn Leu Lys Ser Val
785                 790                 795                 800
Asp Val Phe Val Asp Arg Phe Val Gln Gly Glu Arg Val Ala Gly Gln
                805                 810                 815
Pro Val Val Leu Asp Val Ala Ala Gly Gly Ile Asp Ile Ala Ser Arg
                820                 825                 830
Lys Gly Glu Arg Pro Ala Leu Thr Phe Ile Thr Pro Leu Ala Ala Pro
                835                 840                 845
Gly Glu Glu Gln Arg Arg Thr Lys Thr Gly Lys Ser Glu Phe Thr
        850                 855                 860
Thr Phe Val Glu Ile Val Gly Lys Gln Asp Arg Trp Arg Ile Arg Asp
865                 870                 875                 880
Gly Ala Ala Asp Thr Thr Ile Asp Leu Ala Lys Val Val Ser Gln Leu
                885                 890                 895
Val Asp Ala Asn Gly Val Leu Lys His Ser Ile Lys Leu Asp Val Ile
                900                 905                 910
Gly Gly Asp Gly Asp Val Val Leu Ala Asn Ala Ser Arg Ile His
        915                 920                 925
Tyr Asp Gly Gly Ala Gly Thr Asn Thr Val Ser Tyr Ala Ala Leu Gly
    930                 935                 940
Arg Gln Asp Ser Ile Thr Val Ser Ala Asp Gly Glu Arg Phe Asn Val
945                 950                 955                 960
Arg Lys Gln Leu Asn Asn Ala Asn Val Tyr Arg Glu Gly Val Ala Thr
                965                 970                 975
Gln Thr Thr Ala Tyr Gly Lys Arg Thr Glu Asn Val Gln Tyr Arg His
                980                 985                 990
Val Glu Leu Ala Arg Val Gly Gln Leu Val Glu Val Asp Thr Leu Glu
            995                 1000                1005
His Val Gln His Ile Ile Gly Gly Ala Gly Asn Asp Ser Ile Thr
    1010                1015                1020
Gly Asn Ala His Asp Asn Phe Leu Ala Gly Gly Ser Gly Asp Asp
    1025                1030                1035
Arg Leu Asp Gly Gly Ala Gly Asn Asp Thr Leu Val Gly Gly Glu
    1040                1045                1050
Gly Gln Asn Thr Val Ile Gly Gly Ala Gly Asp Asp Val Phe Leu
    1055                1060                1065
Gln Asp Leu Gly Val Trp Ser Asn Gln Leu Asp Gly Gly Ala Gly
    1070                1075                1080
Val Asp Thr Val Lys Tyr Asn Val His Gln Pro Ser Glu Glu Arg
    1085                1090                1095
Leu Glu Arg Met Gly Asp Thr Gly Ile His Ala Asp Leu Gln Lys
    1100                1105                1110
Gly Thr Val Glu Lys Trp Pro Ala Leu Asn Leu Phe Ser Val Asp
    1115                1120                1125
His Val Lys Asn Ile Glu Asn Leu His Gly Ser Arg Leu Asn Asp
    1130                1135                1140
Arg Ile Ala Gly Asp Asp Gln Asp Asn Glu Leu Trp Gly His Asp
    1145                1150                1155
Gly Asn Asp Thr Ile Arg Gly Arg Gly Gly Asp Asp Ile Leu Arg
    1160                1165                1170
Gly Gly Leu Gly Leu Asp Thr Leu Tyr Gly Glu Asp Gly Asn Asp
    1175                1180                1185
```

```
Ile Phe Leu Gln Asp Asp Glu Thr Val Ser Asp Ile Asp Gly
    1190                1195                1200

Gly Ala Gly Leu Asp Thr Val Asp Tyr Ser Ala Met Ile His Pro
    1205                1210                1215

Gly Arg Ile Val Ala Pro His Glu Tyr Gly Phe Gly Ile Glu Ala
    1220                1225                1230

Asp Leu Ser Arg Glu Trp Val Arg Lys Ala Ser Ala Leu Gly Val
    1235                1240                1245

Asp Tyr Tyr Asp Asn Val Arg Asn Val Glu Asn Val Ile Gly Thr
    1250                1255                1260

Ser Met Lys Asp Val Leu Ile Gly Asp Ala Gln Ala Asn Thr Leu
    1265                1270                1275

Met Gly Gln Gly Gly Asp Thr Val Arg Gly Gly Asp Gly Asp
    1280                1285                1290

Asp Leu Leu Phe Gly Gly Asp Gly Asn Asp Met Leu Tyr Gly Asp
    1295                1300                1305

Ala Gly Asn Asp Thr Leu Tyr Gly Gly Leu Gly Asp Asp Thr Leu
    1310                1315                1320

Glu Gly Gly Ala Gly Asn Asp Trp Phe Gly Gln Thr Gln Ala Arg
    1325                1330                1335

Glu His Asp Val Leu Arg Gly Gly Asp Gly Val Asp Thr Val Asp
    1340                1345                1350

Tyr Ser Gln Thr Gly Ala His Ala Gly Ile Ala Ala Gly Arg Ile
    1355                1360                1365

Gly Leu Gly Ile Leu Ala Asp Leu Gly Ala Gly Arg Val Asp Lys
    1370                1375                1380

Leu Gly Glu Ala Gly Ser Ser Ala Tyr Asp Thr Val Ser Gly Ile
    1385                1390                1395

Glu Asn Val Val Gly Thr Glu Leu Ala Asp Arg Ile Thr Gly Asp
    1400                1405                1410

Ala Gln Ala Asn Val Leu Arg Gly Ala Gly Gly Ala Asp Val Leu
    1415                1420                1425

Ala Gly Gly Glu Gly Asp Asp Val Leu Leu Gly Gly Asp Gly Asp
    1430                1435                1440

Asp Gln Leu Ser Gly Asp Ala Gly Arg Asp Arg Leu Tyr Gly Glu
    1445                1450                1455

Ala Gly Asp Asp Trp Phe Phe Gln Asp Ala Ala Asn Ala Gly Asn
    1460                1465                1470

Leu Leu Asp Gly Gly Asp Gly Arg Asp Thr Val Asp Phe Ser Gly
    1475                1480                1485

Pro Gly Arg Gly Leu Asp Ala Gly Ala Lys Gly Val Phe Leu Ser
    1490                1495                1500

Leu Gly Lys Gly Phe Ala Ser Leu Met Asp Glu Pro Glu Thr Ser
    1505                1510                1515

Asn Val Leu Arg Asn Ile Glu Asn Ala Val Gly Ser Ala Arg Asp
    1520                1525                1530

Asp Val Leu Ile Gly Asp Ala Gly Ala Asn Val Leu Asn Gly Leu
    1535                1540                1545

Ala Gly Asn Asp Val Leu Ser Gly Gly Ala Gly Asp Asp Val Leu
    1550                1555                1560

Leu Gly Asp Glu Gly Ser Asp Leu Leu Ser Gly Asp Ala Gly Asn
    1565                1570                1575

Asp Asp Leu Phe Gly Gly Gln Gly Asp Asp Thr Tyr Leu Phe Gly
```

```
    1580                1585                1590

Val Gly  Tyr Gly His Asp Thr  Ile Tyr Glu Ser Gly  Gly Gly His
    1595                1600                1605

Asp Thr  Ile Arg Ile Asn Ala  Gly Ala Asp Gln Leu  Trp Phe Ala
    1610                1615                1620

Arg Gln  Gly Asn Asp Leu Glu  Ile Arg Ile Leu Gly  Thr Asp Asp
    1625                1630                1635

Ala Leu  Thr Val His Asp Trp  Tyr Arg Asp Ala Asp  His Arg Val
    1640                1645                1650

Glu Ile  Ile His Ala Ala Asn  Gln Ala Val Asp Gln  Ala Gly Ile
    1655                1660                1665

Glu Lys  Leu Val Glu Ala Met  Ala Gln Tyr Pro Asp  Pro Gly Ala
    1670                1675                1680

Ala Ala  Ala Ala Pro Pro Ala  Ala Arg Val Pro Asp  Thr Leu Met
    1685                1690                1695

Gln Ser  Leu Ala Val Asn Trp  Arg
    1700                1705

<210> SEQ ID NO 12
<211> LENGTH: 1705
<212> TYPE: PRT
<213> ORGANISM: Bordetella bronchiseptica

<400> SEQUENCE: 12

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
```

```
                    245                 250                 255
        Ala Arg Arg Gln Phe Arg Tyr Asp Gly Asp Met Asn Ile Gly Val Ile
                        260                 265                 270

Thr Asp Phe Glu Leu Glu Val Arg Asn Ala Leu Asn Arg Arg Ala His
                    275                 280                 285

Ala Val Gly Arg Gln Asp Val Gln His Gly Thr Glu Gln Asn Asn
                290                 295                 300

Pro Phe Pro Glu Ala Asp Glu Lys Ile Phe Val Val Ser Ala Thr Gly
        305                 310                 315                 320

Glu Ser Gln Met Leu Thr Arg Gly Gln Leu Lys Glu Tyr Ile Gly Gln
                        325                 330                 335

Gln Arg Gly Glu Gly Tyr Val Phe Tyr Glu Asn Arg Ala Tyr Gly Val
                    340                 345                 350

Ala Gly Lys Ser Leu Phe Asp Asp Gly Leu Gly Ala Ala Pro Gly Val
                        355                 360                 365

Pro Gly Arg Arg Ser Lys Ser Ser Pro Asp Val Leu Glu Thr Val Pro
                370                 375                 380

Ala Ser Pro Gly Leu Arg Arg Pro Ser Leu Gly Ala Val Glu Arg Gln
        385                 390                 395                 400

Asp Ser Gly Tyr Asp Ser Leu Asp Gly Val Gly Ser Arg Ser Phe Ser
                        405                 410                 415

Leu Gly Glu Val Ser Asp Met Ala Ala Val Glu Ala Ala Glu Leu Glu
                    420                 425                 430

Met Thr Arg Gln Val Leu His Ala Gly Ala Arg Gln Asp Asp Ala Glu
                        435                 440                 445

Pro Gly Val Ser Gly Ala Ser Ala His Trp Gly Gln Arg Ala Leu Gln
                    450                 455                 460

Gly Ala Gln Ala Val Ala Ala Ala Gln Arg Leu Val His Ala Ile Ala
        465                 470                 475                 480

Leu Met Thr Gln Phe Gly Arg Ala Gly Ser Thr Asn Thr Pro Gln Glu
                        485                 490                 495

Ala Ala Ser Leu Ser Ala Ala Val Phe Gly Leu Gly Glu Ala Ser Ser
                    500                 505                 510

Ala Val Ala Glu Thr Val Ser Gly Phe Phe Arg Gly Ser Ser Arg Trp
                    515                 520                 525

Ala Gly Gly Phe Gly Val Ala Gly Gly Ala Met Ala Leu Gly Gly Gly
                    530                 535                 540

Ile Gly Ala Val Gly Ala Gly Met Ser Leu Thr Asp Asp Ala Pro Ala
        545                 550                 555                 560

Gly Gln Lys Ala Ala Ala Gly Ala Glu Ile Ala Leu Gln Leu Thr Gly
                        565                 570                 575

Gly Thr Val Glu Leu Ala Ser Ser Ile Ala Leu Ala Leu Ala Ala Ala
                    580                 585                 590

Arg Gly Val Thr Ser Gly Leu Gln Val Ala Gly Ala Ser Ala Gly Ala
                        595                 600                 605

Ala Ala Gly Ala Leu Ala Ala Leu Ser Pro Met Glu Ile Tyr Gly
                    610                 615                 620

Leu Val Gln Gln Ser His Tyr Ala Asp Gln Leu Asp Lys Leu Ala Gln
        625                 630                 635                 640

Glu Ser Ser Ala Tyr Gly Tyr Glu Gly Asp Ala Leu Leu Ala Gln Leu
                        645                 650                 655

Tyr Arg Asp Lys Thr Ala Ala Glu Gly Ala Val Ala Gly Val Ser Ala
                    660                 665                 670
```

-continued

Val Leu Ser Thr Val Gly Ala Ala Val Ser Ile Ala Ala Ala Ala Ser
        675                 680                 685

Val Val Gly Ala Pro Val Ala Val Val Thr Ser Leu Leu Thr Gly Ala
    690                 695                 700

Leu Asn Gly Ile Leu Arg Gly Val Gln Gln Pro Ile Ile Glu Lys Leu
705                 710                 715                 720

Ala Asn Asp Tyr Ala Arg Lys Ile Asp Glu Leu Gly Gly Pro Gln Ala
                725                 730                 735

Tyr Phe Glu Lys Asn Leu Gln Ala Arg His Glu Gln Leu Ala Asn Ser
            740                 745                 750

Asp Gly Leu Arg Lys Met Leu Ala Asp Leu Gln Ala Gly Trp Asn Ala
        755                 760                 765

Ser Ser Val Ile Gly Val Gln Thr Thr Glu Ile Ser Lys Ser Ala Leu
    770                 775                 780

Glu Leu Ala Ala Ile Thr Gly Asn Ala Asp Asn Leu Lys Ser Ala Asp
785                 790                 795                 800

Val Phe Val Asp Arg Phe Ile Gln Gly Glu Arg Val Ala Gly Gln Pro
                805                 810                 815

Val Val Leu Asp Val Ala Gly Gly Ile Asp Ile Ala Ser Arg Lys
            820                 825                 830

Gly Glu Arg Pro Ala Leu Thr Phe Ile Thr Pro Leu Ala Ala Pro Gly
        835                 840                 845

Glu Glu Gln Arg Arg Thr Lys Thr Gly Lys Ser Glu Phe Thr Thr
    850                 855                 860

Phe Val Glu Ile Val Gly Lys Gln Asp Arg Trp Arg Ile Arg Asp Gly
865                 870                 875                 880

Ala Ala Asp Thr Thr Ile Asp Leu Ala Lys Val Val Ser Gln Leu Val
                885                 890                 895

Asp Ala Asn Gly Val Leu Lys His Ser Ile Lys Leu Glu Val Ile Gly
            900                 905                 910

Gly Asp Gly Asp Asp Val Val Leu Ala Asn Ala Ser Arg Ile His Tyr
        915                 920                 925

Asp Gly Gly Ala Gly Thr Asn Thr Val Ser Tyr Ala Ala Leu Gly Arg
    930                 935                 940

Gln Asp Ser Ile Thr Val Ser Ala Asp Gly Glu Arg Phe Asn Val Arg
945                 950                 955                 960

Lys Gln Leu Asn Asn Ala Asn Val Tyr Arg Glu Gly Val Ala Thr Gln
                965                 970                 975

Lys Thr Ala Tyr Gly Lys Arg Thr Glu Asn Val Gln Tyr Arg His Val
            980                 985                 990

Glu Leu Ala Arg Val Gly Gln Leu Val Glu Val Asp Thr Leu Glu His
        995                 1000                1005

Val Gln His Ile Ile Gly Gly Ala Gly Asn Asp Ser Ile Thr Gly
    1010                1015                1020

Asn Ala His Asp Asn Phe Leu Ala Gly Gly Ala Gly Asp Asp Arg
    1025                1030                1035

Leu Asp Gly Gly Ala Gly Asn Asp Thr Leu Val Gly Gly Glu Gly
    1040                1045                1050

His Asn Thr Val Val Gly Gly Ala Gly Asp Asp Val Phe Leu Gln
    1055                1060                1065

Asp Leu Gly Val Trp Ser Asn Gln Leu Asp Gly Gly Ala Gly Val
    1070                1075                1080

Asp Thr Val Lys Tyr Asn Val His Gln Pro Ser Glu Glu Arg Leu
    1085                1090                1095

-continued

```
Glu Arg Met Gly Asp Thr Gly Ile His Ala Asp Leu Gln Lys Gly
    1100            1105                1110
Thr Val Glu Lys Trp Pro Ala Leu Asn Leu Phe Ser Val Asp His
    1115            1120                1125
Val Lys Asn Ile Glu Asn Leu His Gly Ser Ser Leu Asn Asp Ser
    1130            1135                1140
Ile Ala Gly Asp Asp Arg Asp Asn Glu Leu Trp Gly Asp Asp Gly
    1145            1150                1155
Asn Asp Thr Ile His Gly Arg Gly Gly Asp Asp Ile Leu Arg Gly
    1160            1165                1170
Gly Leu Gly Leu Asp Thr Leu Tyr Gly Glu Asp Gly Asn Asp Ile
    1175            1180                1185
Phe Leu Gln Asp Asp Glu Thr Val Ser Asp Ile Asp Gly Gly
    1190            1195                1200
Ala Gly Leu Asp Thr Val Asp Tyr Ser Ala Met Ile His Ala Gly
    1205            1210                1215
Lys Ile Val Ala Pro His Glu Tyr Gly Phe Gly Ile Glu Ala Asp
    1220            1225                1230
Leu Ser Glu Gly Trp Val Arg Lys Ala Ala Arg Arg Gly Met Asp
    1235            1240                1245
Tyr Tyr Asp Ser Val Arg Ser Val Glu Asn Val Ile Gly Thr Ser
    1250            1255                1260
Met Lys Asp Val Leu Ile Gly Asp Ala Gln Ala Asn Thr Leu Met
    1265            1270                1275
Gly Gln Gly Gly Asp Asp Thr Val Arg Gly Gly Asp Gly Asp Asp
    1280            1285                1290
Leu Leu Phe Gly Gly Asp Gly Asn Asp Met Leu Tyr Gly Asp Ala
    1295            1300                1305
Gly Asn Asp Thr Leu Tyr Gly Gly Leu Gly Asp Asp Thr Leu Glu
    1310            1315                1320
Gly Gly Ala Gly Asn Asp Trp Phe Gly Gln Thr Pro Ala Arg Glu
    1325            1330                1335
His Asp Val Leu Arg Gly Gly Ala Gly Val Asp Thr Val Asp Tyr
    1340            1345                1350
Ser Gln Ala Gly Ala His Ala Gly Val Ala Thr Gly Arg Ile Gly
    1355            1360                1365
Leu Gly Ile Leu Ala Asp Leu Gly Ala Gly Arg Val Asp Lys Leu
    1370            1375                1380
Gly Glu Ala Gly Ser Ser Ala Tyr Asp Thr Val Ser Gly Ile Glu
    1385            1390                1395
Asn Val Val Gly Thr Glu Leu Ala Asp Arg Ile Thr Gly Asp Ala
    1400            1405                1410
Gln Ala Asn Val Leu Arg Gly Ala Gly Gly Ala Asp Val Leu Ala
    1415            1420                1425
Gly Gly Glu Gly Asp Asp Val Leu Leu Gly Gly Asp Gly Asp Asp
    1430            1435                1440
Gln Leu Ser Gly Asp Ala Gly Arg Asp Arg Leu Tyr Gly Glu Ala
    1445            1450                1455
Gly Asp Asp Trp Phe Phe Gln Asp Ala Ala Asn Ala Gly Asn Leu
    1460            1465                1470
Leu Asp Gly Gly Asp Gly Asn Asp Thr Val Asp Phe Ser Gly Pro
    1475            1480                1485
Gly Arg Gly Leu Asp Ala Gly Ala Lys Gly Val Phe Leu Ser Leu
```

-continued

| | | | | | | | | | |
|---|---|---|---|---|---|---|---|---|---|
| | | | | 1490 | | | 1495 | | 1500 |
| Gly | Lys | Gly | Phe | Ala | Ser | Leu | Met | Asp | Glu | Pro | Glu | Thr | Ser | Asn |
| | 1505 | | | | | 1510 | | | | | 1515 | | | |
| Val | Leu | Arg | His | Ile | Glu | Asn | Ala | Val | Gly | Ser | Val | Arg | Asp | Asp |
| | 1520 | | | | | 1525 | | | | | 1530 | | | |
| Val | Leu | Ile | Gly | Asp | Ala | Gly | Ala | Asn | Val | Leu | Asn | Gly | Leu | Ala |
| | 1535 | | | | | 1540 | | | | | 1545 | | | |
| Gly | Asn | Asp | Val | Leu | Ser | Ala | Ala | Pro | Ala | Asp | Asp | Val | Leu | Leu |
| | 1550 | | | | | 1555 | | | | | 1560 | | | |
| Gly | Asp | Glu | Gly | Ser | Asp | Leu | Leu | Ser | Gly | Asp | Ala | Gly | Asn | Asp |
| | 1565 | | | | | 1570 | | | | | 1575 | | | |
| Asp | Leu | Phe | Gly | Gly | Gln | Gly | Asp | Asp | Thr | Tyr | Leu | Phe | Gly | Ala |
| | 1580 | | | | | 1585 | | | | | 1590 | | | |
| Gly | Tyr | Gly | His | Asp | Thr | Ile | Tyr | Glu | Ser | Gly | Gly | Gly | His | Asp |
| | 1595 | | | | | 1600 | | | | | 1605 | | | |
| Thr | Ile | Arg | Ile | Asn | Ala | Gly | Ala | Asp | Gln | Leu | Trp | Phe | Ala | Arg |
| | 1610 | | | | | 1615 | | | | | 1620 | | | |
| Gln | Gly | Asn | Asp | Leu | Glu | Ile | Arg | Ile | Leu | Gly | Thr | Asp | Asp | Ala |
| | 1625 | | | | | 1630 | | | | | 1635 | | | |
| Leu | Thr | Val | His | Asp | Trp | Tyr | Arg | Asp | Ala | Asp | His | Arg | Val | Glu |
| | 1640 | | | | | 1645 | | | | | 1650 | | | |
| Ala | Ile | His | Ala | Ala | Asn | Gln | Ala | Ile | Asp | Pro | Ala | Gly | Ile | Glu |
| | 1655 | | | | | 1660 | | | | | 1665 | | | |
| Lys | Leu | Val | Glu | Ala | Met | Ala | Gln | Tyr | Pro | Asp | Pro | Gly | Ala | Ala |
| | 1670 | | | | | 1675 | | | | | 1680 | | | |
| Ala | Ala | Ala | Pro | Pro | Ala | Ala | Arg | Val | Pro | Asp | Thr | Leu | Met | Gln |
| | 1685 | | | | | 1690 | | | | | 1695 | | | |
| Ser | Leu | Ala | Val | Asn | Trp | Arg | | | | | | | | |
| | 1700 | | | | | 1705 | | | | | | | | |

MUTANT CYAA POLYPEPTIDES AND POLYPEPTIDE DERIVATIVES SUITABLE FOR THE DELIVERY OF IMMUNOGENIC MOLECULES INTO A CELL

The invention relates to polypeptides suitable for use in the delivery of one or more molecules into a cell.

In particular, the invention relates to polypeptides suitable for use in the delivery of one or more molecules which are able to elicit an immune response into a host, especially by targeting cells which express the CD11b/CD18 receptor (also referred to herein as "CD11b expressing cells").

The invention is more particularly directed to polypeptides derived from an adenylate cyclase protein (CyaA), the latter being used either under the form of a toxin or of a detoxified protein or toxoid, which are mutant polypeptides. Said mutant polypeptides are capable of retaining the binding activity of native CyaA to a target cell and preferably of also retaining the translocating activity of native CyaA through its N-terminal domain into target cells and furthermore have a pore-forming activity which is reduced or suppressed as compared to that of the native CyaA toxin.

The invention relates in particular to the use of said polypeptides as proteinaceous vectors. Accordingly the mutant polypeptides are further combined with non-CyaA molecules, thereby giving rise to polypeptide derivatives, wherein said molecules have a preventive vaccinal and/or therapeutic interest when administered to a host.

The polypeptides according to the invention are suitable for use as proteinaceous vectors for the delivery of a molecule, in particular of a polypeptidic molecule having an amino acid sequence comprising one or more epitope(s), especially antigens, into a cell, in particular in CD11b expressing cells.

The invention thus also relates to a polypeptide derivative (a derivative of the mutant polypeptide of the invention) which comprises or consists of a mutant polypeptide according to the invention recombined to one or more molecules, in particular to one or more molecules suitable for eliciting an immune response, thus constituting a recombinant polypeptide or a fusion polypeptide. The invention also relates to polypeptide derivatives obtained by chemically grafting said molecule(s) to the mutant polypeptides.

According to an embodiment, the polypeptide derivatives according to the invention are suitable for use in prophylactic treatment and especially in vaccination and in therapy including in immunotherapy, in particular for eliciting an immune response in a subject.

The native CyaA used in the context of the present invention for the design of the polypeptides of the invention is the adenylate cyclase produced primarily in *Bordetella* organisms, especially in *Bordetella Pertussis* and which has the following features and properties disclosed for the purpose of characterising said protein in the context of the invention.

The bifunctional RTX adenylate cyclase toxin-hemolysin (also designated herewith as the adenylate cysclase toxin (CyaA, ACT, or AC-Hly) is a key virulence factor of *Bordetella pertussis* which is the causative agent of whooping cough (1). Its 1706 residues-long polypeptide is a fusion of an N-terminal adenylate cyclase (AC) enzyme domain or part (~400 residues) to a pore-forming RTX hemolysin (Repeat in ToXin cytolysin) of ~1306 residues constituting the C-terminal part or domain (2). The latter harbors the sites of activation of proCyaA to CyaA by covalent post-translational palmitoylation of ε-amino groups of $Lys^{860}$ and $Lys^{983}$, as well as the numerous RTX repeats forming ~40 calcium binding sites, the loading of which is required for cytotoxic activity of CyaA (3, 4). The CyaA protein is indeed synthesized as an inactive protoxin which is converted into an active toxin by post translational palmitoyation of two internal lysine residues (lysines 860 and 983). This post translational modification requires the expression with the cyaA gene, of an accessory gene i.e., cyaC which is located nearby cyaA on *B. pertussis* chromosome.

The toxin primarily targets host myeloid phagocytes expressing the $\alpha_M\beta_2$ integrin receptor, known also as CD11b/CD18, CR3 or Mac-1 (5). Said toxin especially binds to the CD11b/CD18 receptor of cells expressing the same through a receptor binding site present in its C-terminal part. These cells are accordingly target cells for the native toxin and also for the polypeptides of the invention. CyaA inserts into cytoplasmic membrane of cells and translocates the AC enzyme domain into the cytosol of said target cells (6, 7). Inside cells, the AC is activated by calmodulin and catalyzes uncontrolled conversion of cellular ATP to cAMP, a key second messenger molecule provoking impairment of bactericidal functions of phagocytes (1). At high doses (>100 ng/ml), CyaA-catalyzed dissipation of ATP into cAMP becomes cytotoxic and promotes apoptosis or even rapid necrotic death and lysis of $CD11b^+$ monocytes (8, 9).

Recently, the inventors showed that CyaA binds N-linked oligosaccharides of its CD11b/CD18 receptor (10). This suggests that low specificity interactions with glycans of ubiquitous cell surface proteins or glycolipids may account for the about two order of magnitude reduced but readily detectable capacity of CyaA to penetrate also cells lacking CD11b/CD18. Indeed, due to the extremely high specific catalytic activity of the AC domain, CyaA was found to substantially elevate cAMP also in mammalian and avian erythrocytes, lymphocytes, lymphoma, neuroblastoma, CHO, or tracheal epithelial cells (1, 11).

It has already been proposed in the prior art to provide detoxified toxin also called toxoid, wherein the adenylate cyclase activity is decreased, especially essentially suppressed. Such CyaA/AC⁻ toxoid may be used to achieve the preparation of the polypeptides of the invention.

Besides elevating cAMP, the toxin exhibits also a moderate hemolytic activity on mammalian and avian erythrocytes. This is due to the capacity to form small cation-selective pores of an estimated diameter of 0.6 to 0.8 nm, which permeabilize cellular membrane and eventually provoke colloid-osmotic cell lysis (12). Recently, the inventors and others have shown that the pore-forming activity of CyaA synergizes with its cell-invasive AC enzyme activity and contributes to the overall cytolytic potency of CyaA on $CD11b^+$ cells (13, 14). Due to an intact pore-forming (hemolytic) capacity, in the absence of osmoprotectants such as serum, the enzymatically inactive CyaA/AC⁻ toxoid (15) still exhibits a full hemolytic activity on erythrocytes and a residual, about tenfold reduced cytolytic activity on CD11b-expressing monocytes (8), which sets a limit to its use in therapy.

The hemolytic (pore-forming) and AC membrane translocation (cell-invasive) activities of CyaA were early on found to be dissociable by low calcium concentration, low temperature (16) and by the extent and nature of acylation of CyaA (4, 12, 17). Moreover, the two activities differ substantially in sensitivity to charge-reversing or neutral substitutions of glutamates at positions 509, 516, 570 and 581 within the hydrophobic domain (8, 13, 18). The cell-invasive and pore-forming activities of CyaA were thus proposed to be mutually independent and operating in parallel in target cell membrane. The model illustrated in FIG. 5A, suggests that two distinct CyaA conformers insert into target cell membrane in parallel, one being the translocation precursor, accounting for delivery of the AC domain across cellular membrane with concomitant influx of calcium ions into cells, the other being a pore precursor eventually forming oligomeric pores (13, 18, 19).

The inventors have now tested this model and refined it, showing that the pore-forming activity is not involved in translocation of the AC domain across target cell.

In the present invention, the inventors initially designed CyaA mutant polypeptides, based especially on the adenylate cyclase of Bordetella pertussis, either in the toxin or in the toxoid format, having a combination of substitutions within the pore-forming (E570Q) and acylation-bearing (K860R) domains and showed that this specific combination of substitutions selectively abolished the cell-permeabilizing activity of CyaA, thus eliminating the residual cytolytic activity of CyaA/AC− toxoids on CD11b+ cells. At the same time, the E570Q+K860R construct retained a full capacity to translocate the AC domain into cytosol of cells to elevate cellular cAMP and its toxoid was fully capable to deliver epitopes containing molecules inserted within said construct to the cytosolic pathway of dendritic cells for MHC class I-restricted presentation and induction of specific cytotoxic T cell responses in vivo.

The CyaA/233OVA/E570Q+K860R mutant designed by the inventors, and in which an OVA antigenic peptide is inserted as described in the examples, is the first construct illustrative of the capacity of the CyaA mutant to provide an importantly reduced capacity to permeabilize cells that remains fully capable of translocating the AC domain across cellular membrane.

The inventors have now designed particular constructs, illustrated especially as a CyaA/E570Q+K860R/AC− toxoid and have shown that despite its much reduced cell-permeabilizing (cytolytic) activity, it remains fully active in antigen delivery into CD11b+ APCs. The inventors have further shown that the overall cytolytic activity of the illustrative CyaA/E570Q+K860R/AC− toxoid is very low. It is thus devoid of residual toxicity in an animal or human host and is therefore highly suitable for use in therapy.

The invention thus provides new polypeptides, which are toxoids and have an enhaced safety profile and can be used as proteinaceous vectors for the delivery of molecules of interest, in particular of immunogenic peptidic sequences, to cells of a patient in need of a treatment, and more particularly to cells expressing CD11b.

Based on the experiments carried out by the inventors it has thus been possible to define and provide a polypeptide which is a mutant of an adenylate cyclase protein (mutant polypeptide) and whose amino acid sequence comprises or consists of one of the following sequences:

a) the amino acid sequence of the adenylate cyclase (CyaA) of *Bordetella pertussis*, *Bordetella parapertussis* or *Bordetella hinzii* wherein the following mutations have been performed:
  (i) the substitution of the glutamic acid residue at position 570 by a glutamine residue (E570Q) or by a conservative amino acid residue, and
  (ii) the substitution of the lysine residue at position 860 by an arginine residue (K860R) or by a conservative amino acid residue, or;

b) an amino acid sequence of a fragment of the adenylate cyclase of *Bordetella pertussis*, *Bordetella parapertussis* or *Bordetella hinzii*, which fragment has the capacity of the CyaA protein of *Bordetella pertussis* to bind to a target cell and the capacity to translocate its N-terminal adenylate cyclase enzyme domain or part thereof into said cell, wherein said fragment further contains the following mutated amino acid residues located at positions 570 and 860 in said adenylate cyclase: E570Q and K860R, or c) an amino acid sequence which differs from the amino acid sequence as defined in a) or b) by one or more amino acid residue substitutions and/or insertions and which has the capacity of the CyaA protein of *Bordetella Pertussis* to bind to a target cell and the capacity to translocate its N-terminal adenylate cyclase enzyme domain or part thereof into said cell, wherein said amino acid sequence further contains the following mutated amino acid residues located at positions 570 and 860 in said adenylate cyclase: E570Q and K860R, or d) the amino acid sequence of the adenylate cyclase (CyaA) of *Bordetella bronchiseptica* wherein the following mutations have been performed:
  (i) the substitution of the glutamic acid residue at position 569 by a glutamine residue (E569Q) or by a conservative amino acid residue, and
  (ii) the substitution of the lysine residue at position 859 by an arginine residue (K859R) or by a conservative amino acid residue, or;

e) an amino acid sequence of a fragment of the adenylate cyclase of *Bordetella bronchiseptica*, which fragment has the capacity of the CyaA protein of *Bordetella pertussis* to bind to a target cell and the capacity to translocate its N-terminal adenylate cyclase enzyme domain or part thereof into said cell, wherein said fragment further contains the following mutated amino acid residues located at positions 569 and 859 in said adenylate cyclase: E569Q and K859R, or f) an amino acid sequence which differs from the amino acid sequence as defined in d) or e) by one or more amino acid residue substitutions and/or insertions and which has the capacity of the CyaA protein of *Bordetella Pertussis* to bind to a target cell and the capacity to translocate its N-terminal adenylate cyclase enzyme domain or part thereof into said cell, wherein said amino acid sequence further contains the following mutated amino acid residues located at positions 569 and 859 in said adenylate cyclase: E569Q and K859R.

For the purpose of the invention, the N-terminal domain of the described fragment is the amino acid sequence of the fragment which includes the contiguous amino acid residues of the N-terminal part of the native CyaA protein, e.g. the N-terminal part of the fragment is all or part of the contiguous residues forming the sequence of 400 amino acid residues of the N-terminal domain of the *Bordetella pertussis* CyaA protein.

Herein, "E570Q" encompasses substitution of the glutamic acid residue at position 570 of native CyaA of *Bordetella pertussis*, *Bordetella parapertussis* or *Bordetella hinzii* by a glutamine residue or by another conservative residue, in particular a residue whose side chain size and hydrophilic nature is close to that of glutamic acid. The glutamic acid residue at position 570 is preferably substituted by an amino acid residue selected from Gln, Asn, Met, Thr, Ser, Gly, Arg, Lys, Val, Leu, Cys, Ile, Asp.

Herein, "K860R" encompasses substitution of the lysine residue at position 860 of native CyaA of *Bordetella pertussis*, *Bordetella parapertussis* or *Bordetella hinzii* by an arginine residue or by another conservative residue, in particular a residue whose side chain size and hydrophilic nature is close to that of lysine. The lysine residue at position 860 is preferably substituted by an amino acid residue selected from Arg, Asn, Gln, Met, Thr, Ser, Gly, Val, Leu, Cys, Ile.

Herein, "E569Q" encompasses substitution of the glutamic acid residue at position 569 of native CyaA of *Bordetella bronchiseptica* by a glutamine residue or by another conservative residue, in particular a residue whose side chain size and hydrophilic nature is close to that of glutamic acid. The glutamic acid residue at position 569 is preferably substituted by an amino acid residue selected from Gln, Asn, Met, Thr, Ser, Gly, Arg, Lys, Val, Leu, Cys, Ile, Asp.

Herein, "K859R" encompasses substitution of the lysine residue at position 859 of native CyaA of *Bordetella bronchiseptica* by an arginine residue or by another conservative residue, in particular a residue whose side chain size and hydrophilic nature is close to that of lysine. The lysine residue at position 859 is preferably substituted by an amino acid residue selected from Arg, Asn, Gln, Met, Thr, Ser, Gly, Val, Leu, Cys, Ile.

In the embodiments described hereafter, the mutant *Bordetella pertussis* CyaA proteins or protein fragments carrying the "E570Q" and "K860R" substitutions may be replaced by mutant *Bordetella parapertussis* or *Bordetella hinzii* CyaA proteins or protein fragments carrying the equivalent "E570Q" and "K860R" substitutions, or by mutant *Bordetella bronchiseptica* CyaA proteins or protein fragment carrying the equivalent "E569Q" and "K859R" substitutions.

The native CyaA of *Bordetella pertussis* has also been described as an amino acid sequence and a nucleotide sequence by Glaser, P. et al, 1988, Molecular Microbiology 2(1), 19-30. This sequence is referred to as SEQ ID No1 as illustrated in FIG. 6. Accordingly, when amino acid residues or sequences or nucleotides or nucleotide sequences of the CyaA protein of *B. pertussis*, are cited in the present invention their positions are given with respect to the sequences disclosed in said publication of Glaser et al. 1988.

In an embodiment of the present invention the amino sequence of the *Bordetella pertussis* adenylate cyclase is the sequence disclosed as SEQ ID No1.

When reference is made to SEQ ID No1 or to SEQ ID No2 herein, it is especially pointed out that, unless it is technically not relevant, the disclosed features would similarly apply to a sequence modified by insertion of residues in SEQ ID No1 or SEQ ID No2 in order to detoxify the CyaA protein. In such a case, the numbering of the amino acid residues should be adapted (especially insofar as positions 570 and 860 of the native sequence are concerned).

Advantageously, the CyaA protein or a fragment thereof is a protein or a fragment thereof, which is the result of the co-expression in a cell, especially in a recombinant cell, of both cyaA and cyaC genes. It has been indeed shown that in order to have invasive properties for target cells, CyaA has to undergo post-translational modifications which are enabled by the expression of both cyaA and cyaC genes (WO 93/21324).

In a particular embodiment of the invention, the CyaA protein is a bacterial protein. In a preferred embodiment, CyaA protein is derived from a *Bordetella* species.

Among *Bordetella* species of interest, according to the invention, one of them is *Bordetella pertussis*. Other *Bordetella* strains of interest are those of Bordetella parapertussis, *Bordetella hinzii* or *Bordetella bronchiseptica*. The sequences of CyaA protein of *B. parapertussis* has been disclosed especially under accession number NC 002928.3 (as a sequence of 1740 amino acids) (SEQ ID NO: 8) and in Parkhill J. et al (Nat. Genet. DOI, 10 (2003)), for *B. hinzii* in Donato G. M. et al (J. Bacteriol. 2005 November, 187(22): 7579-88) (SEQ ID NO: 9) and for *B. bronchiseptica* in Betsou F. et al (Gene 1995, Aug. 30; 162(1): 165-6) (SEQ ID NO: 10).

The expression "polypeptide mutant of the adenylate cyclase protein" excludes the native adenylate cyclase as expressed by *Bordetella*. As stated above, it is characterised by a primary difference with the native protein, lying in the combined substitution of two specific amino acid residues. It may be further modified with respect to said native protein and it may especially be a fragment of the thus mutated protein, such as for example a truncated variant of said mutated protein, wherein residues at either or both terminal ends are deleted. In particular residues at the C-terminal end may be deleted to the extent that it does not affect the recognition and binding site for the CD11b/CD18 cell receptor. Alternatively or in addition residues may be deleted at the N-terminal end to the effect that it does not affect the translocation ability of the obtained mutant polypeptide. It may also be a fragment obtained after internal deletions of one or more residues of the native mutated CyaA protein.

Where the invention relates to a polypeptide mutant which is a fragment as stated herein, said fragment which necessarily comprises the mutated residues E570Q and K860R (when reference is made to the amino sequence of the CyaA protein of *Bordetella pertussis*) also retains the ability of the mutated full-length CyaA to bind cells and to translocate its N-terminal domain into the cytosol of target cells, especially of CD11b/CD18 expressing cells.

The invention provides thus mutant polypeptides suitable for use in the design of means for the delivery of one or more molecules into a cell, especially a target cell expressing the CD11b/CD18 receptor.

In particular the invention provides mutant polypeptides of a CyaA protein, where said protein is either derived from the CyaA toxin or is preferably derived from a toxoid thereof, especially a CyaA/AC⁻ toxoid. The mutant polypeptides are capable of binding to a cell, especially to a target cell, especially a target cell expressing the CD11b/CD18 receptor, are capable of translocating their N-terminal domain or the molecule inserted in said domain or grafted on it into the cell and their pore-forming activity is totally or partially suppressed as compared to that of the CyaA toxin or toxoid.

The capacity of the mutant polypeptide to target CD11b/CD18 cells can be assayed especially according to the methods disclosed in EP 03291486.3 and El-Azami-El-Idrissi M. et al, J. Biol. Chem., 278(40)38514-21 or in WO 02/22169. Furthermore, the capacity of the mutant polypeptide to translocate the epitope(s) or polypeptide(s) containing said epitope(s) into the cytosol of target cell can be assayed by applying the method described in WO 02/22169.

Total or partial suppression of the CyaA toxin or toxoid pore-forming activity, or cell-permeabilizing capacity, is to be understood as the total or partial suppression of the ability to form pores, in particular cation selective pores of an estimated diameter of 0.6 to 0.8 nm, which permeabilize a cellular membrane and eventually provoke colloid-osmotic cell lysis. The pore-forming activity can be measured using the single whole cell patch-clamp experiment as described in examples.

The pore-forming activity of the CyaA toxin contributes to its overall cytolytic or haemolytic activity on cells. Indeed in the context of the present invention, the overall cytolytic or haemolytic activity of CyaA (or its "overall cytotoxic activity") is to be understood as the resultant of at least the adenylate cyclase and pore-forming activities of the CyaA toxin. Thus total or partial suppression of the CyaA toxin pore-forming activity allows at least a partial suppression of its cytolytic activity.

In a preferred embodiment, the overall cytolytic activity of the polypeptide according to the invention, in particular on cells which express the CD11b/CD18 receptor, is totally or partially reduced as compared to that of the *Bordetella pertussis* CyaA toxin. The cytolytic activity of the inventive polypeptide can be determined by measuring the amount of hemoglobulin (for erythrocytes) or of lactate dehydrogenase (for monocytes) released by the cells when incubated with the tested polypeptide as described in examples.

In a preferred embodiment, the overall cytolytic activity of the polypeptide according to the invention on cells which express the CD11b/CD18 receptor is at least 75% lower, preferably still at least 80%, 85%, 90% or 95% lower, than that the *Bordetella pertussis* CyaA toxin, or than that of a *Bordetella pertussis* CyaA protein whose adenylate cyclase activity is partly or totally suppressed (or "CyaA toxoid"). In a particularly preferred embodiment, the overall cytolytic activity of the polypeptide according to the invention on cells which express the CD11b/CD18 receptor is at least 75% lower, preferably still at least 80% or 85% lower, than that the *Bordetella pertussis* CyaA toxoid whose amino acid sequence is shown in FIG. 2 (SEQ ID No2).

In a preferred embodiment, the invention relates to a polypeptide which is a mutant of an adenylate cyclase and whose amino acid sequence comprises or consists of an amino acid sequence (i) which is mutated with respect to the amino acid sequence disclosed in SEQ ID No1 said mutations comprising at least the substitutions E570Q and K860R or (ii) which is a fragment of the CyaA protein having said amino acid sequence disclosed as SEQ ID No1, to the extent that said fragment has an amino acid sequence including substitutions E570Q and K860R and wherein the polypeptide is capable of binding to a target cell and of translocating its N-terminal domain into the cell.

In a particular embodiment of the present invention, the fragment including a substitution of the glutamic acid residue at position 570 of SEQ ID No1 by a glutamine residue (referred to as "E570Q"), and the substitution of the lysine residue at position 860 of SEQ ID No1 by an arginine residue (referred to as "K860R") encompasses at least the amino acid sequence of the CyaA protein starting with the first N-terminal residue or from one of the amino acid residues comprised between the positions 1 and 400, preferably between the positions 1 and 380 and extending up to the residues forming the recognition and binding site for the CD11b/CD18 cell receptor and said fragment contains residues corresponding to the mutated E570Q and K860R residues or consists of said amino acid sequence. In a preferred embodiment, the fragment including the E570Q and K860R substitutions does not comprise the amino acid sequence running from the amino acid at position 1 of SEQ ID No1 to the amino acid at position 372 of SEQ ID No1.

In a preferred embodiment the fragment which is thus prepared has essentially lost the adenyl cyclase enzyme activity (AC activity)

In a preferred embodiment, the mutant polypeptide of the invention is produced by co-expression in a recombinant cell of a mutated gene encoding the E570Q and R860Q mutated CyaA amino acid sequence and of the cyaC gene, followed by recovery of the selected expressed fragment of mutant CyaA.

Preferably, the mutant polypeptide of the invention has a lysine residue which corresponds to the lysine residue at position 983 of the CyaA amino acid sequence as set forth in SEQ ID No1 and which is acylated, in particular which is palmytoylated or palmitoleilated.

Alternatively, the mutant polypeptide of the invention has a lysine residue which corresponds to the lysine residue at position 983 of the CyaA amino acid sequence as set forth in SEQ ID No1 which is not acylated.

In a specific embodiment, the mutant polypeptide of the invention has an amino acid sequence derived from the CyaA amino acid sequence disclosed in SEQ ID No1 by mutation of residues resulting in E570Q and K860R and has an amino acid sequence which shares at least 50%, preferably at least 60%, 70%, 75%, 80%, 85%, 90%, 95% or 99% identity with the sequence set forth in SEQ ID No1.

In another specific embodiment, the mutant polypeptide of the invention has an amino acid sequence which differs from the CyaA amino acid sequence as set forth in SEQ ID No1 by mutation of residues resulting in E570Q and K860R and by further mutations resulting in 1 to 500, in particular, 1 to 400, 1 to 300, 1 to 200, 1 to 100, 1 to 50, 1 to 40, 1 to 30, 1 to 25, 1 to 20, 1 to 15, 1 to 10 or 1 to 5 amino acid residue substitutions, deletions, and/or insertions including the E570Q and K860R substitutions.

In a specific embodiment, the mutant polypeptide of the invention does not carry any amino acid residue substitutions, deletions, and/or insertions as compared to the *Bordetella pertussis* CyaA amino acid sequence other than the E570Q and K860R substitutions. In a specific embodiment, the mutant polypeptide has amino acid sequence of SEQ ID No2 as illustrated in FIG. 7. In another specific embodiment, the only further amino acid substitutions, deletions, and/or insertions as compared to the amino acid sequence of SEQ ID No2 consist in amino acid substitutions, deletions, and/or insertions which totally or partially suppress the adenyl cyclase enzymatic activity of the CyaA protein, such as in particular the insertion of a dipeptide, for example an "LQ" or "GS" dipeptide between the amino acids at positions 188 and 189.

In a particular embodiment, the mutant polypeptide of the invention differs from the CyaA amino acid sequence as set forth in SEQ ID No1 by 1, 2, 3, 4, 5, 6, 7, 8, 9 or 10 amino acid residue substitutions, deletions, and/or insertions in addition to the E570Q and K860R substitutions.

In a particular embodiment, in addition to the E570Q and K860R substitutions, the leucine residue at position 247 of the native CyaA protein of *Bordetella pertussis* is substituted by a glutamine residue (L247Q) or by another amino acid residue in particular a conservative amino acid residue.

A mutant polypeptide of the invention which is a fragment as disclosed herein of the amino acid sequence disclosed in SEQ ID No1 is to be understood as a sequence which comprises one or more fragments having at least about 350 amino acid residues and up to about 1705 amino acid residues of the SEQ ID No1 amino acid sequence, in particular fragments comprising a stretch of at least 400, 500, 600, 700, 800, 900, 1000, 1100, 1200, 1300, 1400, 1500, 1600 amino acid residues of SEQ ID No1, encompassing residues E570Q and K860R. A mutant polypeptide of the invention can also be defined as a fragment of the amino acid sequence disclosed in SEQ ID No2 which comprises one or more fragments having at least about 350 amino acid residues and up to about 1705 amino acid residues of the SEQ ID No2 amino acid sequence, in particular fragments comprising a stretch of at least 400, 500, 600, 700, 800, 900, 1000, 1100, 1200, 1300, 1400, 1500, 1600 amino acid residues of SEQ ID No2, encompassing residues 570 and 860. Said fragments preferably retain the capacity of binding to the CD11b/CD18 cell receptor and the ability to translocate their N-terminal domain into target cells. Preferably, the mutant polypeptide of the invention which is such a fragment which has a stretch of amino acids comprising amino acid residues 570 as E570Q to 860 as K860R or 1 to 860, or 2 to 860 of SEQ ID No1 to the extent that the E570Q and K860R mutations are observed with respect to the original SEQ ID No1.

In a preferred embodiment, the fragment further comprises amino acid residues 1166 to 1281 or amino acid residues 1208 to 1243 of the CyaA amino acid sequence as set forth in SEQ ID No1 of CyaA protein for interaction with CD11b/CD18 target cells.

A particular fragment thus encompasses all or part of the C-terminal part of the native protein which part is responsible for the binding of the polypeptide of the invention to target cell membrane and/or CD11b/CD18 receptor, and for the subsequent delivery of the N-terminal domain of the polypeptide into the cell cytosol. A particular polypeptide of the invention is the fragment of CyaA protein which contains amino acid residues 373 to 1706 of CyaA protein especially of the SEQ ID No1, to the extent that residues 570 and 860 are mutated as E570Q and K860R.

In another preferred embodiment, the mutant polypeptide which is such a fragment comprises:

a) a first amino acid sequence which corresponds to a stretch of at least 100 contiguous amino acid residues from SEQ ID No1 comprising amino acid residues 570 as E570Q, and further including 0, 1, 2, 3, 4 or 5 deletions, substitutions or insertions as compared to SEQ ID No1 and b) a second amino acid sequence which corresponds to a stretch of at least 100 contiguous amino acid residues from SEQ ID No1 comprising amino acid residues 860 as K860R, and further including 0, 1, 2, 3, 4 or 5 deletions, substitutions or insertions as compared to SEQ ID No1 and preferably, c) a third amino acid sequence comprising amino acid residues 1166 to 1281 or amino acid residues 1208 to 1243 of the CyaA amino acid sequence as set forth in SEQ ID No1 of CyaA protein for interaction with CD11b/CD18 target cells.

Another particular polypeptide of the invention is a fragment which is one which corresponds to the E570Q and K860R mutated CyaA protein wherein amino acid residues 225 to 234 have been deleted, thus providing a fragment containing residues 1 to 224 and 235 to 1706 of the mutated protein.

In a particularly preferred embodiment, the polypeptide fragment according to the invention binds to a cell which expresses the CD11b/CD18 receptor as a result of specific binding to said receptor.

In a preferred embodiment, adenylate cyclase activity of the polypeptide in a cell is partly or totally suppressed as compared to that of the Bordetella pertussis CyaA toxin. As stated above, the expression "CyaA protein" relates either to the toxin form or preferably to the toxoid form of the protein. Accordingly each embodiment of the invention relating to the polypeptide which is a mutant of the CyaA protein applies to each of the toxin or toxoid form of the protein.

Total or partial suppression of CyaA adenylate cyclase or enzymatic activity is to be understood as the total or partial suppression of the ability to convert ATP into cAMP in a cellular environment as compared to that of a CyaA toxin produced by co-expression of the cyaA and cyaC genes in a cell. The ability to convert ATP into cAMP can be determined by measuring the level of intracellular cAMP as described in the examples.

Such total or partial suppression can be obtained as a result of genetic inactivation, for example by introduction of a short amino acid sequence sequence, comprising for example from one to ten amino acids, in particular a dipeptide in a site of the amino acid sequence of CyaA which is part of the catalytic site, i.e. in a site located within the first 400 amino acids (AC domain) of SEQ ID No1 or by deletion or substitution of a part of the CyaA amino acid sequence as set forth in SEQ ID No1 which is essential for enzymatic activity. In a preferred embodiment, total or partial suppression of the CyaA enzymatic activity is obtained by insertion of a dipeptide, for example an "LQ" or "GS" dipeptide, between the amino acids at position 188 and 189 of the CyaA sequence as set forth in SEQ ID No1. This can be achieved by inserting an oligonucleotide, such as "CTG CAG" or "CGATCC", at the EcoRV site at position 564 of the coding phase of the cyaA gene. See Ladant et al., 1992. Alternatively, total or partial suppression of the enzymatic activity can also be obtained by directed mutagenesis, for example, by replacing the lysine residue at position 58 or 65 of the native CyaA Bordetella pertussis protein (Glaser et al., 1989) by a Gin residue.

The invention is also directed to a polypeptide derivative comprising or consisting of the mutant polypeptide according to the invention which is further combined with one or more molecules of interest. In a preferred embodiment, a molecule of interest is a biologically active molecule either when taken alone or when combined to the polypeptide of the invention. Said molecules may especially be of prophylactic value or therapeutic value i.e., may have a prophylactic or a therapeutic activity, or may enhance a prophylactic or therapeutic activity.

In specific embodiments, the molecules of interest are selected in the group comprising: peptides, glycopeptides, lipopeptides, polysaccharides, oligosaccharides, nucleic acids, lipids and chemicals.

In a specific embodiment, the one or more molecules of interest are polypeptidic molecules or contain polypeptidic molecules. Their amino acid sequence may comprise 2 to 1000, preferably 5-800, 5 to 500, 5 to 200, 5 to 100, 8 to 50, 5 to 25, 5 to 20 or 8 to 16, or 300-600, 400-500, amino acid residues.

In a preferred embodiment, the one or more molecules of interest are heterologous amino acid sequences suitable for eliciting an immune response (also referred to as "heterologous antigens"), in particular amino acid sequences which comprise or consist of an epitope, including antigens. As used herein, the term "heterologous" refers to an antigen other than the mutant polypeptide which is used in the vector itself. As used herein, the term "epitope" refers to a heterologous molecule and especially a heterologous peptide that can elicit an immune response, when presented to the immune system of a host. In particular, such an epitope can comprise or consist of a stretch of 8, 9, 10, 11, 12, 13, 14, 15 or 16 amino acid residues. It may alternatively consist in a full-length antigen or consist in antigen(s) fragment(s).

Figure 12:
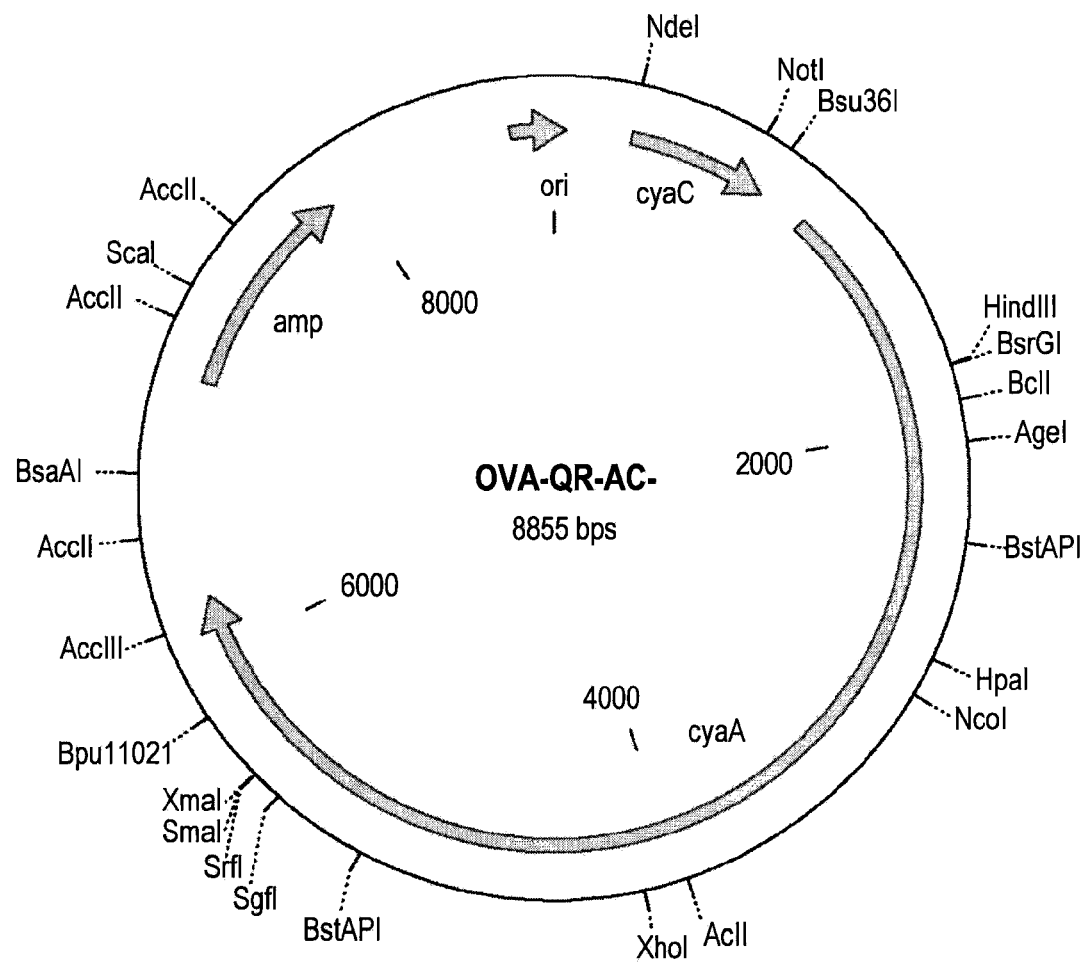

In a specific embodiment, a polypeptide derivative according to the invention can be encoded by a plasmid which corresponds to the OVA-QR-AC⁻ plasmid deposited under accession number CNCM I-4137 (FIG. 12) in which the DNA sequence encoding the "OVA" antigenic sequence is replaced by a DNA sequence encoding an antigenic sequence comprising one or more epitopes.

The polypeptidic molecule suitable for eliciting an immune response is especially one eliciting a T-cell immune response, including as an example a CTL response. The polypeptidic molecule suitable for eliciting an immune response can also be one eliciting a B-cell immune response.

In specific embodiments, the heterologous antigen is selected from the group consisting of an antigen of a bacterial pathogen, a tumoral cell antigen, a viral antigen, a retroviral antigen, a fungus antigen or a parasite cell antigen.

A molecule of interest can be especially an antigen selected from the group consisting of: a Chlamidia antigen, a Mycoplasma antigen, a hepatitis virus antigen, a poliovirus antigen, an HIV virus antigen, an influenza virus antigen, a choriomeningitis virus antigen, a tumor antigen, or a part of any of these antigens which comprises at least an epitope.

In a preferred embodiment of the polypeptide derivative of the invention, the amino acid sequence of each of said molecule(s) suitable for eliciting an immune response comprises or consists of an amino acid sequence of a Chlamidia antigen, a Mycoplasma antigen, a hepatitis virus antigen, a poliovirus antigen, an HIV virus antigen, an influenza virus antigen, a choriomeningitis virus sequence, a tumor antigen, or comprises or consist of a part of an amino acid sequence of any these antigens which comprises at least one epitope.

In a particularly preferred embodiment, the molecule of interest is a tumor associated antigen (TAA). Tumor-associated antigens have been characterized for a number of tumors such as for example: Melanoma, especially metastatic melanoma; Lung carcinoma; Head & neck carcinoma; cervical carcinoma, Esophageal carcinoma; Bladder carcinoma, especially infiltrating Bladder carcinoma; Prostate carcinoma; Breast carcinoma; Colorectal carcinoma; Renal cell carcinoma; Sarcoma; Leukemia; Myeloma. For these various histological types of cancers, it has been shown that antigenic peptides are specifically expressed on tumor samples and are recognized by T cells, especially by $CD8^+$ T cells or $CD4^+$ T cells.

A review of peptides found as tumor-associated antigens in these types of tumors is made by Van der Bruggen P. et al (Immunological Reviews, 2002, vol 188:51-64). Especially, the disclosure of the peptides contained in table 3 of said review is referred to herein as providing examples of such tumor-associated antigens and said table 3 is incorporated by reference to the present application.

The following antigens are cited as examples of tumor-associated antigens recognized by T cells, according to the publication of Kawakami Y. et al (Cancer Sci, October 2004, vol. 95, no. 10, p 784-791) that also provides methods for screening these antigens or further one: antigens shared by various cancers, including MAGE (especially in Melanoma), NY-ESO-1, Her2/neu, WT1, Survivin, hTERT, CEA, AFP, SART3, GnT-V, antigens specific for some particular cancers such as βbeta-catenin, CDK4, MART-2, MUM3, gp100, MART-1, tyrosinase for Melanoma; bcr-abl, TEL-AML1 for Leukemia; PSA, PAP, PSM, PSMA for prostate cancer; Proteinase 3 for myelogenous leukemia; MUC-1 for breast, ovarian or pancreas cancers; EBV-EBNA, HTLV-1 tax for lymphoma, ATL or cervical cancer; mutated HLA-A2 for Renal cell cancer; HA1 for leukemia/lymphoma. Tumor-associated antigens in animals have also been described such as Cycline D1 and Cycline D2 in tumors affecting cats or dogs.

Tumor-associated antigens recognized by T cells have also been disclosed in Novellino L. et al (Immunol Immunother 2004, 54:187-207).

More generally, TAA of interest in the present invention are those corresponding to mutated antigens, or to antigens that are overexpressed on tumor cells, to shared antigens, tissue-specific differenciation antigens or to viral antigens.

In a particular embodiment of the invention, the tumor-associated antigen is an antigen of papillomavirus (HPV) or is tyrosinase.

According to another particular embodiment of the invention, the amino acid sequences of the polypeptidic molecules which comprise or consist of an epitope have been modified with respect to their native amino acid sequence, for example in order to decrease the number of negatively charged amino acid residues within the sequence. Such a modification can be obtained by removing some of these negatively charged amino acid residues or also by adding some positively charged amino acid residues, especially as flanking residues of the epitopes. Polypeptides thus comprising less negatively charged residues might favour the translocation of the catalytic domain of the polypeptide derivative of the invention in the cytosol of target cells.

The amino acid sequences of the polypeptidic molecules which comprise or consist of an epitope or an antigen can also be designed in such a way that they are unfolded when they are inserted in the polypeptide derivative of the invention, which improves efficiency of the internalization of the molecule(s) of interest according to the invention into the target cells. Such unfolding in polypeptides which undergo folding as a consequence of their amino acid content, can be obtained for instance, by removing or substituting cystein residues in order to avoid formation of disulfide bonds that may be involved in folding of polypeptides. In some cases, it is possible to prevent folding of the polypeptides by preparing them in the presence of reducing agents to enable avoiding in vivo refolding.

In a particular embodiment, the amino acid sequences, especially the antigen, can comprise or consist of cryptic epitopes.

The inventors have indeed determined that polypeptide derivative constructs, which comprise (i) a polypeptide of the invention which is a mutant of a CyaA protein (polypeptide mutant) according to the definitions disclosed herein and (ii) a polypeptidic molecule having an amino acid sequence bearing one or several antigenic fragments of one or several antigens, enable cryptic epitopes of said antigens to become immunogenic as a result of their presentation in the constructs. Especially, said constructs involving mutant polypeptides as defined in the present invention comprising polypeptidic molecule(s) derived from antigens of interest for especially prophylactic or therapeutic applications, including immunotherapeutic vaccination, purposes are processed in target cells where the polypeptidic molecule(s) is allowed to be internalized as a result of the translocation of the N-terminal domain of the mutant polypeptide. Such processing enables epitopes presentation through the class I MHC molecules of the target cells, and said epitopes can comprise cryptic epitopes of the antigen which are allowed to become immunogenic and in particular to raise a T-cell response in a host, especially a CTL response.

The invention thus also relates to a polypeptide derivative, in particular to a recombinant protein comprising one or several polypeptidic molecules having an amino acid sequence bearing one or several epitopes of one or several antigens, or bearing said antigen(s) said amino acid sequence(s) of said polypeptidic molecule(s) being inserted in the same or in different sites, especially in different permissive sites of a mutant polypeptide according to the invention, said recombinant protein retaining the property of the CyaA toxin to target antigen presenting cells (APC), wherein at least one of said epitope(s) is a subdominant cryptic T-cell epitope and wherein said polypeptide derivative, especially said recombinant protein, is capable of eliciting an antigen-specific response against said polypeptidic molecule(s).

In a specific embodiment of the polypeptide derivative according to the invention, the one or more amino acid sequences are inserted into one or more sites, especially permissive sites.

For the present invention, a "permissive site" is a site of the sequence of the CyaA protein where a polypeptide can be inserted without substantially affecting the desired functional properties of the CyaA protein especially without substantially affecting the targeting of cells, particularly the targeting of antigen presenting cells (APC) by CyaA, including without substantially affecting the specific binding to the CD11b/CD18 receptor and advantageously without substantially affecting the domains of the protein involved in the process of translocation of the CyaA N-terminal domain into a target cell.

Methods to select for permissive sites are presented for example in WO93/21324, in Ladant et al., 1992, and in Osicka et al., 2000 (Infection and Immunity, 2000, 68(1):247-256). In particular, a methodology using a double selection (resistance to an antibiotic and calorimetric test on dishes by a-complementation) enables to identify readily oligonucleotides insertions (which preserve the reading frame) in the portion of the gene coding for the N-terminal catalytic domain of the toxin. The functional consequences of these mutations on the catalytic activity of the toxin may be readily analysed, both genetically (functional complementation of an E. coli cya⁻ strain) and biochemically (characterization of the stability of the modified adenylcyclases, of their enzymatic activity, of their interaction with caM, etc.). This methodology has enabled a large number of mutations to be screened in order to identify the sites which are potentially advantageous for the insertion of antigenic determinants.

Permissive sites of the Bordetella pertussis adenylate cyclase allowing translocation of CyaA catalytic domain and hence translocation of amino acid sequences inserted into such permissive sites include, but are not limited to, residues 137-138 (Val-Ala), residues 224-225 (Arg-Ala), residues 228-229 (Glu-Ala), residues 235-236 (Arg-Glu), and residues 317-318 (Ser-Ala) (Sebo et al., 1995). The following additional permissive sites are also included in embodiments of the invention: residues 107-108 (Gly-His), residues 132-133 (Met-Ala), residues 232-233 (Gly-Leu), and 335-336 (Gly-Gln) and 336-337. However, other permissive sites may be used in the present invention, that can be identified for example by use of the methodology indicated above, especially sites between residues 400 and 1700 of the CyaA protein.

For other Bordetella species corresponding permissive sites can be defined by comparison of sequences and determination of corresponding residues.

According to another embodiment, the one or more amino acid sequence polypeptide can also or alternatively be inserted at one and/or the other extremities (ends) of the polypeptide of the invention, preferably at the N-terminal end of the mutant CyaA polypeptide lacking all or part of the N-terminal catalytic domain of the Bordetella pertussis CyaA protein, and more particularly lacking residues 1-373.

According to a specific embodiment, the one or more amino acid sequences suitable for eliciting an immune response, is grafted onto an amino acid residue of said polypeptide.

According to the invention, the "combination" (or insertion) of an amino acid sequence with the CyaA mutant polypeptide to provide a so-called polypeptide derivative, also referred to as a "recombinant protein" or a "hybrid protein", encompasses genetic insertion especially by available DNA technology. Alternatively, "combination" also encompasses non genetic insertion, including chemical insertion for instance covalent coupling carried out especially at one extremity of the amino acid sequence, or non covalent coupling. Non-genetic insertion can especially be of interest when the amino acid sequence to be inserted is synthetic or semi-synthetic. Methods for coupling a drug to a polypeptide are well known in the Art and comprise for example disulfide linkage by using N-pyridyl sulfonyl-activated sulfhydryl.

In particular, it is possible to graft molecules to the polypeptides of the invention by a chemical linkage or by genetic insertion for in vivo targeting to CyaA target cells, such as APC, for example CD11b/CD18 positive cells and particularly to the cytosol of said cells. Indeed, when coupling a molecule corresponding to a given CD8+ T-cell epitope to the catalytic domain of detoxified CyaA, either by means of a disulfide bond or by genetic insertion, it has been found that the engineered molecule can elicit in vivo specific CTL response, thereby showing that said CD8+ T-cell epitope is translocated into the cytosol of CD11b-expressing cells.

In a preferred embodiment of the invention, the mutant CyaA polypeptide is used in the manufacturing of a proteinaceous vector or in the preparation of a composition specifically designed to prime CD8+ cytoxic T-cell response (CTL response) when said response follows the targeting of the mutant CyaA polypeptide modified (especially recombined or conjugated) with a molecule of interest to CD11b expressing cells, followed by the translocation of the molecule of interest to the cytosol of said CD11b expressing cells, and in particular to myeloid dendritic cells. In this context, the molecule of interest is or comprises preferably an epitope or an antigen.

In another preferred embodiment of the invention, the mutant CyaA polypeptide is used in the manufacturing of the proteinaceous vector or in the preparation of a composition specifically designed to prime CD4+ cells response when said response follows the targeting of the adenylcyclase modified (especially recombined or conjugated) with a molecule of interest to CD11b expressing cells, in particular myeloid dendritic cells. In this context, the molecule of interest is or comprises preferably an epitope or an antigen.

The mutant polypeptides can also be used in the manufacturing of a proteinaceous vector for targeting of a prophylactic or a therapeutic compound to CD11b expressing cells. In this context, in one specific embodiment of the invention, the so-called molecule of interest has a prophylactic or therapeutic value and in particular is a drug. Said prophylactic or therapeutic compound and in particular said drug may be chemically or genetically coupled to the mutant polypeptide. Method for coupling a compound to a polypeptide are well known in the Art and comprise for example disulfide linkage by using N-pyridyl sulfonyl-activated sulfhydryl. In one embodiment, a molecule of interest is an anti-inflammatory compound which is, when coupled to the mutant polypeptide, specifically targeted to the surface of the cells involved of the inflammatory response, such as dentritic cells or neutrophils.

More specifically, antigen presentation for selective CD8+ cytotoxic cells priming is mainly performed by myeloïd dendritic cells.

Accordingly, in a specific embodiment, the mutant CyaA polypeptide used for the manufacturing of proteinaceous vector is a genetically modified adenylcyclase containing one or more molecule(s) chemically coupled by means of a disulfide bond to genetically inserted cysteine residue(s) located within the catalytic domain of the mutant CyaA polypeptide. Indeed, multiple molecules can be chemically coupled to the mutant CyaA polypeptide by means of a disulfide bond to different cysteine residues located at different permissive sites within the catalytic domain.

The mutant polypeptides or polypeptide derivatives according to the invention are suitable for use in therapy or prophylaxis.

By therapy or therapeutic effect it is intended any effect which is beneficial to the condition of a patient, be it curative or sufficient to limit the symptoms or the consequences of a pathological condition, including limiting the progression of a pathological condition. By therapy or therapeutic effect is also encompassed the prevention of the onset of pathological condition.

The mutant polypeptides or polypeptide derivatives according to the invention are in particular suitable to elicit a cell-mediated immune response such as a T-cell immune response or a B-cell immune response in a host in need thereof. It includes CTL and Th, especially Th1 response, including $CD4^+$ T cell response and/or $CD8^+$ T cell response.

The ability of a polypeptide derived from CyaA protein to elicit a cell-mediated immune response may be sufficient to prevent tumor growth in vivo or even to enable tumor regression in an animal. It may also be enhanced by activation of innate component of the immune response through TLR activation and by down activating the regulatory component of the immune response through the use of chemotherapeutic agents. The invention provides means which should enable such results to be obtained in improved safety conditions as a result of the combined mutations E570Q and K86oR, which have been selected.

The present invention is thus also directed to therapeutic methods comprising administration to an animal or human patient of the mutant polypeptide or polypeptide derivative according to the invention to a patient to elicit a T-cell immune response or a B-cell immune response in a host in need thereof.

The mutant polypeptides or polypeptide derivatives according to the invention can in particular be used for the prevention or the treatment of a disease selected from neoplasia, cancers and infectious diseases selected from viral-, retroviral-, bacterial- or fungal-induced diseases. In particular, the polypeptide derivatives can be used for the treatment of HIV infections in a patient.

It is especially provided that in a particular embodiment of the invention, the CyaA mutant polypeptide or polypeptide derivative is suitable for the treatment of infiltrating or vascularized tumors versus superficial tumors or for the treatment of metastatic tumors versus primary tumors, in accordance with the acknowledged clinical criteria for the classification of tumors.

Solid tumors are especially a target for the treatment through the use of the polypeptide derivative of the invention.

Among tumors which may be candidates for the treatment with the polypeptide derivative of the invention, the following, for which tumor-associated antigens have been characterized, are described as examples:

Melanoma, especially metastatic melanoma; Lung carcinoma; Head & neck carcinoma; cervical carcinoma, Esophageal carcinoma; Bladder carcinoma, especially infiltrating Bladder carcinoma; Prostate carcinoma; Breast carcinoma; Colorectal carcinoma; Renal cell carcinoma; Sarcoma; Leukemia; Myeloma. For these various histological types of cancers, it has been shown that antigenic peptides are specifically expressed on tumor samples and are recognized by T cells, especially by $CD8^+$ T cells or $CD4^+$ T cells.

The invention further relates to the use of a polypeptide derivative according to the invention, for the preparation of a therapeutic composition for the treatment of a disease selected from neoplasia, cancers and infectious diseases selected from viral- or retroviral-induced diseases.

In a preferred embodiment, the polypeptide or polypeptide derivative according to the invention can be administered to the patient in combination with an adjuvant and/or in combination with another therapeutically active molecule or agent.

In the context of the present invention said "another therapeutically active molecule or agent" is one which may be beneficial to the condition of a patient to whom it is administered. It is especially an active principle suitable for use in the manufacturing of a drug. It may be a compound suitable to either, potentiate increase or modulate the effect of an therapeutically active principle.

The mutant CyaA poplypeptide or the poplypeptide derivative thereof can be administered with a therapeutically active molecule or agent, in particular one suitable for eliciting an immune response in a patient.

In particular, mutant CyaA poplypeptide or the poplypeptide derivative thereof can be administered with a therapeutically active agent suitable for modulating a cell response in a patient, in particular by lowering or blocking regulatory T cells immunosuppressive capacity.

According to a particular embodiment of the invention, such an effect on a regulatory cell response may be obtained with an agent modulating a regulatory T cell and/or modulating another cell suppressive response, such as the myeloid suppressive cells response, said agent targeting said regulatory cells, especially T cells, by depleting or inactivating these cells (such as with CD25-specific antibody, or cyclophosphamide), altering trafficking of said cells, especially regulatory T cells (such as CCL22-specific antibody) or altering differentiation and signalling of said cells (such as by blocking FOXP3 (forkhead box P3) signal).

According to a particular embodiment of the invention, the agent modulating a regulatory cell response targets suppressive molecules, especially such molecules present on APCs (such as B7-H1, B7-H4, IDO (indoleamine 2,3-dioxygenase) or arginase) or on T cells (such as CTLA4 (cytotoxic T-lymphocyte-associated antigen 4) or PD1 (programmed cell death 1)), or targets soluble immunosuppressive molecules (such as TGF beta (transforming growth factor), IL-10, VEGF (vascular endothelial growth factor), COX2 (cyclooxygenase 2)).

As examples of agents having an effect on a regulatory cell response, cytotoxic agents are proposed, that can kill regulatory T cells or other immunosuppressive cells, or that can block their activity and/or development and/or accumulation.

In a particular embodiment of the invention, the agent modulating the regulatory cell response, especially a regulatory T cell response, is a chemotherapeutic agent. Especially it is selected among chemotherapeutic agents known as anti-cancer agents and used in chemotherapy. Such agents include those helping to reduce the tumor burden, those acting by increasing sensitivity of tumor cells to treatment or those enabling killing or inactivating immune regulatory cells. The chemotherapeutic agents used within the frame of the invention thereby enhance antitumor immunity.

In a particular embodiment of the invention, the chemotherapeutic agent is an alkylating agent. Especially, it is Cyclophosphamide (CTX) (Sigma, Steinheim, Germany). Cyclophosphamide is capable of depleting or inactivating regulatory T cells.

In another particular embodiment of the invention, the chemotherapeutic agent is an intercalating agent.

In a particular embodiment, the chemotherapeutic agent is Doxorubicin (DOX) (Calbiochem, La Jolla, Calif., USA).

The chemotherapeutic agent is advantageously administered by low doses.

The mutant CyaA poplypeptide or the poplypeptide derivative thereof can also be administered with an adjuvant component, suitable for activating the innate immune response primed by a tumor in a patient.

In a particular embodiment of the invention, the adjuvant component is selected in the group of components consisting of nucleic acids, peptidoglycans, carbohydrates, peptides, cytokines, hormones and small molecules, wherein said adjuvant component is capable of signalling through pattern-recognition receptors (PRRs).

PRRs are known to mediate the innate immune response to pathogens, and to tumors, by recognition of so-called evolutionarily conserved signatures from pathogens (pathogen-associated molecule patterns, PAMPs). PRRs are present on a variety of immune cells including dendritic cells, natural killer cells, B cells, and also on some non immune cells such as epithelial cells or endothelial cells. PRRs and their involvement in the innate immune response are described in Pashine A. et al (Nature medicine supplement volume 11, No4, April 2005).

In particular an adjuvant component for the activation of the innate immune response can target PRRs and therefore activate signalling through PRRs, wherein said PRRs encompass Toll-like receptors or nucleotide-binding oligomerization domain (NOD) or C type lectin.

In a particular embodiment of the invention, the adjuvant component is a Toll-like receptor (TLR) agonist. The Toll-like receptor agonist is especially formulated to efficiently activate the innate immune system of a patient. Said TLR agonist is capable of binding the TLR, i.e., is a ligand of the TLR and is furthermore capable of enhancing the immune response elicited under the control of said TLR.

For illustration, TLR agonists are selected from the group of TLR-9, TLR-8, TLR-3 and TLR-7 agonists. However agonists of other TLR receptors may be used to perform the invention, such as agonists of the TLR2, TLR4, TLR5 receptors.

The TLR agonist used in the invention can be a natural or a synthetic agonist. It can be a combination of different agonists of the same or of different toll-like receptors.

According to a particular embodiment of the invention, the TLR agonist is an immunostimulatory nucleotide sequence, especially a stabilized nucleotide sequence, for example stabilized as a result of structure modification such as phosphorothioate modification. The nucleotide sequence can also be protected against degradation by specific formulation. Especially liposome formulation thereof, e.g. liposome suspension, can be advantageous for the efficient administration of the immunostimulatory nucleotide sequence.

In a particular embodiment of the invention, the immunostimulatory nucleic acid sequence is a single-stranded RNA.

In a particular embodiment of the invention, the immunostimulatory nucleotide sequence comprises a CpG motif and especially is a CpG oligonucleotide (CpG ODNs). As an example of suitable CpG oligonucleotides the invention provides TLR-9 ligands such as Type A CpG ODN, i.e., CpG 2216 having nucleotide sequence 5'-GGGGGAC-GATCGTCGGGGGG-3' (SEQ ID NO: 7) or Type B CpG ODN, i.e., CpG 1826 having nucleotide sequence 5'-TCCAT-GACGTTCCTGACGTT-3' (SEQ ID NO: 8).

CpG oligonucleotide can be used after being complexed with DOTAP (Roche Manheim, Germany), in order to protect it against degradation and to facilitate its uptake.

According to another particular embodiment of the invention, the TLR agonist is a small molecule. Small molecules suitable as TLR agonists are for example imidazoquinoline amine derivatives, such as the one named R848 (resiquimod), i.e., 4-amino-2-ethoxymethyl-a,a, dimethyl-1-H-imidazo[4,5c]quinoline-1-ethanol available from Invivogen, as TLR-7 ligand, or the one named R837 (imiqimod) available from Aldara as TLR-7 agonist.

Other molecules suitable as TLR agonists are polyuridine (pU) as TLR-3 ligand, or polycytidylic acid (PIC) as TLR-7 ligand.

These molecules can be formulated to facilitate their uptake and/or to protect them from degradation. These molecules can also be prepared as a liposome formulation, especially as a liposome suspension, for administration to a patient.

According to another particular embodiment of the invention, the adjuvant component can be a cell-based adjuvant component. An example thereof is dendritic cells that are known to be able to prime lymphocyte response, such dendritic cells being possibly conditioned ex vivo prior to their administration, in order to increase their activity of stimulation of the T cell response. Dendritic cells can hence be stimulated with adjuvants interacting with the PRRs, including TLR ligands or agonists (Pashine A. et al Nature Medicine Supplement Volume 11, No4, April 2005 p S63-S68).

Alternatively, the polypeptide or polypeptide derivative according to the invention can be administered to the patient without an adjuvant.

Indeed the inventors have previously shown that CTL specific for the vectorized antigen can be primed in vivo after a single intravenous injection of the recombinant toxin, especially with no need to provide an heterologous adjuvant. These results and in particular the specific targeting of the epitope to myeloid dendritic cells enable to bypass the requirement for adjuvant and CD4+ T cell help.

Therefore, the invention also relates to the use of a mutant CyaA polypeptide recombined with a molecule and especially a peptide of interest for the preparation of a composition formulated for intravenous administration and enabling a CD8+ T cell immune response in vivo, said composition being free of a heterologous adjuvant. The invention also concerns this composition as such.

The present invention is further directed to therapeutic methods comprising administration of the mutant polypeptide or polypeptide derivative according to the invention to an animal or human patient suffering from a disease selected from neoplasia, cancers and infectious diseases selected from viral-, retroviral-, bacterial- or fungal-induced diseases.

The mutant polypeptide or polypeptide derivative can in particular be administered with a therapeutically active molecule and/or an adjuvant.

The mutant CyaA polypeptide or the polypeptide derivative, the therapeutically active molecule and/or an adjuvant can be administered together as part of a pharmaceutical composition which further comprises a pharmaceutically acceptable carrier or excipient(s).

Alternatively, the various types of molecules described herein to carry out the invention used, can be administered separately either simultaneously in time (especially for the mutant CyaA polypeptide or the polypeptide derivative and the adjuvant) or separately in time (especially for the mutant CyaA polypeptide).

The administration of the therapeutically active molecule can alternatively be carried out prior and after the administration of the mutant CyaA polypeptide or the polypeptide derivative and/or the adjuvant. It can also be sequential in time.

A particular regimen that may be adopted is a repeated administration protocol, especially in a protocol which encompasses two rounds or more of administration of at least one of the compounds selected from the mutant CyaA polypeptide or the polypeptide derivative, the therapeutically active agent and/or the adjuvant.

The invention is also directed to a pharmaceutical composition which comprises a mutant CyaA polypeptide or a polypeptide derivative according to the invention, a pharmaceutically acceptable carrier or excipients(s), and optionally an adjuvant and/or another therapeutically active molecule.

The invention is also directed to a kit of parts comprising the mutant CyaA polypeptide or the polypeptide derivative, a therapeutically active molecule and/or an adjuvant.

The compounds of the kit of parts or the composition of the invention can especially be given to the patient through intravenous administration, intratumoral administration or subcutaneous administration.

The kit of parts of the invention or the composition has the ability to target (i) the adaptive immune response, through the mutant CyaA polypeptide or the polypeptide derivative disclosed in the present application, (ii) to downregulate the regulatory immune response through the therapeutically active agent, and if the adjuvant is present, to target (iii) the innate component of the immune response, by activating said innate response through the adjuvant.

The invention also relates to a method of treatment of a patient in need thereof, either a human or an animal patient, comprising the step of administering the components of the kit of parts or of the composition herein disclosed.

The invention in particular also relates to a new immunogenic composition formulated for administration, especially intravenous administration, in an animal or human host, characterized in that it comprises a recombinant CyaA polypeptide derivative which comprises an antigen inserted in the catalytic domain.

The invention further relates to a pharmaceutical composition for administration in a human or an animal formulated for targeting a molecule of interest specifically to CD11b expressing cells characterized in that said molecule of interest is coupled to a mutant CyaA polypeptide as described herein.

In another specific embodiment, the pharmaceutical or immunogenic composition comprises a nucleic acid construction encoding the recombinant CyaA polypeptide derivative comprising a CyaA mutant polypeptide as defined herein coupled to a molecule of interest.

Furthermore, the invention also relates to the use of the immunogenic composition as defined above for the preparation of a vaccine or an immunotherapeutic composition, for administration to an animal or human host.

As used herein, the term "immunotherapeutic composition" relates to a composition which leads to an immunological response and which is associated to therapeutic treatments, such as treatment against neoplasia, cancers, viral infections, fungal infections, parasites infections or bacterial infections.

The invention further relates to a method to immunize an animal or human host, wherein said method comprises the steps of:

a) providing an immunogenic composition as defined above;

b) administering said immunogenic composition, preferably via intravenous route, to said host in order to promote an immune response.

In particular, the immunogenic compositions of the invention are capable of inducing or stimulating, in vivo or in vitro an immune cell response involving specifically dendritic cells. The immunogenic compositions of the invention can in particular be used for preventive or therapeutic vaccination of a patient.

As a consequence, in a specific embodiment, the immunogenic or pharmaceutical composition is advantageously devoid of priming adjuvants commonly used in the Art, such as aluminium hydroxide.

The invention further relates to a method for the preparation of a proteinaceous vector suitable for the delivery of a molecule of interest into a cell comprising binding the molecule of interest to a CyaA mutant polypeptide as defined herein.

The invention further relates to nucleic acid molecules, in particular DNA or RNA molecules, which encode a polypeptide or polypeptide derivative as defined above.

The invention is also directed to eukaryotic or prokaryotic cells which comprise the nucleic acid molecules as defined above.

The invention also relates to eukaryotic cells, preferably mammalian cells, which comprise a mutant CyaA polypeptide or polypeptide derivative as defined above. In a preferred embodiment, the cells are human cells.

The invention further relates to eukaryotic cells, preferably mammalian cells, transformed with the proteinaceaous vector as defined above.

FIGURES

FIG. 1. Substitutions in the pore-forming and acylation domains synergize in decreasing the specific hemolytic activity of CyaA. (A) Sheep erythrocytes ($5 \times 10^8$/ml) in TNC buffer were incubated with 5 µg/ml of enzymatically active CyaA proteins at 37° C. After 30 min, aliquots of cells suspensions were washed repeatedly to remove unbound CyaA and used to determine the amount of cell-associated and cell-invasive AC activity. Hemolytic activity was measured after 5 hours of incubation as the amount of released hemoglobin by photometric determination ($A_{541}$). Activity of intact CyaA was taken as 100%. (B) The reduced cell binding activity of proteins with the K860R substitution was compensated for by increasing their concentration from 5 µg/ml to 25 µg/ml. Activities of CyaA/233OVA (CyaA/OVA) in the presence were taken as 100% value. The results represent average values from at least three independent experiments performed in duplicates. The asterisks indicate statistically significant differences (**, p<0.001) from activities of CyaA (FIG. 1A) or CyaA/OVA (FIG. 1B).

FIG. 2. CyaA/OVA/E570Q+K860R binds and translocates into CD11b$^+$ monocytes. (A) J774A.1 cells ($10^6$/ml) were incubated in D-MEM for 30 min at 4° C. with 2.5 µg/ml of CyaA, washed repeatedly, and the amount of cell-associated AC activity was determined in cell lyzates. To block the CD11b/CD18 receptor, cells were incubated for 30 min with the CD11b-specific antibody M1/70 (Exbio, Czech Republic) at a final concentration of 10 µg/ml prior to addition of CyaA (**, p<0.001). (B) The AC domain translocation capacity of constructs was assessed as the capacity to penetrate cells and convert cytosolic ATP to cAMP. J774A.1 cells were incubated with CyaA constructs for 30 minutes at 37° C. and the amounts of cAMP accumulated in cell lyzates were determined (41). The CD11b/CD18 receptor was blocked with M1/70 as above. Results representative of three independent determinations performed in duplicates are shown.

FIG. 3. E570Q+K860R toxoid does not permeabilize J774A.1 cells. Whole-cell patch-clamp measurements were performed on single J774A.1 cells at room temperature exposed to 1 µg/ml of (A) CyaA/233OVA/AC$^-$ or (B) CyaA/233OVA/E570Q+K860R/AC$^-$ proteins as described in Materials and Methods. The shown curves are representative of six determinations in 3 independent experiments.

Figure 4:
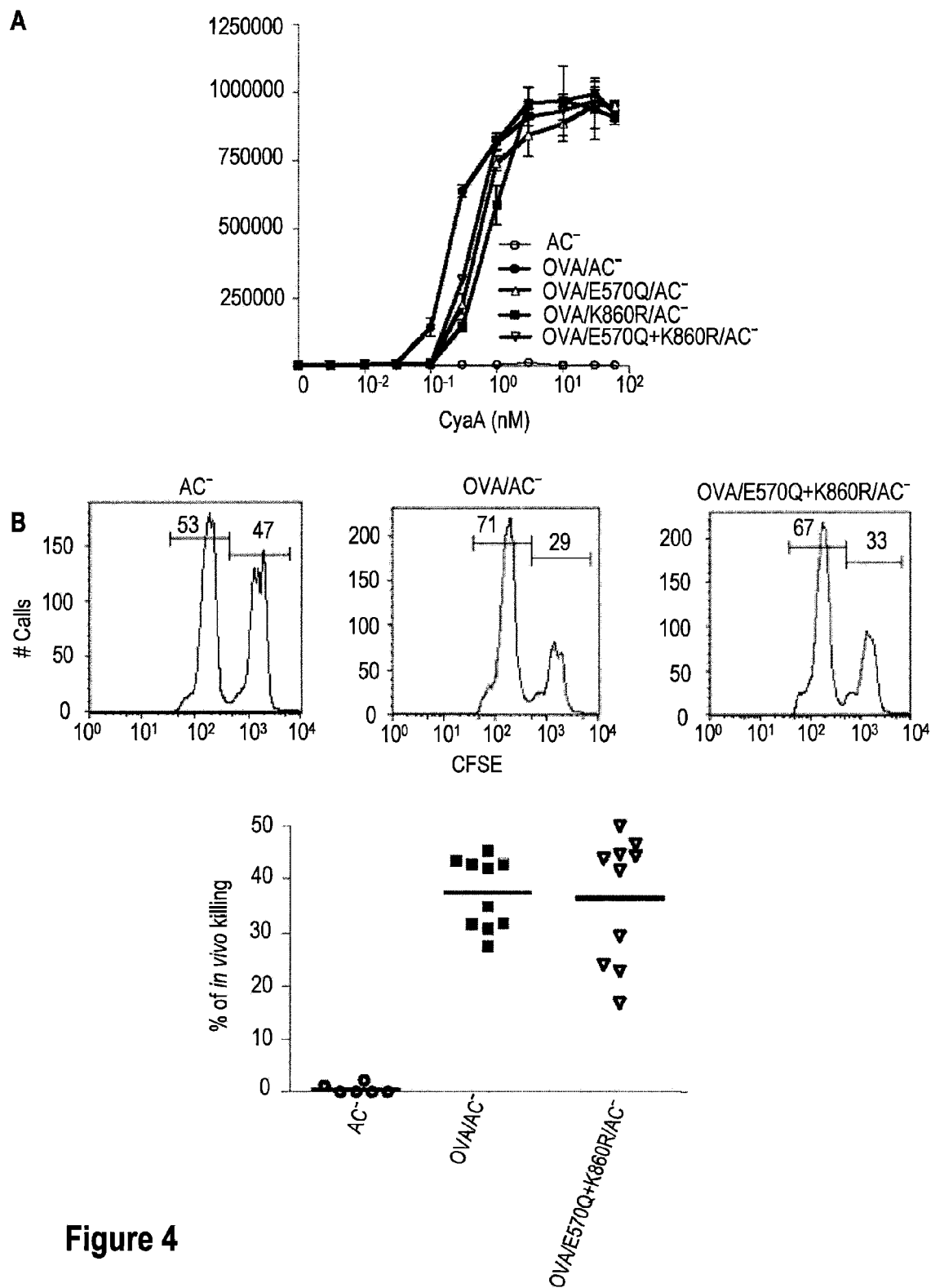

FIG. 4. Toxoid with E570Q+K860R substitutions delivers the OVA T-cell epitope for presentation by MHC class I molecules and induction of CD8+CTLs. (A) BMDC ($3 \times 10^5$ cells/well) used as APCs were incubated in the presence of indicated concentrations (0 to 60 nM) of the toxoids harboring the OVA epitope or with mock CyaA/AC$^-$. Upon coculture for 24 hours with B3Z T cells (1×10⁵ cells/well), IL-2 secretion by the stimulated B3Z cells was determined by the CTLL proliferation method. Results are expressed as Δcpm of incorporated [³H]thymidine (cpm in the presence of toxoid−cpm in the absence of toxoid)±SD and are representative of five independent experiments. (B) Analysis of the induction of OVA (SIINFEKL (SEQ ID NO: 9))-specific CTL responses by in vivo killing assay. On day 0, mice received 50 μg i.v. of mock AC⁻ or OVA/AC⁻ toxoids and on day 7, they were i.v. injected with a mixture (1:1) of OVA (SIINFEKL (SEQ ID NO: 9)) peptide-loaded CFSE$^{high}$ and unloaded CFSE$^{low}$ splenocytes. The number of CFSE-positive cells remaining in the spleen after 20 h was determined by FACS analysis, as documented for one representative in vivo killing assay in the upper panel assembly of plots, where percentages of cells in the gates are indicated. The lower panel shows pooled results of in vivo killing assays for three independent experiments. Statistical significance was determined by the Student t test (p=0.75 for OVA/AC⁻ vs. OVA/E570Q+ K860R/AC").

Figure 5:
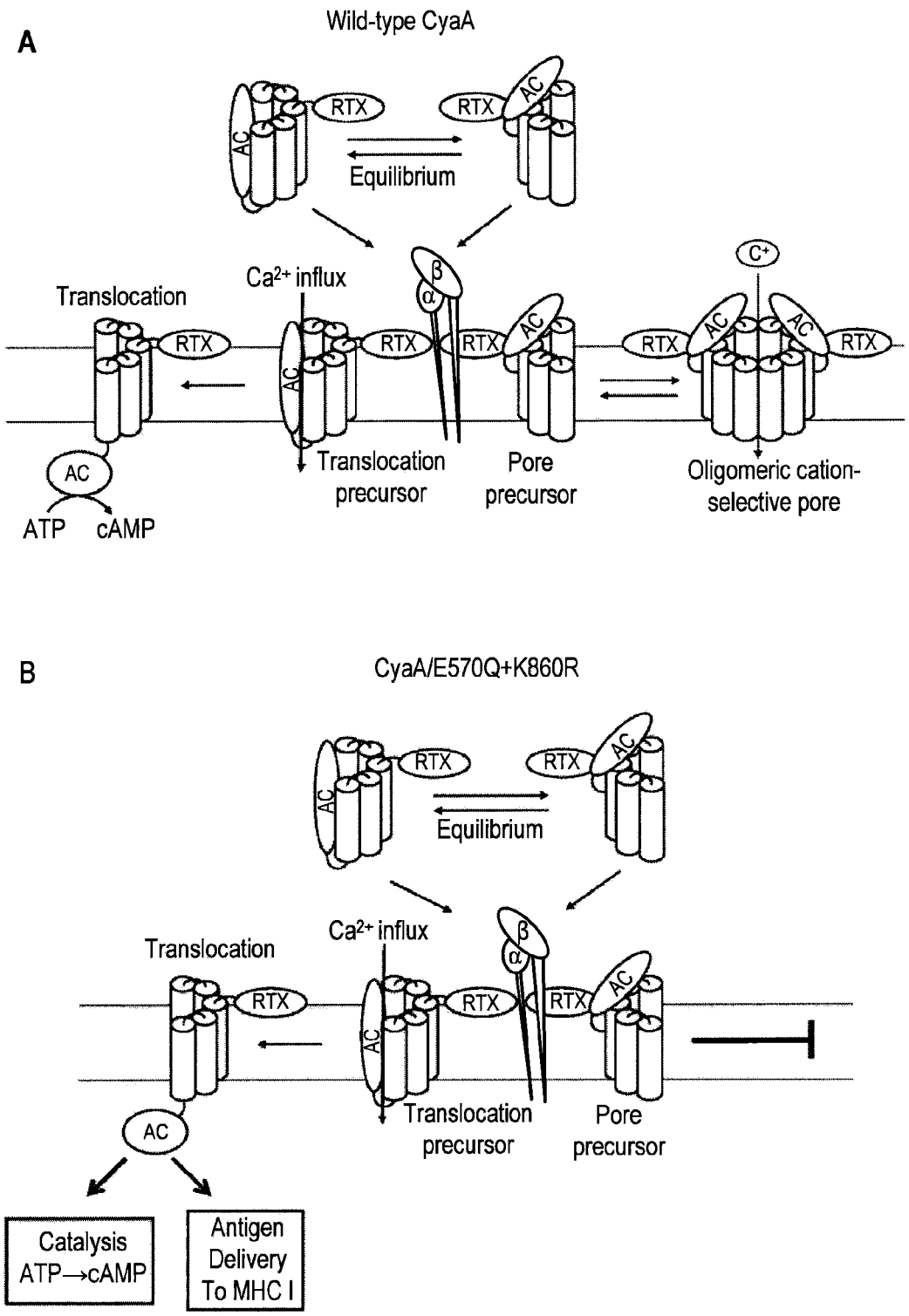
Figure 10:
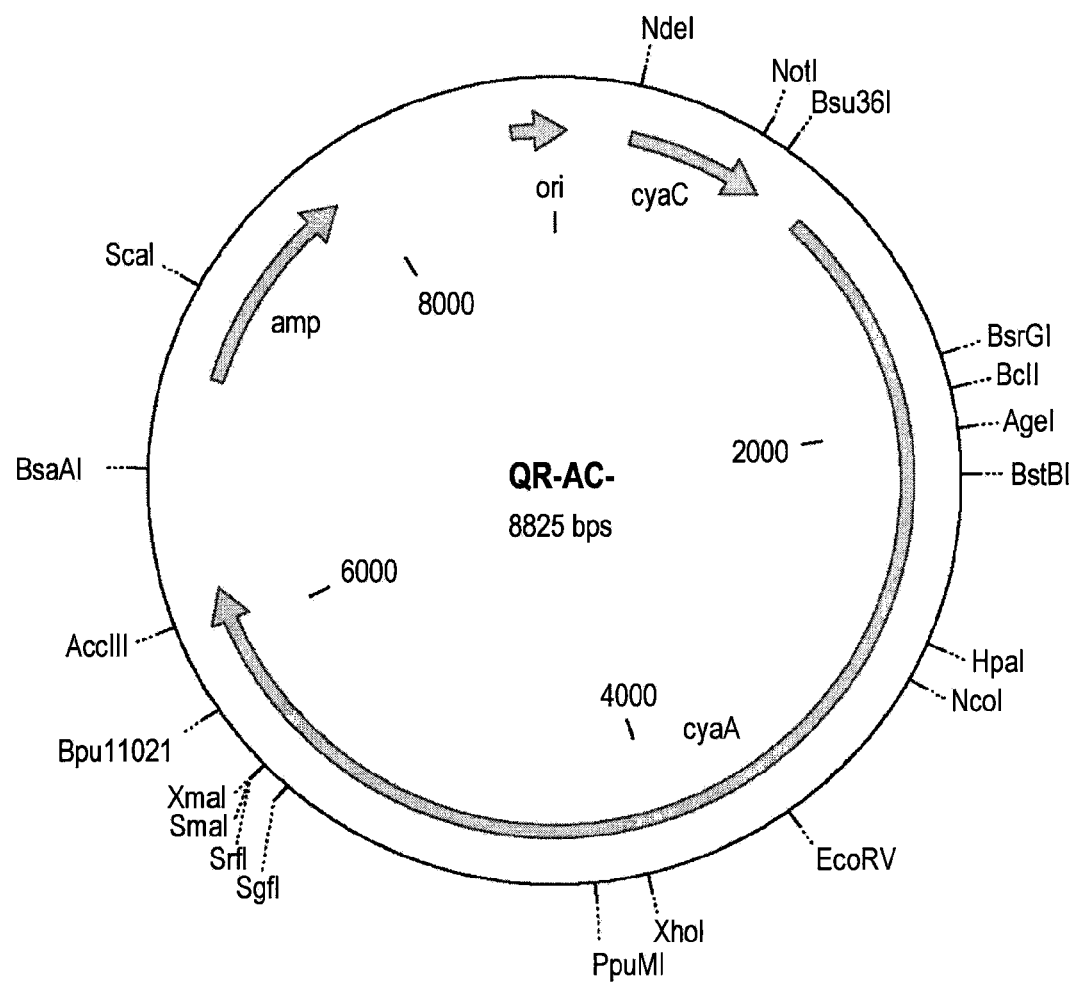

FIG. 5. Model of CyaA action on the membrane. (A) The model predicts an equilibrium between two conformers of CyaA in solution, each of them inserting into cell membrane in different a conformation. One would yield a monomeric CyaA translocation precursor, delivery of the AC domain into cytosol and concomitant influx of calcium ions into cells. The conformer would insert as pore precursor oligomerizing into a CyaA pore. (B) The synergic effect of the E570Q and K860R substitutions would selectively block the capacity of CyaA pore precursors to oligomerize into a pore, while the capacity of translocation precursors to deliver the AC domain across membrane would remain unaffected.

FIG. 6. Amino acid sequence of the *Bordetella pertussis* CyaA toxin (SEQ ID NO: 1)

FIG. 7. Amino acid sequence of the *Bordetella pertussis* CyaA/E570Q+K860R mutant (SEQ ID NO: 2)

FIG. 8. Amino acid sequence of the *Bordetella pertussis* CyaA/E570Q+K860R/AC⁻ mutant (SEQ ID NO: 3)

FIG. 9. Amino acid sequence of the *Bordetella pertussis* CyaA/233OVA/E570Q+K860R/AC⁻ mutant (SEQ ID NO: 4)

FIG. 10. Plasmid encoding the CyaA/E570Q+K860R/$AC^-$ mutant (QR-$AC^-$).

FIG. 11. DNA sequence of the QR-AC plasmid encoding the CyaA/E570Q+K860R/$AC^-$ mutant (SEQ ID NO: 5)

FIG. 12. Plasmid encoding the CyaA/233OVA/E570Q+K860R/$AC^-$ mutant (OVA-QR-$AC^-$).

FIG. 13. DNA sequence of OVA-QR-$AC^-$ plasmid encoding the CyaA/2330VA/E570Q+K860R/$AC^-$ mutant (SEQ ID NO: 6)

EXAMPLES

Adenylate Cyclase Toxin Translocates Across Target Cell Membrane Without Forming a Pore

Materials and Methods

Construction, Production and Purification of CyaA proteins. The modifications yielding CyaA/$AC^-$, CyaA/233OVA, CyaA/E570Q and CyaA/K860R constructs were previously described (13, 20, 21) and were introduced into CyaA/233OVA/$AC^-$ individually or in combination. The CyaA-derived proteins were produced in *E. coli* XL-1 Blue and purified close to homogeneity as previously described (29). During the hydrophobic chromatography, the resin with bound toxin was repeatedly washed with 60% isopropanol (30) to reduce the endotoxin content of CyaA samples below 100 lU/mg of protein, as determined by the LAL assay QCL-1000 (Cambrex).

An *Escherichia coli* XL1-Blue strain (Stratagene) containing the QR-$AC^-$ plasmid (FIG. 10) which encodes the CyaA/E570Q+K860R/$AC^-$ mutant was deposited on Mar. 18, 2009 at the CNCM (Collection Nationale de Cultures de Microorganismes, France) under the accession number CNCM I-4136 (FIG. 10). The DNA sequence of the QR-$AC^-$ plasmid (SEQ ID No5) is disclosed in FIG. 11.

An *Escherichia coli* XL1-Blue strain (Stratagene) containing the OVA-QR-$AC^-$ plasmid (FIG. 12) which encodes the CyaA/233OVA/E570Q+K860R/$AC^-$ mutant was deposited on Mar. 18, 2009 at the CNCM (Collection Nationale de Cultures de Microorganismes, France) under the accession number CNCM I-4137. The DNA sequence of the OVA-QR-$AC^-$ plasmid (SEQ ID No6) is disclosed in FIG. 13.

Cell Binding and Hemolytic Activities on Sheep Erythrocytes. $5\times10^8$ washed sheep erythrocytes in 50 mM Tris pH 7.4, 150 mM NaCl and 2 mM $CaCl_2$ (TNC buffer) were incubated at 37° C. with 5 μg/ml of CyaA proteins and cell binding, cell-invasive AC and hemolytic activities of CyaA were determined as described in detail previously (13). Significance of differences in activity values was analyzed using a one-way analysis of variance (ANOVA) with Bonferroni post-test (SigmaStat v. 3.11, Systat, San Jose, Calif.).

Macrophage Binding, Elevation of cAMP and Cell Lysis Capacities of CyaA. J774A.1 macrophages ($10^6$) were incubated in D-MEM with 2.5 μg/ml of CyaA variants for 30 min at 4° C., prior to removal of unbound toxin by three washes in D-MEM. Cells were lyzed with 0.1% Triton X-100 for determination of cell-bound AC activity. For intracellular cAMP assays, $10^5$ cells were incubated with CyaA for 30 minutes in D-MEM with 100 μM IBMX (3-isobutyl-1-methylxanthin), the reaction was stopped by addition of 0.2% Tween-20 in 100 mM HCl, samples were boiled for 15 min at 100° C., neutralized by addition of 150 mM unbuffered imidazol and cAMP was measured as described (29). To block the CD11b/CD18 receptor, cells were preincubated for 30 min on ice with the CD11b-specific blocking MAb M1/70 (Exbio, Czech Republic) at a final concentration of 10 μg/ml prior to addition of CyaA. Toxin-induced lysis of J774A.1 cells was determined using the CytoTox 96 kit assay (Promega) as the amount of lactate dehydrogenase released from $10^5$ cells in 3 hours of incubation with 10 μg/ml of the appropriate protein at 37° C. in D-MEM as described (8). Significance of differences in activity values was analyzed as above.

Patch Clamp Measurements. Whole-cell patch-clamp measurements were performed on J774A.1 cells bathing in HBSS (140 mM NaCl, 5 mM KCl, 2 mM $CaCl_2$, 3 mM $MgCl_2$, 10 mM Hepes-Na, 50 mM glucose; pH 7.4). Fire-polished glass micropipettes with outer diameter of about 3 μm were filled with a solution of 125 mM potassium gluconate, 15 mM KCl, 0.5 mM $CaCl_2$, 1 mM $MgCl_2$, 5 mM EGTA, 10 mM HEPES-KOH pH 7.2. The resulting resistances of the microelectrodes were 3 to 5 MΩ. Cells were clamped at −40 mV, the data were filtered at 1 kHz and digitized at 2 kHz using Axopatch 200A amplifier, Digidata 1320A digitizer and PClamp-9 software package (Axon Instruments, Foster City, Calif.).

Mice and Cell Lines. Female C57BL/6 obtained from Charles River Laboratories were kept under specific pathogen-free conditions and manipulated according to institutional guidelines. CTLL-2 cells were obtained from ATCC. B3Z, a $CD8^+$ specific T cell hybridoma specific for the $K^b$ restricted OVA (SIINFEKL (SEQ ID NO: 9)) epitope, was provided by N. Shastri (University of California, Berkeley)

and maintained in the presence of 1 mg/ml G418 and 400 µg/ml hygromycin B in complete RPMI 1640 medium (Invitrogen Life Technologies) with 10% heat-inactivated FCS, 100 U/ml penicillin, 100 µg/ml streptomycin, and $5 \times 10^{-5}$ M 2-ME.

Antigen Presentation Studies. Bone Marrow Dendritic Cells (BMDC, $3 \times 10^5$ per well) used as APCs were incubated in the presence of various concentrations (0 to 60 nM) of the recombinant CyaNOVA/AC$^-$ carrying the OVA (SIINFEKL (SEQ ID NO: 9)) epitope or mock CyaA/AC$^-$ and cocultured for 24 hours with B3Z T cells ($1 \times 10^5$ per well), selectively recognizing the OVA SIINFEKL (SEQ ID NO: 9)/H-2K$^b$ MHC class I complexes. After 18 h of culture, supernatants were frozen for at least 2 h at $-80°$ C. The amount of IL-2 produced by the stimulated B3Z cells was then determined by the CTLL proliferation method. Briefly, $10^4$ cells of the IL-2-dependent CTLL line per well were cultured with 100 µl of supernatant in 200 µl of final volume. Twenty-four hours later, [$^3$H]-thymidine (50 µCi/well) was added and cells were harvested 6 h later with an automated cell harvester. Incorporated [$^3$H]-thymidine was detected by scintillation counting. Each point was done in duplicate and the experiment was repeated five times. Results are expressed in Δcpm of incorporated [$^3$H]-thymidine (cpm in the presence of toxoid—cpm in the absence of toxoid).

In vivo Killing Assay. For CTL priming, mice were immunized by i.v. injection with 50 µg of recombinant CyaA/OVA/AC$^-$ carrying the OVA (SIINFEKL (SEQ ID NO: 9)) epitope or mock CyaA/AC$^-$. Seven days after immunization, naive syngenic splenocytes were pulsed with OVA (SIINFEKL (SEQ ID NO: 9)) peptide (10 µg/ml) (30 min, 37° C.), washed extensively and labeled with a high concentration (1.25 µM) of carboxyfluoroscein succinimidyl ester (CFSE; Molecular Probes, Eugene, Oreg.). The nonpulsed control population was labeled with a low concentration (0.125 µM) of CFSE. CFSE$^{high}$- and CFSE$^{low}$-labeled cells were mixed in a 1:1 ratio ($5 \times 10^6$ cells of each population) and injected i.v. into mice. Spleen cells were collected 20 h after, washed and resuspended in FACS buffer (PBS supplemented with 1% BSA and 0.1% NaN$_3$). The number of CFSE-positive cells remaining in the spleen after 20 h was determined by FACS. The percentage of specific lysis was calculated as follows: percent specific lysis=100−[100×(% CFSE$^{high}$ immunized mice/% CFSE$^{low}$ immunized mice)/(% CFSE$^{high}$ naive mouse/% CFSE$^{low}$ naive mouse)].

Statistical Analysis: Significance of differences in values was analyzed using a one-way analysis of variance (ANOVA) with Bonferroni post-test (SigmaStat v. 3.11, Systat, San Jose, Calif.).

Results

Combined Elimination of Negatively Charged Glutamate 570 and of Acylated Lysine 860 Ablates Cell-permeabilizing Capacity of CyaA. The working model of CyaA action predicts that CyaA can be modified to lose its pore-forming (hemolytic) activity while preserving the capacity to deliver the AC domain into cytosol of target cells. To test this hypothesis, the inventors sought to produce CyaA constructs exhibiting as low hemolytic and cytolytic activities as possible, building on previous observation that the capacity of CyaA/AC$^-$ toxoids to lyze cells can be modulated both up or down by substitutions within the pore-forming domain (8, 12-14, 18). To enable assessment of target cell penetration also for the CyaA/AC$^-$ toxoids, the inventors derived such mutants from a CyaA/233OVA toxin that was previously tagged by insertion of the SIINFEKL peptide (SEQ ID NO: 9) from ovalbumin (OVA). This CyaA variant was chosen as the insertion of reporter K$^b$-restricted CD8$^+$T-cell epitope at residue 233 does not affect the AC activity and allows to quantify translocation of the OVA/AC enzyme into cells as elevation of cytosolic cAMP. More importantly, presence of the OVA epitope allows to assess also the capacity of enzymatically inactive CyaA/2330VA/AC$^-$ toxoids to deliver their OVA/AC$^-$ domain into cytosol of CD11b$^+$ antigen presenting cells (APC), as this enables proteasome processing and cell surface presentation of the OVA epitope on MHC Class I glycoproteins that can be determined as stimulation of OVA-specific CD8$^+$ T cells, both in vitro and in vivo (20).

To generate CyaA/AC$^-$ toxoids possibly lacking the cytolytic activity, the inventors combined the E570Q and K860R substitutions previously shown to reduce the specific hemolytic activity of CyaA on sheep erythrocytes, with the E570Q substitution having been found to reduce also the cytolytic activity of the CyaA/AC$^-$ on CD11b$^+$ J774A.1 monocytes (8, 13). These substitutions were engineered into CyaA/233OVA/AC$^-$ individually and in combination and the specific hemolytic and cytolytic activities of resulting toxoids were compared using sheep erythrocytes as model CD11b$^-$ target and J774A.1 as model CD11b$^+$ target in parallel (Table I). In agreement with results obtained previously with toxoids lacking the OVA epitope (4, 8, 13, 21), under the used conditions the OVA/AC$^-$ toxoids carrying individually the E570Q and K860R substitutions exhibited respectively a two-fold reduced (55±8) and nil (1±1) relative hemolytic activity on erythrocytes and the relative cytolytic activity of the E570Q toxoid towards CD11b-expressing J774A.1 cells was also reduced (37±10), as compared to OVA/AC$^-$. In turn, as expected from results obtained with an enzymatically active K860R construct, despite the low hemolytic activity on CD11b$^-$ erythrocytes, the K860R toxoid exhibited only a slightly reduced relative cytolytic activity on CD11b$^+$ J774A.1 cells (72±22%), confirming that the structural defect caused by the K860R substitution was rescued by interaction with the CD11b/CD18 receptor (4). Nevertheless, when combined with E570Q, the K860R substitution exhibited a clear synergic effect in reducing the relative cytolytic activity of the E570Q+K860R construct towards J774A.1 cells down to 14±7%.

TABLE I

Cytolytic activities of OVA/AC$^-$ and derivatives on sheep erythrocytes and J774A.1 macrophages.

| Protein | Lysis of erythrocytes (% of AC$^-$)$^a$ | Lysis of J774A.1 cells (% of AC$^-$)$^b$ |
|---|---|---|
| AC$^-$ | 100 ± 5 | 100 ± 10 |
| OVA/AC$^-$ | 93 ± 4 | 93 ± 12 |
| OVA/E570Q/AC$^-$ | 55 ± 8** | 37 ± 10** |
| OVA/K860R/AC$^-$ | 1 ± 1** | 72 ± 22** |
| OVA-L247Q-AC$^-$ | 97 ± 3 | 41 ± 9 |
| OVA/E570Q + K860R/AC$^-$ | 1 ± 1** | 14 ± 7** |
| OVA-E570Q-L247Q-AC$^-$ | 50 ± 12 | 40 ± 11 |
| OVA-K860R-L247Q-AC$^-$ | 1 ± 1 | 45 ± 11 |
| OVA-E570Q − K860R-L247Q-AC$^-$ | 0 ± 1 | 16 ± 10 |

Table Legend
$^a$Lysis of sheep erythrocytes was determined after 4.5 hours as the amount of hemoglobin released upon incubation of $5 \times 10^8$ RBC at 37° C. in the presence of 2 mM Ca$^{2+}$ with 5 µg/ml of the given protein (31). The hemolytic activity of CyaA/AC$^-$ was taken as 100% activity. The results represent the average of values obtained in four independent experiments performed in duplicates ± S.D with two different protein preparations.
$^b$Lysis of J774A.1 cells was determined as the amount of released lactate dehydrogenase from $10^5$ cells upon 3 hours of cell incubation with 10 µg/ml of the appropriate protein at 37° C. in D-MEM. J774A.1 cell lysis by CyaA/AC$^-$ was taken as 100%. The results represent the average of values obtained in four separate experiments performed in duplicates ± S.D with two different protein preparations (*p < 0.05; **p < 0.001).

To enable quantification of capacity of the E570Q+K860R construct to deliver the AC domain into cytosol of cells, the E570Q and K860R substitutions were transferred into enzymatically active constructs derived from CyaA/233OVA (CyaA/OVA). These were produced and purified in the same way as the AC-toxoids (not shown) and characterized for cell binding, hemolytic and AC translocation capacities on sheep erythrocytes. As shown in FIG. 1A and expected from results with toxins lacking the OVA epitope (4, 13, 21), the E570Q substitution had no impact on erythrocyte binding or the capacity of CyaA/OVA to deliver the AC domain into erythrocyte cytosol and selectively reduced only its relative hemolytic activity. As further expected (4), the K860R substitution significantly reduced the capacity of CyaA/OVA to bind and penetrate erythrocytes, causing a sharp reduction of the relative hemolytic and cell-invasive AC activities of the E570Q and E570Q+K860R mutants on erythrocytes.

It has to be noted, that the hemolytic activity of CyaA is a highly cooperative function of the amount of cell-associated CyaA (Hill number >3), suggesting that CyaA oligomerization is a prerequisite for pore formation (22). Therefore, to assess the impact of combined E570Q+K860R substitutions on the hemolytic activity, the loss of erythrocyte-binding capacity of the K860R constructs had to be compensated by increasing their concentration in the assay to 25 µg/ml (5 µg/ml for intact toxin), in order to achieve binding of equal amounts of all proteins to erythrocytes, as shown in FIG. 1B. Under these conditions the combination of E570Q and K860R substitutions exhibited a clear synergy in further reducing by a factor of two the already impaired hemolytic activities of constructs carrying the E570Q (~50%) and K860R substitutions (~30%) individually. This suggests that combination of the two substitutions affected the specific cell-permeabilizing capacity of CyaA.

Pore-forming Activity of CyaA is Dispensable for Membrane Translocation of the AC Domain. In contrast to impact of the K860R substitution on toxin activity on erythrocytes, both the E570Q and K860R substitutions were previously found to have no effect on the capacity of CyaA to bind and penetrate J774A.1 monocytes expressing the CD11b/CD18 receptor (4, 8). Moreover, as documented in FIG. 2, when the two substitutions were combined in the same toxin molecule, the CyaA/OVA/E570Q+K860R construct exhibited an equal capacity to bind J774A.1 cells (FIG. 2A) and to deliver the AC domain into their cytosol to elevate cytosolic cAMP concentrations (FIG. 2B), as did intact CyaA. At the same time, however, the doubly mutated E570Q+K860R toxoid exhibited an about seven-fold reduced (14±7%) relative cytolytic capacity on these cells (cf. Table I). This suggested that the combination of E570Q and K860R substitutions selectively impaired only the capacity of the toxoid to permeabilize J774A.1 cells and not its capacity to translocate the AC domain across cell membrane.

To test this, the inventors analyzed the cell-permeabilizing capacity of the E570Q+K860R construct in single whole cell patch-clamp experiments. Here again the AC$^-$ toxoids had to be used, in order to avoid the massive ruffling of J774A.1 cells provoked by toxin-generated cAMP (23). As shown in FIG. 3A by a representative recording of ion currents across the membrane of patch-clamped single J774A.1 cells exposed to 1 µg/ml of CyaA/OVA/AC$^-$, upon an initial lag of about 3 minutes the J774A.1 cells were progressively and massively permeabilized by CyaA/OVA/AC$^-$ and the currents across cell membrane reached −3,000 pA within 10 minutes. In contrast, as shown in FIG. 3B, exposure to the CyaA/OVA/E570Q+K860R/AC$^-$ reproducibly caused only a transient and minimal initial permeabilization of the cells, with currents across cell membrane not exceeding −200 pA and returning close to zero within 10 minutes after toxoid addition. The shown recordings were representative of at least six determinations from 3 independent experiments and demonstrate that the combination of the E570Q and K860R substitutions had a major impact on the capacity of the toxoid to permeabilize the membrane of J774A.1 cells. Given that the enzymatically active version of the same construct was fully capable to translocate the AC domain into J774A.1 cells (cf. FIG. 2B), these results strongly suggest that the cell-permeabilizing (pore-forming) activity of CyaA was not required for AC domain translocation across cellular membrane.

Membrane-permeabilizing Activity of CyaA is Dispensable for Delivery of Passenger Antigens to the Cytosolic MHC Class I Pathway. Since the assay for cytosolic cAMP could not be used for assessment of cell penetration capacity of the AC$^-$ toxoids, the surrogate assay for their capacity to deliver the reporter OVA epitope to the cytosolic processing site of the MHC class I antigen presentation pathway was used (7, 24). Towards this end, the inventors determined the capacity of C57BL/6 mouse bone marrow-derived dendritic cells (BMDCs), loaded with the toxoids, to stimulate IL-2 release by B3Z T cells that selectively recognize the complex of $K^b$ MHC class I molecules with the SIINFEKL (OVA) peptide (SEQ ID NO: 9) on APCs. As shown in FIG. 4A, the B3Z hybridoma cells were effectively stimulated upon co-incubation with BMDCs and any of the toxoids carrying the OVA epitope, but not with the mock toxoid. Moreover, the OVA/E570Q/AC$^-$ and OVA/E570Q+K860R/AC$^-$ toxoids induced stimulation of the B3Z lymphocytes by APCs in vitro with as high efficiency as intact OVA/AC$^-$ toxoid. These results confirm that the E570Q+K860R double mutant was fully capable to translocate its AC domain into BMDC cytosol for processing and presentation of the OVA epitope by $K^b$ MHC class I molecules, while being essentially unable to permeabilize the J774A.1 cells. These results suggest that the cell-permeabilizing (pore-forming) activity of CyaA was neither required for AC domain translocation across cellular membrane, nor did it play any role in the capacity of CyaA to deliver passenger epitopes into APC cytosol.

To corroborate the observed in vitro antigen delivery capacity of the non-cytolytic toxoids, the inventors assessed their in vivo capacity to prime OVA-specific cytotoxic CD8$^+$ T lymphocytes (CTL). 50 µg of the various OVA-toxoids were injected intravenously into C57BL/6 mice and one week later the OVA-specific CTL responses were assessed in immunized mice by an in vivo killing assay. C57BL/6 mice received i.v. injection of a mixture (1:1) of OVA (SIINFEKL (SEQ ID NO: 9)) peptide-loaded CFSE$^{high}$ and unloaded CFSE$^{low}$ splenocytes, followed one day later by FACS analysis of CFSE-labeled cells. As shown in FIG. 4B, immunization of mice with the mock toxoid did not induce any SIINFEKL-specific (SEQ ID NO: 9) in vivo CTL activity. In turn, immunization with the E570Q+K860R toxoid induced the same OVA-specific in vivo CTL killing response as the unmutated toxoid used as positive control, with the slight difference in the values of mean response to the intact and doubly mutated toxoids not being statistically significant (p=0.065). These results show that the cell-permeabilizing activity of CyaA was dispensable for the in vivo capacity of the CyaA/233OVA/AC$^-$ toxoids to deliver an AC-inserted passenger antigen into cytosol of APCs.

Discussion

The inventors demonstrate here that translocation of the AC domain of CyaA across the membrane of CD11b/CD18 receptor-expressing myeloid target cells does not depend on the capacity of the toxin to form pores and permeabilize the cellular membrane.

As summarized in the model proposed in FIG. 5, the inventors have previously reported that balance between the two activities of CyaA can be shifted by mutations or alternative acylation of CyaA. Enhancement of the pore-forming (hemolytic) activity at the expense of the capacity to deliver AC into cells was, indeed, observed upon lysine substitutions of glutamates 509, 516 and 581 (13, 18), or upon blocking of AC translocation by the 3D1 monoclonal antibody (MAb) (25). In turn, a shift in the opposite direction was observed for the recombinant r-Ec-CyaA, acylated in *E. coli* by palmitoleyl (C16:1) residues, as compared to the native (C16:0) palmitylated Bp-CyaA produced by *B. pertussis*. The r-Ec-CyaA was found to exhibit about four-fold reduced hemolytic activity and about ten-fold lower pore-forming activity in planar lipid bilayers than Bp-CyaA (12), while both CyaA forms were equally active in penetrating cellular membrane and translocating the AC domain into erythrocytes (17, 26). Moreover, recently the CyaA/E570Q construct was found to exhibit a full capacity to deliver the AC domain into both erythrocytes and J774A.1 macrophages, while exhibiting reduced hemolytic activity and lower specific pore-forming capacity in planar lipid bilayers than intact CyaA, with the CyaA/E570Q/AC$^-$ toxoid exhibiting a two-fold reduced cytolytic activity on J774A.1 cells (8, 13).

Despite the above mentioned and the many mutant CyaAs that the inventors characterized, the question remained whether formation of a membrane pore by CyaA is required for translocation of the AC domain across the membrane of CD11b-expressing cells. The here described CyaA/233OVA/E570Q+K860R mutant is the first construct with an importantly reduced capacity to permeabilize cells that remains fully capable of translocating the AC domain across cellular membrane. This shows that on its way to cell cytosol the translocating AC domain can bypass the cation-selective pore formed by CyaA.

The mode and path of AC domain translocation across cellular membrane, however, remain to be defined in more detail. Given the differing effects of substitutions of glutamates 509, 516, 570 and 581 on the pore-forming and AC delivery activities of CyaA (8, 13, 18), where the balance between the two activities can be almost entirely shifted in either direction by specific substitutions, the amphipathic helices harboring these glutamate residues appear to be involved in both activities of CyaA in an alternative manner. This is supported by the effect of combined E509K+E516K substitution, which yields a hyper-hemolytic CyaA unable to deliver the AC domain into cells (8, 18), while the here described E570Q+K860R combination yields the opposite, an essentially non-cytolytic CyaA that is fully competent to translocate the AC domain into J774A.1 cells (CD11b$^+$). These observations further corroborate the proposed model that the two membrane activities of CyaA would depend on different conformers inserting into membrane, one yielding translocation of the AC domain by toxin monomers and the other leading to formation of oligomeric CyaA pores (13, 18).

It remains to be defined what CyaA segments outside of the pore-forming domain are involved in AC domain translocation across membrane. Given the requirement for its structural integrity (27), the large RTX repeat domain (residues 1006 to 1706) is likely to be taking part in AC translocation into cells. It would be sized enough (700 residues) to form a hydrophilic translocation interface within cellular membrane that might allow passage of an unfolded AC domain across the membrane without a concomitant formation of a real cell-permeabilizing pore. Alternatively, CyaA might promote formation of inverted nonlamellar (inverted hexagonal phase) lipid structures (28), which might potentially take part in a well sealed protein-lipid interface through which the AC domain could slide into cell cytosol.

Last not least, a practical discovery reported herein is that the CyaA/E570Q+K860R/AC$^-$ toxoid with the much reduced cell-permeabilizing (cytolytic) activity, remains fully active in antigen delivery into CD11b$^+$ APCs. This is of importance in the light of its potential use as enhanced safety profile tool for delivery of tumor-specific antigens in second generation of CyaA/AC$^-$-derived vaccines for immunotherapy of cancer.

REFERENCES

1. Vojtova J, Kamanova J, Sebo P (2006) Bordetella adenylate cyclase toxin: a swift saboteur of host defense. *Curr Opin Microbiol* 9: 69-75.
2. Glaser P, Sakamoto H, Bellalou J, Ullmann A, Danchin A (1988) Secretion of cyclolysin, the calmodulin-sensitive adenylate cyclase-haemolysin bifunctional protein of *Bordetella pertussis*. *Embo J* 7: 3997-4004.
3. Rose T, Sebo P, Bellalou J, Ladant D (1995) Interaction of calcium with *Bordetella pertussis* adenylate cyclase toxin. Characterization of multiple calcium-binding sites and calcium-induced conformational changes. *J Biol Chem* 270: 26370-26376.
4. Masin J, et al. (2005) Acylation of lysine 860 allows tight binding and cytotoxicity of *Bordetella* adenylate cyclase on CD11b-expressing cells. *Biochemistry* 44: 12759-12766.
5. Guermonprez P, et al. (2001) The adenylate cyclase toxin of *Bordetella pertussis* binds to target cells via the alpha(M) beta(2) integrin (CD11b/CD18). *J Exp Med* 193: 1035-1044.
6. Gordon V M, Leppla S H, Hewlett E L (1988) Inhibitors of receptor-mediated endocytosis block the entry of *Bacillus anthracis* adenylate cyclase toxin but not that of *Bordetella pertussis* adenylate cyclase toxin. *Infect Immun* 56: 1066-1069.
7. Schlecht G, Loucka J, Najar H, Sebo P, Leclerc C (2004) Antigen targeting to CD11b allows efficient presentation of CD4+ and CD8+ T cell epitopes and in vivo Th1-polarized T cell priming. *J Immunol* 173: 6089-6097.
8. Basler M, Masin J, Osicka R, Sebo P (2006) Pore-forming and enzymatic activities of *Bordetella pertussis* adenylate cyclase toxin synergize in promoting lysis of monocytes. *Infect Immun* 74: 2207-2214.
9. Khelef N, Zychlinsky A, Guiso N (1993) *Bordetella pertussis* induces apoptosis in macrophages: role of adenylate cyclase-hemolysin. *Infect Immun* 61: 4064-4071.
10. Morova J, Osicka R, Masin J, Sebo P (2008) RTX cytotoxins recognize {beta}2 integrin receptors through N-linked oligosaccharides. *Proc Natl Acad Sci USA*.
11. Paccani S R, et al. (2008) Suppression of T-lymphocyte activation and chemotaxis by the adenylate cyclase toxin of *Bordetella pertussis*. *Infect Immun* 76: 2822-2832.
12. Benz R, Maier E, Ladant D, Ullmann A, Sebo P (1994) Adenylate cyclase toxin (CyaA) of Bordetella pertussis. Evidence for the formation of small ion-permeable channels and comparison with HlyA of *Escherichia coli*. *J Biol Chem* 269: 27231-27239.
13. Basler M, et al. (2007) Segments crucial for membrane translocation and pore-forming activity of *Bordetella* adenylate cyclase toxin. *J Biol Chem* 282: 12419-12429.
14. Hewleft E L, Donato G M, Gray M C (2006) Macrophage cytotoxicity produced by adenylate cyclase toxin from *Bordetella pertussis*: more than just making cyclic AMP! *Mol Microbiol* 59: 447-459.
15. Fayolle C, Sebo P, Ladant D, Ullmann A, Leclerc C (1996) In vivo induction of CTL responses by recombinant adenylate cyclase of *Bordetella pertussis* carrying viral CD8+ T cell epitopes. *J Immunol* 156: 4697-4706.
16. Rogel A, Hanski E (1992) Distinct steps in the penetration of adenylate cyclase toxin of *Bordetella pertussis* into sheep erythrocytes. Translocation of the toxin across the membrane. *J Biol Chem* 267: 22599-22605.
17. Havlicek V, et al. (2001) Mass spectrometric analysis of recombinant adenylate cyclase toxin from *Bordetella pertussis* strain 18323/pHSP9. *J Mass Spectrom* 36: 384-391.
18. Osickova A, Osicka R, Maier E, Benz R, Sebo P (1999) An amphipathic alpha-helix including glutamates 509 and 516 is crucial for membrane translocation of adenylate cyclase toxin and modulates formation and cation selectivity of its membrane channels. *J Biol Chem* 274: 37644-37650.
19. Fiser R, et al. (2007) Third activity of *Bordetella* adenylate cyclase (AC) toxin-hemolysin. Membrane translocation of AC domain polypeptide promotes calcium influx into CD11b+ monocytes independently of the catalytic and hemolytic activities. *J Biol Chem* 282: 2808-2820.
20. Osicka R, et al. (2000) Delivery of CD8(+) T-cell epitopes into major histocompatibility complex class I antigen presentation pathway by *Bordetella pertussis* adenylate cyclase: delineation of cell invasive structures and permissive insertion sites. *Infect Immun* 68: 247-256.
21. Basar T, et al. (1999) The conserved lysine 860 in the additional fatty-acylation site of *Bordetella pertussis* adenylate cyclase is crucial for toxin function independently of its acylation status. *J Biol Chem* 274: 10777-10783.
22. Szabo G, Gray M C, Hewlett E L (1994) Adenylate cyclase toxin from *Bordetella pertussis* produces ion conductance across artificial lipid bilayers in a calcium- and polarity-dependent manner. *J Biol Chem* 269: 22496-22499.
23. Kamanova J, et al. (2008) Adenylate cyclase toxin subverts phagocyte function by RhoA inhibition and unproductive ruffling. *J Immunol* 181: 5587-5597.
24. Guermonprez P, Ladant D, Karimova G, Ullmann A, Leclerc C (1999) Direct delivery of the *Bordetella pertussis* adenylate cyclase toxin to the MHC class I antigen presentation pathway. *J Immunol* 162: 1910-1916.
25. Gray M C, et al. (2001) Translocation-specific conformation of adenylate cyclase toxin from *Bordetella pertussis* inhibits toxin-mediated hemolysis. *J Bacteriol* 183: 5904-5910.
26. Hackett M, et al. (1995) Hemolytic, but not cell-invasive activity, of adenylate cyclase toxin is selectively affected by differential fatty-acylation in *Escherichia coli*. *J Biol Chem* 270: 20250-20253.
27. Iwaki M, Ullmann A, Sebo P (1995) Identification by in vitro complementation of regions required for cell-invasive activity of *Bordetella pertussis* adenylate cyclase toxin. *Mol Microbiol* 17: 1015-1024.
28. Martin C, et al. (2004) Membrane restructuring by *Bordetella pertussis* adenylate cyclase toxin, a member of the RTX toxin family. *J Bacteriol* 186: 3760-3765.
29. Karimova G, Pidoux J, Ullmann A, Ladant D (1998) A bacterial two-hybrid system based on a reconstituted signal transduction pathway. *Proc Natl Acad Sci USA* 95: 5752-5756.
30. Franken K L, et al. (2000) Purification of his-tagged proteins by immobilized chelate affinity chromatography: the benefits from the use of organic solvent. *Protein Expr Purif* 18: 95-99.
31. Bellalou J, Sakamoto H, Ladant D, Geoffroy C, Ullmann A (1990) Deletions affecting hemolytic and toxin activities of *Bordetella pertussis* adenylate cyclase. *Infect Immun* 58: 3242-3247.

The invention claimed is:

1. An isolated or purified polypeptide which is a mutant of an adenylate cyclase protein and whose amino acid sequence comprises or consists of one of the following sequences:
   a) the amino acid sequence of the adenylate cyclase (CyaA) of SEQ ID NO: 1, SEQ ID NO: 10, or SEQ ID NO: 11, wherein the following mutations have been performed:
      (i) the substitution of the glutamic acid residue at position 570 by a glutamine residue (E570Q), and
      (ii) the substitution of the lysine residue at position 860 by an arginine residue (K860R), or
   b) the amino acid sequence of the adenylate cyclase (CyaA) of SEQ ID NO: 12, wherein the following mutations have been performed:
      (i) the substitution of the glutamic acid residue at position 569 by a glutamine residue (E569Q), and
      (ii) the substitution of the lysine residue at position 859 by an arginine residue (K859R).

2. The polypeptide according to claim 1, wherein the amino acid sequence of said adenylate cyclase is the sequence of SEQ ID NO: 1 wherein the following mutations have been performed:
   (i) the substitution of the glutamic acid residue at position 570 by a glutamine residue (E570Q), and
   (ii) the substitution of the lysine residue at position 860 by an arginine residue (K860R).

3. An isolated polypeptide comprising a mutant sequence of SEQ ID NO:1, wherein the mutations comprise the substitution of the glutamic acid residue at position 570 by a glutamine residue (E570Q), the substitution of the lysine residue at position 860 by an arginine residue (K860R), and either deletion of amino acid residues 1-372 or at least one additional mutation chosen from:
   i) an insertion of an LQ or GS dipeptide between amino acids 188 or 189;
   ii) substitution of the leucine residue at position 247 by a glutamine residue or a conservative amino acid residue;
   iii) deletion of amino acid residues 225-234;
   iv) substitution of the leucine residue at position 58 by a glutamine residue; and
   v) substitution of the leucine residue at position 65 by a glutamine residue.

4. The polypeptide according to claim 1 or 3, which is capable of binding to cells and of translocating its N-terminal adenylate cyclase enzyme domain into said cells wherein said cells express the CD11b/CD18 receptor and wherein binding to said cells occurs through binding to said CD11b/CD18 receptor.

5. The polypeptide according to claim 3, which is a mutant of an adenylate cyclase toxoid whose adenylate cyclase activity in cells is partly or totally suppressed as compared to that of the *Bordetella pertussis* CyaA toxin.

6. The polypeptide according to claim 5, wherein said partial or total suppression of adenylate cyclase activity is achieved by insertion of a dipeptide between the amino acid residues at positions 188 and 189 of SEQ ID NO:1.

7. A composition comprising a polypeptide according to claim 1 and which is further combined with one or more molecules of interest.

8. The composition according to claim 7, wherein each of said one or more molecules of interest consists of an amino acid sequence suitable for eliciting an immune response.

9. The composition according to claim 8, wherein the amino acid sequence of each of said molecule(s) suitable for eliciting an immune response consists of 5 to 800 amino acid residues.

10. The composition according to claim 8, wherein the amino acid sequence of each of said molecule(s) suitable for eliciting an immune response comprises or consists of an amino acid sequence of a poliovirus antigen, an HIV virus antigen, an influenza virus antigen, a choriomeningitis virus sequence, a tumor antigen, or comprises or consists of a part of an amino acid sequence of any of these antigens which comprises at least one epitope.

11. The composition according to claim 8, which is a recombinant polypeptide wherein the amino acid sequence of each of said molecule(s) suitable for eliciting an immune response is inserted into a permissive site of the adenylate cyclase amino acid sequence of the mutant polypeptide, thereby preserving the capacity of said mutant polypeptide to translocate its N-terminal adenylate cyclase enzyme domain into target cells.

12. The composition according to claim 8, wherein each of said amino acid sequence(s) suitable for eliciting an immune response is grafted, especially chemically grafted, onto an amino acid residue of said mutant polypeptide.

13. A method of treatment comprising administering the polypeptide according to claim 1 to a host in need thereof.

14. The method of claim 13, wherein the polypeptide elicits a T-cell immune response and/or a B-cell immune response in the host.

15. The method of claim 13, further comprising administering the polypeptide in combination with an adjuvant and/or in combination with another therapeutically active molecule.

16. The method of claim 13, wherein the polypeptide is not administered in combination with an adjuvant.

17. A pharmaceutical composition comprising a polypeptide according to claim 1, a pharmaceutically acceptable carrier, and optionally an adjuvant and/or a therapeutically active molecule.

18. A method for the preparation of a proteinaceous vector suitable for the delivery of a molecule into a cell, comprising binding said molecule to a polypeptide according to claim 1.

19. A pharmaceutical composition comprising a polypeptide derivative according to claim 7, a pharmaceutically acceptable carrier, and optionally an adjuvant and/or a therapeutically active molecule.

* * * * *